US010080682B2

(12) United States Patent
Horvath et al.

(10) Patent No.: US 10,080,682 B2
(45) Date of Patent: *Sep. 25, 2018

(54) INTRASCLERAL SHUNT PLACEMENT

(71) Applicant: AqueSys, Inc., Aliso Viejo, CA (US)

(72) Inventors: Christopher Horvath, Mission Viejo, CA (US); Richard A. Lewis, Sacramento, CA (US)

(73) Assignee: AQUESYS, INC., Parsippany, NJ (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/158,368

(22) Filed: May 18, 2016

(65) Prior Publication Data

US 2016/0256323 A1 Sep. 8, 2016

Related U.S. Application Data

(63) Continuation-in-part of application No. 15/005,954, filed on Jan. 25, 2016, which is a continuation of application No. 14/508,938, filed on Oct. 7, 2014, now Pat. No. 9,271,869, which is a continuation of application No. 13/314,939, filed on Dec. 8, 2011, (Continued)

(51) Int. Cl.
*A61F 9/007* (2006.01)
*A61F 9/00* (2006.01)
*A61L 27/54* (2006.01)
*A61L 27/22* (2006.01)
(Continued)

(52) U.S. Cl.
CPC .......... *A61F 9/00781* (2013.01); *A61F 9/007* (2013.01); *A61F 9/0017* (2013.01); *A61L 27/222* (2013.01); *A61L 27/34* (2013.01); *A61L 27/54* (2013.01); *A61L 2430/16* (2013.01); *A61M 37/0069* (2013.01)

(58) Field of Classification Search
CPC .... A61F 9/00781; A61F 9/0017; A61F 9/007; A61L 27/54; A61L 27/222; A61L 27/34; A61L 2430/16; A61M 37/0069
See application file for complete search history.

(56) References Cited

U.S. PATENT DOCUMENTS 3,788,327 A 1/1974 Donowitz et al.
3,960,150 A 6/1976 Hussain et al.
(Continued)

FOREIGN PATENT DOCUMENTS

GB 2 296 663 A 7/1996
JP 2009-542370 A 12/2009
(Continued)

OTHER PUBLICATIONS

U.S. Appl. No. 13/314,939, filed Dec. 8, 2011, U.S. Pat. No. 8,852,136.
(Continued)

*Primary Examiner* — Adam Marcetich
(74) *Attorney, Agent, or Firm* — Nathan S. Smith; McDermott Will & Emery LLP

(57) ABSTRACT

Glaucoma can be treated by implanting an intraocular shunt into an eye. The eye has an anterior chamber and sclera. A shunt can be placed into the eye to establish fluid communication from the anterior chamber of the eye through the sclera, and a pharmaceutical or biological agent can be administered to the eye.

31 Claims, 41 Drawing Sheets

Related U.S. Application Data now Pat. No. 8,852,136, application No. 15/158,368, filed on May 18, 2016, which is a continuation-in-part of application No. 13/778,873, filed on Feb. 27, 2013, now Pat. No. 9,610,195, and a continuation-in-part of application No. 14/317,676, filed on Jun. 27, 2014, now Pat. No. 9,808,373.

(60) Provisional application No. 61/841,224, filed on Jun. 28, 2013, provisional application No. 61/895,341, filed on Oct. 24, 2013.

(51) Int. Cl.
*A61L 27/34* (2006.01)
*A61M 37/00* (2006.01)

(56) References Cited

U.S. PATENT DOCUMENTS

| | | |
|---|---|---|
| 4,090,530 A | 5/1978 | Lange |
| 4,402,308 A | 9/1983 | Scott |
| 4,562,463 A | 12/1985 | Lipton |
| 4,583,117 A | 4/1986 | Lipton et al. |
| 4,700,692 A | 10/1987 | Baumgartner |
| 4,722,724 A | 2/1988 | Schocket |
| 4,744,362 A | 5/1988 | Grundler |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,275,622 A | 1/1994 | Lazarus |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,573,544 A | 11/1996 | Simon et al. |
| 5,601,094 A | 2/1997 | Reiss |
| 5,651,782 A | 7/1997 | Simon et al. |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,676,679 A | 10/1997 | Simon et al. |
| 5,688,562 A | 11/1997 | Hsiung |
| 5,695,474 A | 12/1997 | Daugherty |
| 5,702,414 A | 12/1997 | Richter et al. |
| 5,704,907 A | 1/1998 | Nordquist et al. |
| 5,707,376 A | 1/1998 | Kavteladze et al. |
| 5,722,948 A | 3/1998 | Gross |
| 5,763,491 A | 6/1998 | Brandt et al. |
| 5,824,072 A | 10/1998 | Wong |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 5,964,747 A | 10/1999 | Eaton et al. |
| 5,968,058 A | 10/1999 | Richter et al. |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,159,218 A | 12/2000 | Aramant et al. |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,468,283 B1 | 10/2002 | Richter et al. |
| 6,471,666 B1 | 10/2002 | Odrich |
| 6,483,930 B1 | 11/2002 | Musgrave et al. |
| 6,510,600 B2 | 1/2003 | Yaron et al. |
| 6,514,238 B1 | 2/2003 | Hughes |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,780,164 B2 | 8/2004 | Bergheim et al. |
| 6,881,198 B2 | 4/2005 | Brown |
| 6,936,053 B1 | 8/2005 | Weiss |
| 6,939,298 B2 | 9/2005 | Brown et al. |
| 6,955,656 B2 | 10/2005 | Bergheim et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,481,816 B2 | 1/2009 | Richter et al. |
| 7,488,303 B1 | 2/2009 | Haffner et al. |
| 7,563,241 B2 | 7/2009 | Tu et al. |
| 7,594,899 B2 | 9/2009 | Pinchuk et al. |
| 7,625,384 B2 | 12/2009 | Eriksson et al. |
| 7,670,310 B2 | 3/2010 | Yaron et al. |
| 7,708,711 B2 | 5/2010 | Tu et al. |
| 7,722,549 B2 | 5/2010 | Nakao |
| 7,815,592 B2 | 10/2010 | Coroneo |

(56) References Cited

U.S. PATENT DOCUMENTS

| | | | |
|---|---|---|---|
| 7,837,644 B2 | 11/2010 | Pinchuk et al. |
| 7,850,638 B2 | 12/2010 | Theodore Coroneo |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,892,282 B2 | 2/2011 | Shepherd |
| 7,951,155 B2 | 5/2011 | Smedley et al. |
| 8,007,459 B2 | 8/2011 | Haffner et al. |
| 8,062,244 B2 | 11/2011 | Tu et al. |
| 8,075,511 B2 | 12/2011 | Tu et al. |
| 8,109,896 B2 | 2/2012 | Nissan et al. |
| 8,118,768 B2 | 2/2012 | Tu et al. |
| 8,128,588 B2 | 3/2012 | Coroneo |
| 8,167,939 B2 | 5/2012 | Silvestrini et al. |
| 8,172,899 B2 | 5/2012 | Silvestrini et al. |
| 8,262,726 B2 | 9/2012 | Silvestrini et al. |
| 8,267,882 B2 | 9/2012 | Euteneuer et al. |
| 8,273,050 B2 | 9/2012 | Bergheim et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,333,742 B2 | 12/2012 | Bergheim et al. |
| 8,337,393 B2 | 12/2012 | Silverstrini et al. |
| 8,337,445 B2 | 12/2012 | Tu et al. |
| 8,337,509 B2 | 12/2012 | Schieber et al. |
| 8,348,877 B2 | 1/2013 | Tu et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,486,086 B2 | 7/2013 | Yaron et al. |
| 8,506,515 B2 | 8/2013 | Burns et al. |
| 8,512,404 B2 | 8/2013 | Frion et al. |
| 8,529,492 B2 | 9/2013 | Clauson et al. |
| 8,529,494 B2 | 9/2013 | Euteneuer et al. |
| 8,535,333 B2 | 9/2013 | de Juan, Jr. et al. |
| 8,545,430 B2 | 10/2013 | Silvestrini |
| 8,551,166 B2 | 10/2013 | Schieber et al. |
| 8,574,294 B2 | 11/2013 | Silvestrini et al. |
| 8,579,846 B2 | 11/2013 | Tu et al. |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,192,516 B2 | 11/2015 | Horvath et al. |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath |
| 2001/0025150 A1 | 9/2001 | de Juan et al. |
| 2001/0056254 A1 | 12/2001 | Cragg et al. |
| 2002/0026239 A1* | 2/2002 | Schachar ............... A61F 2/147 623/4.1 |
| 2002/0099434 A1 | 7/2002 | Buscemi et al. |
| 2002/0133168 A1 | 9/2002 | Smedley et al. |
| 2002/0177856 A1 | 11/2002 | Richter et al. |
| 2002/0193725 A1 | 12/2002 | Odrich |
| 2003/0015203 A1 | 1/2003 | Makower |
| 2003/0050574 A1 | 3/2003 | Krueger |
| 2003/0060752 A1 | 3/2003 | Bergheim et al. |
| 2003/0079329 A1 | 5/2003 | Yaron et al. |
| 2003/0093084 A1 | 5/2003 | Nissan et al. |
| 2003/0097053 A1 | 5/2003 | Itoh |
| 2003/0181848 A1 | 9/2003 | Bergheim et al. |
| 2003/0187383 A1 | 10/2003 | Weber et al. |
| 2003/0187384 A1 | 10/2003 | Bergheim et al. |
| 2003/0236483 A1 | 12/2003 | Ren |
| 2003/0236484 A1 | 12/2003 | Lynch et al. |
| 2004/0077987 A1 | 4/2004 | Rapacki et al. |
| 2004/0102729 A1* | 5/2004 | Haffner ............... A61F 9/00781 604/8 |
| 2004/0147870 A1 | 7/2004 | Burns et al. |
| 2004/0199130 A1 | 10/2004 | Chornenky et al. |
| 2004/0210185 A1 | 10/2004 | Tu et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk et al. |
| 2005/0049578 A1 | 3/2005 | Tu et al. |
| 2005/0101967 A1 | 5/2005 | Weber et al. |
| 2005/0143363 A1 | 6/2005 | De Juan et al. |
| 2005/0209549 A1 | 9/2005 | Bergheim et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0074375 A1 | 4/2006 | Bergheim et al. |
| 2006/0084907 A1 | 4/2006 | Bergheim et al. |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0155300 A1* | 7/2006 | Stamper ............... A61F 9/00781 606/107 |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0241411 A1 | 10/2006 | Field et al. |
| 2006/0241749 A1 | 10/2006 | Tu et al. |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | De Juan et al. |
| 2007/0202186 A1* | 8/2007 | Yamamoto ........... A61K 9/0048 424/490 |
| 2007/0263172 A1 | 11/2007 | Mura |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293872 A1 | 12/2007 | Peyman |
| 2008/0015633 A1 | 1/2008 | Abbott et al. |
| 2008/0045878 A1 | 2/2008 | Bergheim et al. |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0183121 A2 | 7/2008 | Smedley et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0137983 A1 | 5/2009 | Bergheim et al. |
| 2009/0138081 A1 | 5/2009 | Bergheim et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |

(56) References Cited

U.S. PATENT DOCUMENTS

| | | |
|---|---|---|
| 2010/0004581 A1 | 1/2010 | Brigatti et al. |
| 2010/0010416 A1 | 1/2010 | Juan, Jr. et al. |
| 2010/0063478 A1 | 3/2010 | Selkee |
| 2010/0098772 A1 | 4/2010 | Robinson et al. |
| 2010/0100104 A1 | 4/2010 | Yu et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0185138 A1 | 7/2010 | Yaron et al. |
| 2010/0191103 A1 | 7/2010 | Stamper et al. |
| 2010/0249691 A1 | 9/2010 | Van Der Mooren et al. |
| 2010/0274259 A1 | 10/2010 | Yaron et al. |
| 2010/0328606 A1 | 12/2010 | Peyman |
| 2011/0009874 A1 | 1/2011 | Wardle et al. |
| 2011/0028883 A1 | 2/2011 | Juan, Jr. et al. |
| 2011/0028884 A1 | 2/2011 | Theodore Coroneo |
| 2011/0046536 A1 | 2/2011 | Stegmann et al. |
| 2011/0087149 A1 | 4/2011 | Theodore Coroneo |
| 2011/0087150 A1 | 4/2011 | Theodore Coroneo |
| 2011/0087151 A1 | 4/2011 | Theodore Coroneo |
| 2011/0092878 A1 | 4/2011 | Tu et al. |
| 2011/0098627 A1 | 4/2011 | Wilcox |
| 2011/0098629 A1 | 4/2011 | Juan, Jr. et al. |
| 2011/0105987 A1 | 5/2011 | Bergheim et al. |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0306915 A1 | 12/2011 | de Juan, Jr. et al. |
| 2012/0035524 A1* | 2/2012 | Silvestrini ............... A61F 2/90 604/8 |
| 2012/0078158 A1 | 3/2012 | Haffner et al. |
| 2012/0109040 A1 | 5/2012 | Smedley et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0220917 A1 | 8/2012 | Silvestrini et al. |
| 2012/0226150 A1 | 9/2012 | Balicki et al. |
| 2012/0253258 A1 | 10/2012 | Tu et al. |
| 2012/0310137 A1 | 12/2012 | Silvestrini |
| 2013/0006164 A1 | 1/2013 | Yaron et al. |
| 2013/0018295 A1 | 1/2013 | Haffner et al. |
| 2013/0018296 A1 | 1/2013 | Bergheim et al. |
| 2013/0110125 A1 | 5/2013 | Silvestrini et al. |
| 2013/0149429 A1 | 6/2013 | Romoda et al. |
| 2013/0150770 A1 | 6/2013 | Horvath et al. |
| 2013/0158462 A1 | 6/2013 | Wardle et al. |
| 2013/0184631 A1 | 7/2013 | Pinchuk |
| 2013/0231603 A1 | 9/2013 | Wardle et al. |
| 2013/0245532 A1 | 9/2013 | Tu |
| 2013/0245573 A1 | 9/2013 | de Juan, Jr. et al. |
| 2013/0253404 A1 | 9/2013 | Tu |
| 2013/0253405 A1 | 9/2013 | Tu |
| 2013/0253406 A1 | 9/2013 | Horvath et al. |
| 2013/0253528 A1 | 9/2013 | Haffner et al. |
| 2013/0281817 A1 | 10/2013 | Schaller et al. |
| 2013/0281908 A1 | 10/2013 | Schaller et al. |
| 2013/0281910 A1 | 10/2013 | Tu |
| 2013/0310930 A1 | 11/2013 | Tu et al. |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0180189 A1 | 6/2014 | Horvath et al. |
| 2014/0213958 A1 | 7/2014 | Clauson et al. |
| 2014/0236065 A1 | 8/2014 | Romoda et al. |
| 2014/0236066 A1 | 8/2014 | Horvath et al. |
| 2014/0236067 A1 | 8/2014 | Horvath et al. |
| 2014/0243730 A1 | 8/2014 | Horvath |
| 2014/0272102 A1 | 9/2014 | Romoda et al. |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0287077 A1 | 9/2014 | Romoda et al. |
| 2014/0303544 A1 | 10/2014 | Haffner et al. |
| 2014/0323995 A1 | 10/2014 | Clauson et al. |
| 2014/0343476 A1* | 11/2014 | Penhasi ............... A61F 9/00781 604/8 |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0038893 A1 | 2/2015 | Haffner et al. |
| 2015/0045714 A1 | 2/2015 | Horvath et al. |
| 2015/0057591 A1 | 2/2015 | Horvath et al. |
| 2015/0133946 A1 | 5/2015 | Horvath et al. |
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256323 A1 | 9/2016 | Horvath et al. |
| 2016/0278982 A1 | 9/2016 | Horvath et al. |
| 2016/0354244 A1 | 12/2016 | Horvath et al. |
| 2016/0354245 A1 | 12/2016 | Horvath et al. |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0348150 A1 | 12/2017 | Horvath et al. |

FOREIGN PATENT DOCUMENTS

| | | |
|---|---|---|
| RU | 2313315 C2 | 12/2007 |
| WO | WO-98/23237 A1 | 6/1998 |
| WO | WO-2000/056255 | 9/2000 |
| WO | WO-2002/74052 A2 | 9/2002 |
| WO | WO-2007/087061 A2 | 8/2007 |
| WO | WO-2008/005873 A2 | 1/2008 |

OTHER PUBLICATIONS

U.S. Appl. No. 13/778,873, filed Feb. 27, 2013, 2014/0243730.
U.S. Appl. No. 14/317,676, filed Jun. 27, 2014, 2015/0005689.
U.S. Appl. No. 14/508,938, filed Oct. 7, 2014, 2015/0045714.
U.S. Appl. No. 15/005,954, filed Jan. 25, 2016, 2016/0135993.
Coran, (editor in chief), "Pediatric Surgery," Elsevier Saunders, published Feb. 14, 2012, 7th Edition, vol. 1, Chapter 128, pp. 1673-1697.
Quere, "Fluid Coating on a Fiber," Annu. Rev. Fluid Mech. 1999, 31:347-84.
Horvath, U.S. Appl. No. 15/703,802, "Intraocular Shunt Implantation," filed Sep. 13, 2017.
Horvath, U.S. Appl. No. 15/703,503, "Manually Adjustable Intraocular Flow Regulation," filed Nov. 8, 2017.

* cited by examiner

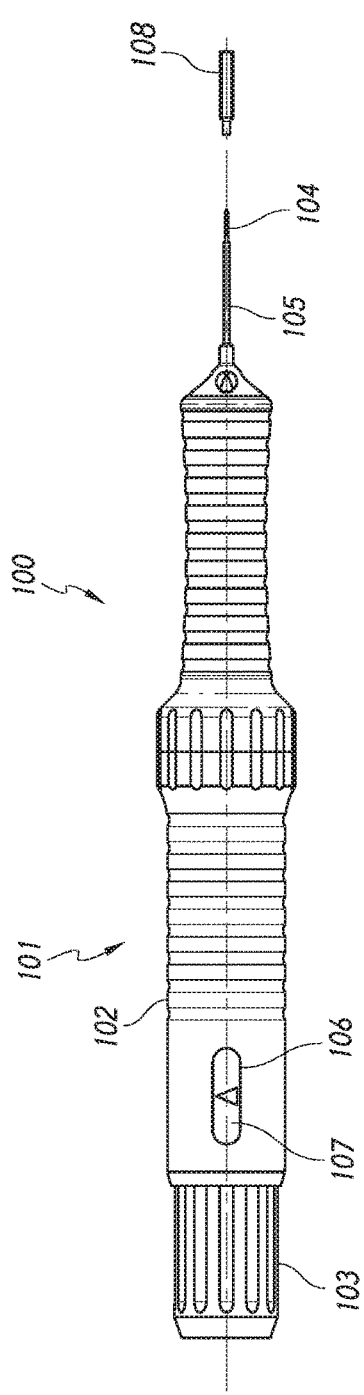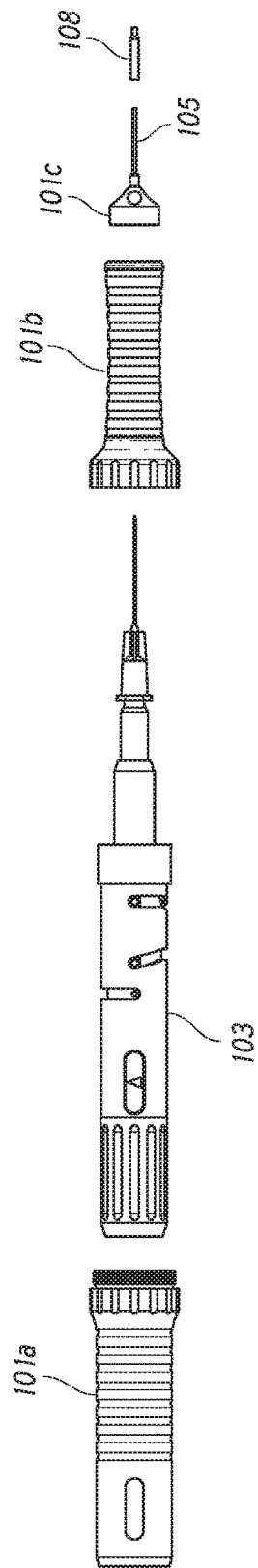
FIG. 16
FIG. 17

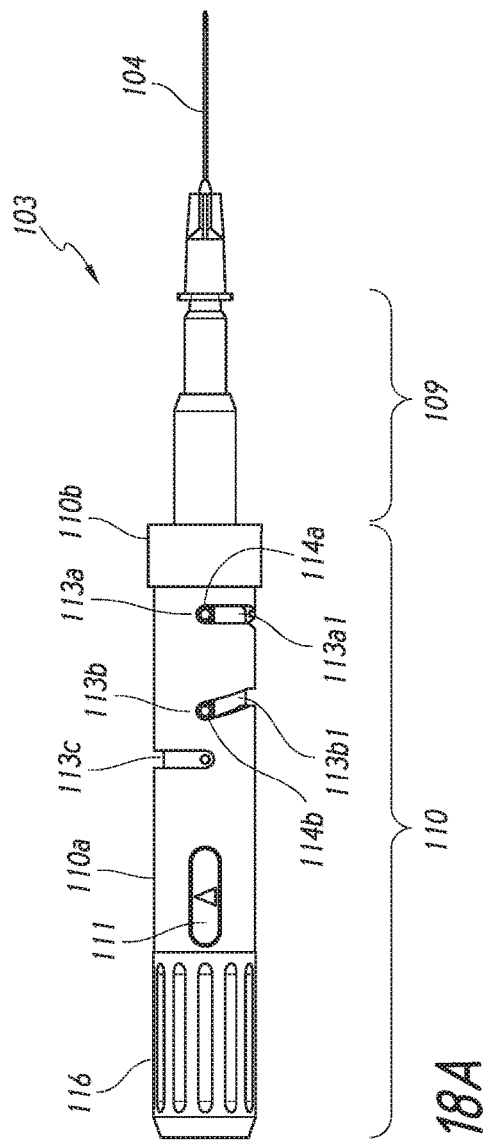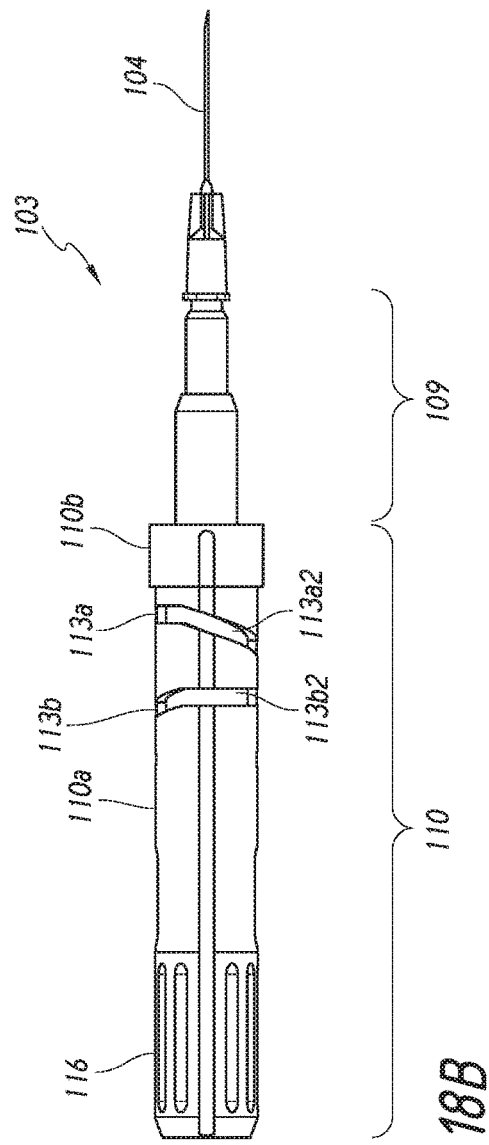

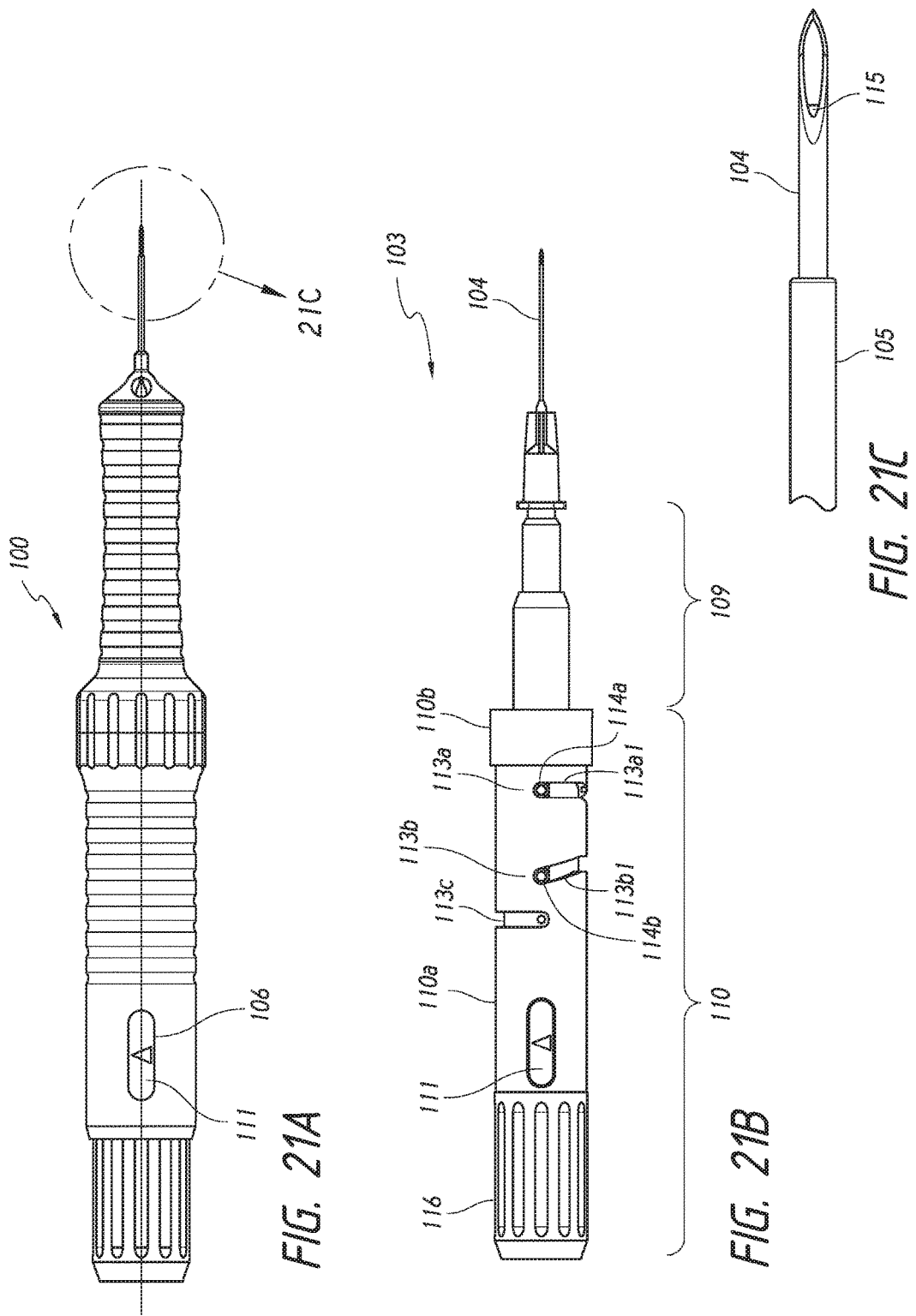

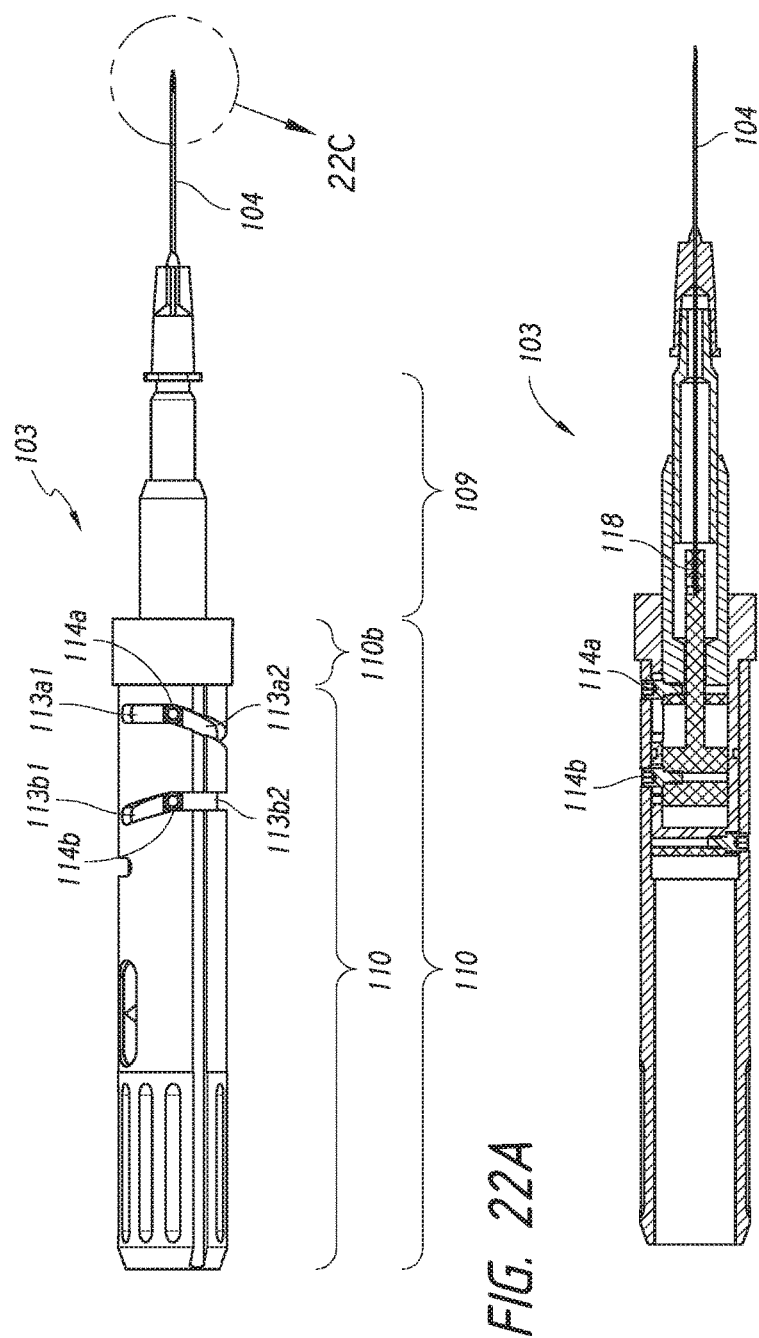
FIG. 22A  FIG. 22B  FIG. 22C

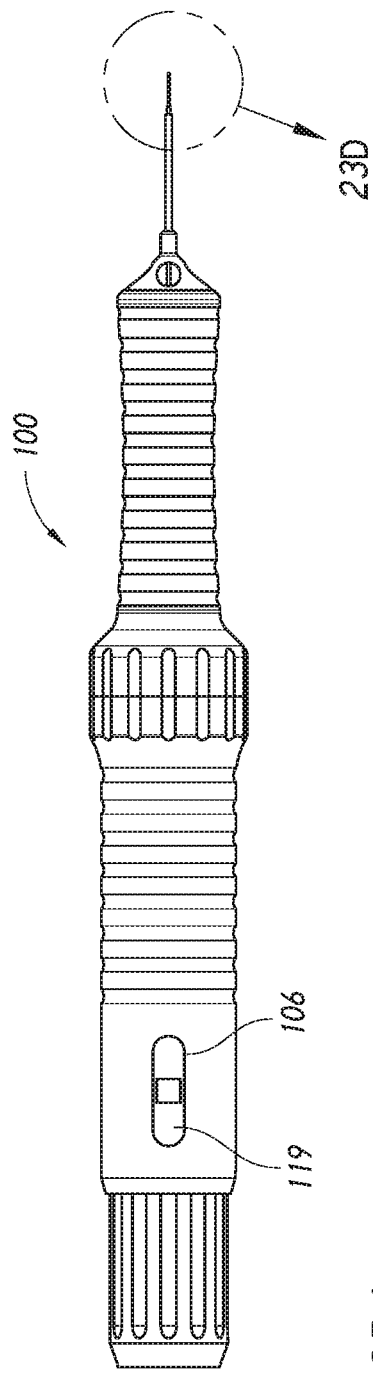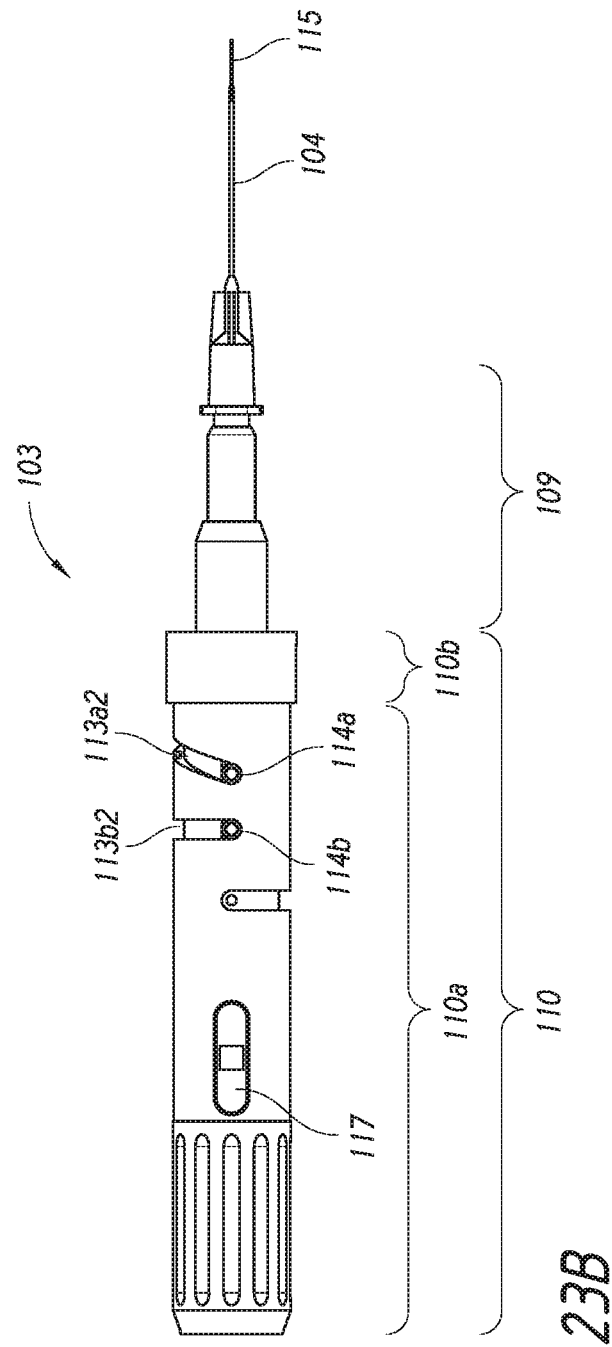
FIG. 23A
FIG. 23B

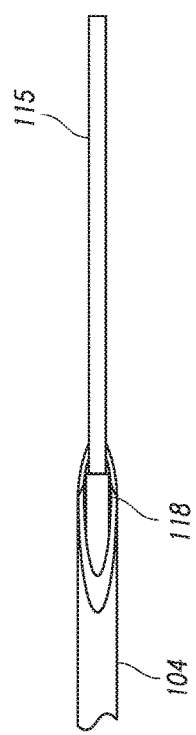
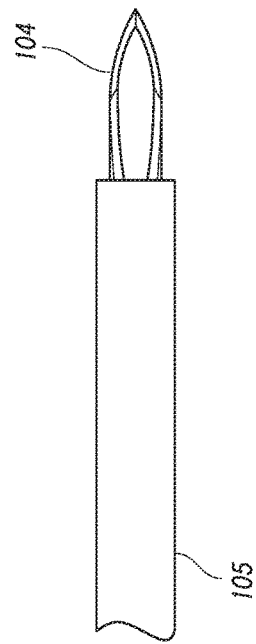
FIG. 23C
FIG. 23D

INTRASCLERAL SHUNT PLACEMENT

CROSS-REFERENCE TO RELATED APPLICATIONS

This application is a continuation-in-part of U.S. patent application Ser. No. 15/005,954, filed Jan. 25, 2016, which is a continuation of U.S. patent Ser. No. 14/508,938, filed Oct. 7, 2014, now U.S. Pat. No. 9,271,869, which is a continuation of U.S. patent application Ser. No. 13/314,939, filed Dec. 8, 2011, now U.S. Pat. No. 8,852,136; this application is also a continuation-in-part of U.S. patent application Ser. No. 13/778,873, filed Feb. 27, 2013; this application is also a continuation-in-part of U.S. patent application Ser. No. 14/317,676, filed Jun. 27, 2014, which claims the priority benefit of U.S. Provisional Application No. 61/841,224, filed on Jun. 28, 2013, and U.S. Provisional Application No. 61/895,341, filed on Oct. 24, 2013; the entirety of each of which is incorporated by reference herein.

FIELD OF THE INVENTIONS

The present inventions generally relate to devices for reducing intraocular pressure by creating a drainage pathway between the anterior chamber of the eye and the intrascleral space.

BACKGROUND

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered. Glaucoma is the second leading cause of blindness in the world, affecting 1 in 200 people under the age of fifty, and 1 in 10 over the age of eighty for a total of approximately 70 million people worldwide.

The importance of lowering intraocular pressure (IOP) in delaying glaucomatous progression has been well documented. When drug therapy fails, or is not tolerated, surgical intervention is warranted. Surgical filtration methods for lowering intraocular pressure by creating a fluid flow-path between the anterior chamber and the subconjunctival tissue have been described. One particular ab interno glaucoma filtration method has been described whereby an intraocular shunt is implanted by directing a needle which holds the shunt through the cornea, across the anterior chamber, and through the trabecular meshwork and sclera, and into the subconjunctival space. See, for example, U.S. Pat. No. 6,544,249, U.S. patent application publication number 2008/0108933, and U.S. Pat. No. 6,007,511.

Proper positioning of a shunt in the subconjunctival space is critical in determining the success or failure of subconjunctival glaucoma filtration surgery for a number of reasons. In particular, the location of the shunt has been shown to play a role in stimulating the formation of active drainage structures such as veins or lymph vessels. See, for example, U.S. patent application publication number 2008/0108933. In addition, it has been suggested that the conjunctiva itself plays a critical role in glaucoma filtration surgery. A healthy conjunctiva allows drainage channels to form and less opportunity for inflammation and scar tissue formation, which are frequent causes of failure in subconjunctival filtration surgery. See, for example, Yu et al., Progress in Retinal and Eye Research, 28: 303-328 (2009).

SUMMARY

According to some embodiments, methods and devices are provided for positioning an intraocular shunt within the eye to treat glaucoma. Various methods are disclosed herein which allow a clinician to create a fluid pathway from the anterior chamber to an area of lower pressure within the eye. Although methods may be discussed in the context of posititionng an outflow end of a shunt in a particular location (e.g., between layers of Tenon's capsule), the methods disclosed herein can be used to create a fluid pathway in which the outflow end of the shunt is positioned in other areas of low pressure, such as the supraciliary space, suprachoroidal space, the intrascleral space (i.e., between layers of sclera), intra-Tenon's adhesion space (i.e., between layers of Tenon's capsule), or subconjunctival space.

In some embodiments, the present inventions also provide methods for implanting intraocular shunts in the intrascleral space. For example, in some embodiments, methods can be performed to avoid contact between the shunt and/or delivery device with the conjunctiva. Intrascleral shunt placement safeguards the integrity of the conjunctiva to allow subconjunctival drainage pathways to successfully form. Additionally, the intrascleral space is less prone to fibrosis than the subconjunctival space and placement in the intrascleral space eliminates the risk of hypotony and related side effects.

Methods of some embodiments involve inserting into the eye a hollow shaft configured to hold an intraocular shunt, deploying the shunt from the hollow shaft such that the shunt forms a passage from the anterior chamber of the eye to the intrascleral space of the eye, and withdrawing the hollow shaft from the eye. The implanted shunt allows drainage of aqueous humor from an anterior chamber of the eye into the episcleral vessel complex, a traditional fluid drainage channel. Such placement also allows diffusion of fluid into the subconjunctival and suprachoroidal spaces.

The intraocular shunts used with methods of some embodiments define a hollow body including an inlet and an outlet, and the hollow body is configured to form a passage from the anterior chamber of the eye to the intrascleral space. In particular, the hollow body has a length sufficient to provide a passageway between the anterior chamber and the intrascleral space.

In certain aspects, some embodiments generally provide shunts composed of a material that has an elasticity modulus that is compatible with an elasticity modulus of tissue surrounding the shunt. In this manner, shunts of some embodiments are flexibility matched with the surrounding tissue, and thus will remain in place after implantation without the need for any type of anchor that interacts with the surrounding tissue. Consequently, shunts of some embodiments will maintain fluid flow away for an anterior chamber of the eye after implantation without causing irritation or inflammation to the tissue surrounding the eye.

In other aspects, some embodiments generally provide shunts in which a portion of the shunt is composed of a flexible material that is reactive to pressure, i.e., an inner diameter of the shunt fluctuates depending upon the pressures exerted on that portion of the shunt. Thus, the flexible portion of the shunt acts as a valve that regulates fluid flow through the shunt. After implantation, intraocular shunts have pressure exerted upon them by tissues surrounding the shunt (e.g., scleral tissue) and pressure exerted upon them by aqueous humor flowing through the shunt. When the pressure exerted on the flexible portion of the shunt by the surrounding tissue is greater than the pressure exerted on the flexible portion of the shunt by the fluid flowing through the shunt, the flexible portion decreases in diameter, restricting flow through the shunt. The restricted flow results in aqueous humor leaving the anterior chamber at a reduced rate.

When the pressure exerted on the flexible portion of the shunt by the fluid flowing through the shunt is greater than the pressure exerted on the flexible portion of the shunt by the surrounding tissue, the flexible portion increases in diameter, increasing flow through the shunt. The increased flow results in aqueous humor leaving the anterior chamber at an increased rate.

The flexible portion of the shunt may be any portion of the shunt. In certain embodiments, the flexible portion is a distal portion of the shunt. In certain embodiments, the entire shunt is composed of the flexible material.

Other aspects of some embodiments generally provide multi-port shunts. Such shunts reduce probability of the shunt clogging after implantation because fluid can enter or exit the shunt even if one or more ports of the shunt become clogged with particulate. In certain embodiments, the shunt includes a hollow body defining a flow path and more than two ports, in which the body is configured such that a proximal portion receives fluid from the anterior chamber of an eye and a distal portion directs the fluid to a location of lower pressure with respect to the anterior chamber.

The shunt may have many different configurations. In certain embodiments, the proximal portion of the shunt (i.e., the portion disposed within the anterior chamber of the eye) includes more than one port and the distal portion of the shunt (i.e., the portion that is located in the intrascleral space) includes a single port. In other embodiments, the proximal portion includes a single port and the distal portion includes more than one port. In still other embodiments, the proximal and the distal portions include more than one port.

The ports may be positioned in various different orientations and along various different portions of the shunt. In certain embodiments, at least one of the ports is oriented at an angle to the length of the body. In certain embodiments, at least one of the ports is oriented 90° to the length of the body.

The ports may have the same or different inner diameters. In certain embodiments, at least one of the ports has an inner diameter that is different from the inner diameters of the other ports.

Other aspects of some embodiments generally provide shunts with overflow ports. Those shunts are configured such that the overflow port remains closed until there is a pressure build-up within the shunt sufficient to force open the overflow port. Such pressure build-up typically results from particulate partially or fully clogging an entry or an exit port of the shunt. Such shunts reduce probability of the shunt clogging after implantation because fluid can enter or exit the shunt by the overflow port even if one port of the shunt becomes clogged with particulate.

In certain embodiments, the shunt includes a hollow body defining an inlet configured to receive fluid from an anterior chamber of the eye and an outlet configured to direct the fluid to a location of lower pressure with respect to the anterior chamber, the body further including at least one slit. The slit may be located at any place along the body of the shunt. In certain embodiments, the slit is located in proximity to the inlet. In other embodiments, the slit is located in proximity to the outlet. In certain embodiments, there is a slit in proximity to both the inlet and the outlet of the shunt.

In certain embodiments, the slit has a width that is substantially the same or less than an inner diameter of the inlet. In other embodiments, the slit has a width that is substantially the same or less than an inner diameter of the outlet. Generally, the slit does not direct the fluid unless the outlet is obstructed. However, the shunt may be configured such that the slit does direct at least some of the fluid even if the inlet or outlet is not obstructed.

In other aspects, some embodiments generally provide a shunt having a variable inner diameter. In some embodiments, the diameter increases from inlet to outlet of the shunt. By having a variable inner diameter that increases from inlet to outlet, a pressure gradient is produced and particulate that may otherwise clog the inlet of the shunt is forced through the inlet due to the pressure gradient. Further, the particulate will flow out of the shunt because the diameter only increases after the inlet.

In certain embodiments, the shunt includes a hollow body defining a flow path and having an inlet configured to receive fluid from an anterior chamber of an eye and an outlet configured to direct the fluid to the intrascleral space, in which the body further includes a variable inner diameter that increases along the length of the body from the inlet to the outlet. In certain embodiments, the inner diameter continuously increases along the length of the body. In other embodiments, the inner diameter remains constant along portions of the length of the body. The shunts discussed above and herein are described relative to the eye and, more particularly, in the context of treating glaucoma and solving the above identified problems relating to intraocular shunts. Nonetheless, it will be appreciated that shunts described herein may find application in any treatment of a body organ requiring drainage of a fluid from the organ and are not limited to the eye.

In other aspects, some embodiments generally provide shunts for facilitating conduction of fluid flow away from an organ, the shunt including a body, in which at least one end of the shunt is shaped to have a plurality of prongs. Such shunts reduce probability of the shunt clogging after implantation because fluid can enter or exit the shunt by any space between the prongs even if one portion of the shunt becomes clogged with particulate.

The shunt may have many different configurations. In certain embodiments, the proximal end of the shunt (i.e., the portion disposed within the anterior chamber of the eye) is shaped to have the plurality of prongs. In other embodiments, the distal end of the shunt (i.e., the portion that is located in an area of lower pressure with respect to the anterior chamber such as the intrascleral space) is shaped to have the plurality of prongs. In other embodiments, both a proximal end and a distal end of the shunt are shaped to have the plurality of prongs. In some embodiments, the shunt is a soft gel shunt.

In other aspects, some embodiments generally provide a shunt for draining fluid from an anterior chamber of an eye that includes a hollow body defining an inlet configured to receive fluid from an anterior chamber of the eye and an outlet configured to direct the fluid to a location of lower pressure with respect to the anterior chamber; the shunt being configured such that at least one end of the shunt includes a longitudinal slit. Such shunts reduce probability of the shunt clogging after implantation because the end(s) of the shunt can more easily pass particulate which would generally clog a shunt lacking the slits.

The shunt may have many different configurations. In certain embodiments, the proximal end of the shunt (i.e., the portion disposed within the anterior chamber of the eye)

includes a longitudinal slit. In other embodiments, the distal end of the shunt (i.e., the portion that is located in an area of lower pressure with respect to the anterior chamber such as intrascleral space) includes a longitudinal slit. In other embodiments, both a proximal end and a distal end of the shunt includes a longitudinal slit. In some embodiments, the shunt is a soft gel shunt.

In certain embodiments, shunts of some embodiments may be coated or impregnated with at least one pharmaceutical and/or biological agent or a combination thereof. The pharmaceutical and/or biological agent may coat or impregnate an entire exterior of the shunt, an entire interior of the shunt, or both. Alternatively, the pharmaceutical and/or biological agent may coat and/or impregnate a portion of an exterior of the shunt, a portion of an interior of the shunt, or both. Methods of coating and/or impregnating an intraocular shunt with a pharmaceutical and/or biological agent are known in the art. See for example, Darouiche (U.S. Pat. Nos. 7,790,183; 6,719,991; 6,558,686; 6,162,487; 5,902,283; 5,853,745; and 5,624,704) and Yu et al. (U.S. patent application serial number 2008/0108933). The content of each of these references is incorporated by reference herein its entirety.

In certain embodiments, the exterior portion of the shunt that resides in the anterior chamber after implantation (e.g., about 1 mm of the proximal end of the shunt) is coated and/or impregnated with the pharmaceutical or biological agent. In other embodiments, the exterior of the shunt that resides in the scleral tissue after implantation of the shunt is coated and/or impregnated with the pharmaceutical or biological agent. In other embodiments, the exterior portion of the shunt that resides in the area of lower pressure (e.g., the intrascleral space) after implantation is coated and/or impregnated with the pharmaceutical or biological agent. In embodiments in which the pharmaceutical or biological agent coats and/or impregnates the interior of the shunt, the agent may be flushed through the shunt and into the area of lower pressure (e.g., the intrascleral space).

Any pharmaceutical and/or biological agent or combination thereof may be used with shunts of some embodiments. The pharmaceutical and/or biological agent may be released over a short period of time (e.g., seconds) or may be released over longer periods of time (e.g., days, weeks, months, or even years). Exemplary agents include anti-mitotic pharmaceuticals such as Mitomycin-C or 5-Fluorouracil, anti-VEGF (such as Lucintes, Macugen, Avastin, VEGF or steroids).

BRIEF DESCRIPTION OF THE DRAWINGS

FIG. 8A shows an embodiment of a shunt in which the proximal portion of the shunt includes more than one port and the distal portion of the shunt includes a single port. FIG. 8B shows another embodiment of a shunt in which the proximal portion includes a single port and the distal portion includes more than one port. FIG. 8C shows another embodiment of a shunt in which the proximal portions include more than one port and the distal portions include more than one port.

FIG. 16 is a schematic showing an embodiment of a shunt deployment device according to some embodiments.

FIG. 17 shows an exploded view of the device shown in FIG. 16.

FIGS. 18A-18D are schematics showing different enlarged views of the deployment mechanism of the deployment device.

FIGS. 21A and 21B show schematics of the deployment mechanism in a pre-deployment configuration. FIG. 21C shows an enlarged view of the distal portion of the deployment device of FIG. 21A. This figure shows an intraocular shunt loaded within a hollow shaft of the deployment device.

FIGS. 22A and 22B show schematics of the deployment mechanism at the end of the first stage of deployment of the shunt from the deployment device. FIG. 22C shows an enlarged view of the distal portion of the deployment device of FIG. 22A. This figure shows an intraocular shunt partially deployed from within a hollow shaft of the deployment device.

FIG. 23A shows a schematic of the deployment device after deployment of the shunt from the device. FIG. 23B show a schematic of the deployment mechanism at the end of the second stage of deployment of the shunt from the deployment device. FIG. 23C shows an enlarged view of the distal portion of the deployment device after retraction of the shaft with the pusher abutting the shunt. FIG. 23D shows an enlarged view of the distal portion of the deployment device after deployment of the shunt.

DETAILED DESCRIPTION

Figure 1:
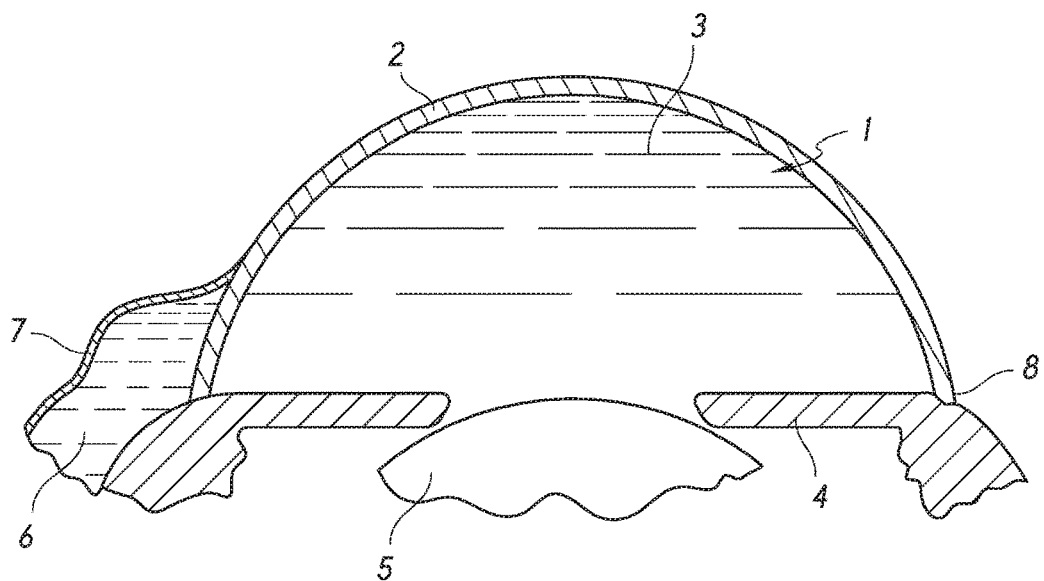
FIG. 1 provides a cross-sectional diagram of the general anatomy of the eye.

FIG. 1 provides a schematic diagram of the general anatomy of the eye. An anterior aspect of the anterior chamber 1 of the eye is the cornea 2, and a posterior aspect of the anterior chamber 1 of the eye is the iris 4. Beneath the iris 4 is the lens 5. The anterior chamber 1 is filled with aqueous humor 3. The aqueous humor 3 drains into a space(s) 6 below the conjunctiva 7 through the trabecular meshwork (not shown in detail) of the sclera 8. The aqueous humor is drained from the space(s) 6 below the conjunctiva 7 through a venous drainage system (not shown).

Figure 2:
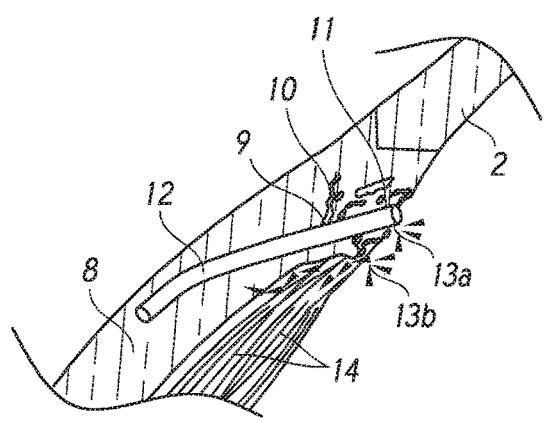
FIG. 2 provides another cross-sectional view the eye, and certain anatomical structures of the eye along with an implanted intraocular shunt.

FIG. 2 provides a cross-sectional view of a portion of the eye, and provides greater detail regarding certain anatomical structures of the eye. In particular, FIG. 2 shows a shunt 12 implanted in the sclera 8 (i.e., intrascleral implantation). Placement of shunt 12 within the sclera 8 allows aqueous humor 3 to drain into traditional fluid drainage channels of the eye (e.g., the intrascleral vein 9, the collector channel 10, Schlemm's canal 11, the trabecular outflow 13a, and the uveoscleral outflow 13b to the ciliary muscle 14.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.

Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Various structures and/or regions of the eye having lower pressure that have been targeted for aqueous humor drainage include Schlemm's canal, the subconjunctival space, the episcleral vein, the suprachoroidal space, or the subarachnoid space. Methods of implanting intraocular shunts are known in the art. Shunts may be implanted using an ab externo approach (entering through the conjunctiva and inwards through the sclera) or an ab interno approach (entering through the cornea, across the anterior chamber, through the trabecular meshwork and sclera).

Figure 3:
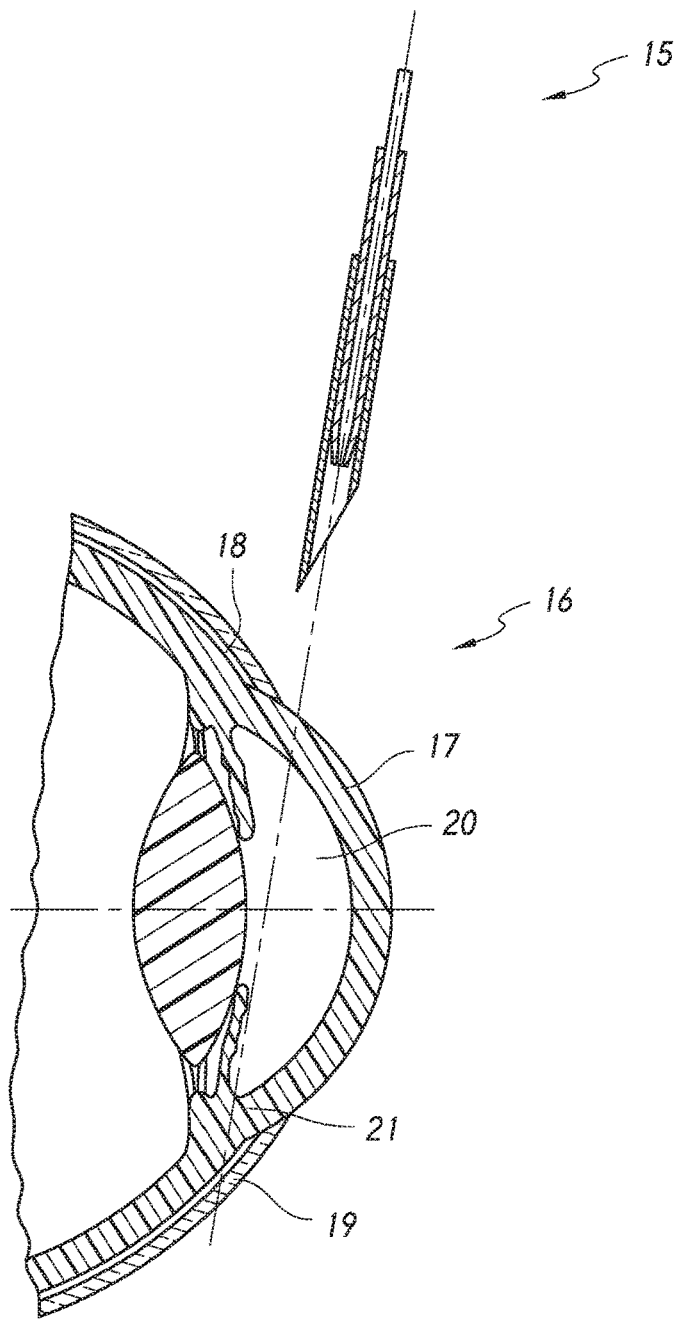
FIG. 3 depicts, implantation of an intraocular shunt with a distal end of a deployment device holding a shunt, shown in cross-section.

Ab interno approaches for implanting an intraocular shunt in the subconjunctival space are shown for example in Yu et al. (U.S. Pat. No. 6,544,249 and U.S. patent publication number 2008/0108933) and Prywes (U.S. Pat. No. 6,007,511), the contents of each of which are incorporated by reference herein in its entirety. Briefly and with reference to FIG. 3, a surgical intervention to implant the shunt involves inserting into the eye a deployment that holds an intraocular shunt, and deploying the shunt within the eye 16. A deployment device 15 holding the shunt enters the eye 16 through the cornea 17 (ab interno approach). The deployment device 15 is advanced across the anterior chamber 20 (as depicted by the broken line) in what is referred to as a transpupil implant insertion. The deployment device 15 is advanced through the sclera 21 until a distal portion of the device is in proximity to the subconjunctival space. The shunt is then deployed from the deployment device, producing a conduit between the anterior chamber and the subconjunctival space to allow aqueous humor to drain through the conjunctival lymphatic system.

While such ab interno subconjunctival filtration procedures have been successful in relieving intraocular pressure, there is a substantial risk that the intraocular shunt may be deployed too close to the conjunctiva, resulting in irritation and subsequent inflammation and/or scarring of the conjunctiva, which can cause the glaucoma filtration procedure to fail (See Yu et al., Progress in Retinal and Eye Research, 28: 303-328 (2009)). Additionally, commercially available shunts that are currently utilized in such procedures are not ideal for ab interno subconjunctival placement due to the length of the shunt (i.e., too long) and/or the materials used to make the shunt (e.g., gold, polymer, titanium, or stainless steel), and can cause significant irritation to the tissue surrounding the shunt, as well as the conjunctiva, if deployed too close.

Some embodiments of the present inventions provide methods for implanting intraocular shunts within the sclera (i.e., intrascleral implantation) and are thus suitable for use in an ab interno glaucoma filtration procedure. In methods of some embodiments, the implanted shunt forms a passage from the anterior chamber of the eye into the sclera (i.e., intrascleral space). Design and/or deployment of an intraocular shunt such that the inlet terminates in the anterior chamber and the outlet terminates intrascleral safeguards the integrity of the conjunctiva to allow subconjunctival drainage pathways to successfully form. Additionally, drainage into the intrascleral space provides access to more lymphatic channels than just the conjunctival lymphatic system, such as the episcleral lymphatic network. Moreover, design and/or deployment of an intraocular shunt such that the outlet terminates in the intrascleral space avoids having to pierce Tenon's capsule which can otherwise cause complications during glaucoma filtration surgery due to its tough and fibrous nature.

Methods for Intrascleral Shunt Placement

The methods of some embodiments involve inserting into the eye a hollow shaft configured to hold an intraocular shunt. In certain embodiments, the hollow shaft is a component of a deployment device that may deploy the intraocular shunt. The shunt is then deployed from the shaft into the eye such that the shunt forms a passage from the anterior chamber into the sclera (i.e., the intrascleral space). The hollow shaft is then withdrawn from the eye.

Referring to FIG. 2, which show an intraocular shunt placed into the eye such that the shunt forms a passage for fluid drainage from the anterior chamber to the intrascleral space. To place the shunt within the eye, a surgical intervention to implant the shunt is performed that involves inserting into the eye a deployment device that holds an intraocular shunt, and deploying at least a portion of the shunt within intrascleral space. In certain embodiments, a hollow shaft of a deployment device holding the shunt enters the eye through the cornea (ab interno approach). The shaft is advanced across the anterior chamber in what is referred to as a transpupil implant insertion. The shaft is advanced into the sclera 8 until a distal portion of the shaft is in proximity to the trabecular outflow 13b. Insertion of the shaft of the deployment device into the sclera 8 produces a long scleral channel of about 3 mm to about 5 mm in length. Withdrawal of the shaft of the deployment device prior to deployment of the shunt 12 from the device produces a space in which the shunt 12 may be deployed. Deployment of the shunt 12 allows for aqueous humor 3 to drain into traditional fluid drainage channels of the eye (e.g., the intrascleral vein 9, the collector channel 10, Schlemm's canal 11, the trabecular outflow 13a, and the uveoscleral outflow 13b to the ciliary muscle 14.

Figure 4:
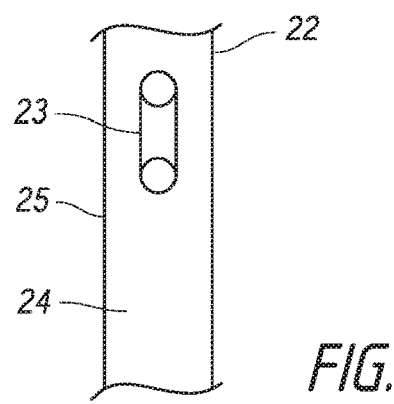
FIG. 4 depicts an example of a hollow shaft configured to hold an intraocular shunt.
Figure 5A:
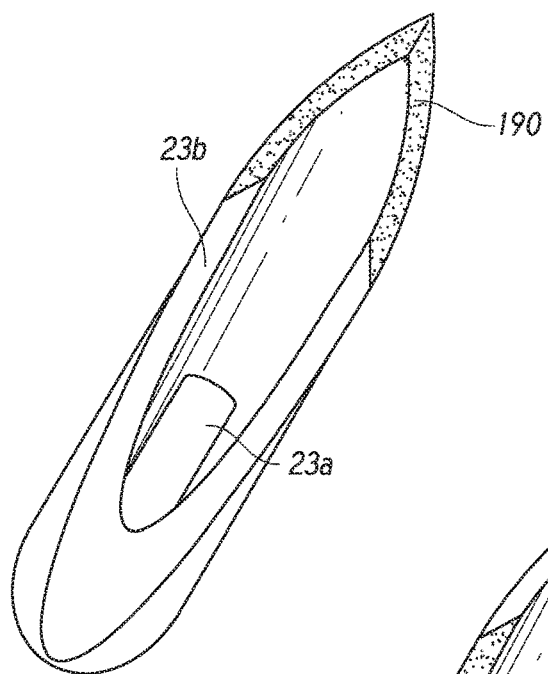
FIG. 5A depicts the tip bevel portion of a triple-ground needle tip.

FIG. 4 provides an exemplary schematic of a hollow shaft for use in accordance with the methods of some embodiments of the methods disclosed herein. This figure shows a hollow shaft 22 that is configured to hold an intraocular shunt 23. The shaft may hold the shunt within the hollow interior 24 of the shaft, as is shown in FIG. 4. Alternatively, the hollow shaft may hold the shunt on an outer surface 25 of the shaft. In some embodiments, the shunt is held completely within the hollow interior of the shaft 24, as is shown in FIG. 4. In other embodiments, a shunt 23a is only partially disposed within a hollow shaft 23b, as shown in FIG. 5A. Generally, in one embodiment, the intraocular shunts are of a cylindrical shape and have an outside cylindrical wall and a hollow interior. The shunt may have an inside diameter of about 10 μm to about 250 μm, an outside diameter of about 100 μm to about 450 μm, and a length of about 1 mm to about 12 mm. In some embodiments, the shunt has a length of about 2 mm to about 10 mm and an outside diameter of about 150 μm to about 400 μm. The hollow shaft 22 is configured to at least hold a shunt of such shape and such dimensions. However, the hollow shaft 22 may be configured to hold shunts of different shapes and different dimensions than those described above, and some embodiments can encompass a shaft 22 that may be configured to hold any shaped or dimensioned intraocular shunt.

Preferably, the methods of some embodiments are conducted by making an incision in the eye prior to insertion of the deployment device. Although in some embodiments, the methods of some embodiments may be conducted without making an incision in the eye prior to insertion of the deployment device. In certain embodiments, the shaft that is connected to the deployment device has a sharpened point or tip. In certain embodiments, the hollow shaft is a needle. Exemplary needles that may be used are commercially available from Terumo Medical Corp. (Elkington Md.). In some embodiments, the needle has a hollow interior and a beveled tip, and the intraocular shunt is held within the hollow interior of the needle. In some embodiments, the needle has a hollow interior and a triple ground point or tip.

The methods of some embodiments are preferably conducted without needing to remove an anatomical portion or feature of the eye, including but not limited to the trabecular meshwork, the iris, the cornea, or aqueous humor. The methods of some embodiments are also preferably conducted without inducing substantial ocular inflammation, such as subconjunctival blebbing or endophthalmitis. Such methods can be achieved using an ab interno approach by inserting the hollow shaft configured to hold the intraocular shunt through the cornea, across the anterior chamber, through the trabecular meshwork and into the sclera. However, the methods of some embodiments may be conducted using an ab externo approach.

Some embodiments of the methods disclosed herein can be performed such that the inserting step can further comprise the step of injecting an aqueous solution into the eye. For example, an aqueous solution can be injected below Tenon's capsule. The inserting step can also comprise ab interno insertion of the hollow shaft into the eye. Ab interno insertion can comprise inserting the hollow shaft into the eye above the corneal limbus. Ab interno insertion can comprise inserting the hollow shaft into the eye below the corneal limbus.

For example, when the methods of some embodiments are conducted using an ab interno approach, the angle of entry through the cornea affects optimal placement of the shunt in the intrascleral space. Preferably, the hollow shaft is inserted into the eye at an angle above or below the corneal limbus, in contrast with entering through the corneal limbus. For example, the hollow shaft is inserted approximately 0.25 to 3.0 mm, preferably approximately 0.5 to 2.5 mm, more preferably approximately 1.0 mm to 2.0 mm above the corneal limbus, or any specific value within said ranges, e.g., approximately 1.0 mm, approximately 1.1 mm, approximately 1.2 mm, approximately 1.3 mm, approximately 1.4 mm, approximately 1.5 mm, approximately 1.6 mm, approximately 1.7 mm, approximately 1.8 mm, approximately 1.9 mm or approximately 2.0 mm above the corneal limbus.

Without intending to be bound by any theory, placement of the shunt farther from the limbus at the exit site, as provided by an angle of entry above the limbus, is believed to provide access to more lymphatic channels for drainage of aqueous humor, such as the episcleral lymphatic network, in addition to the conjunctival lymphatic system. A higher angle of entry also results in flatter placement in the intrascleral space so that there is less bending of the shunt.

Figure 5B:
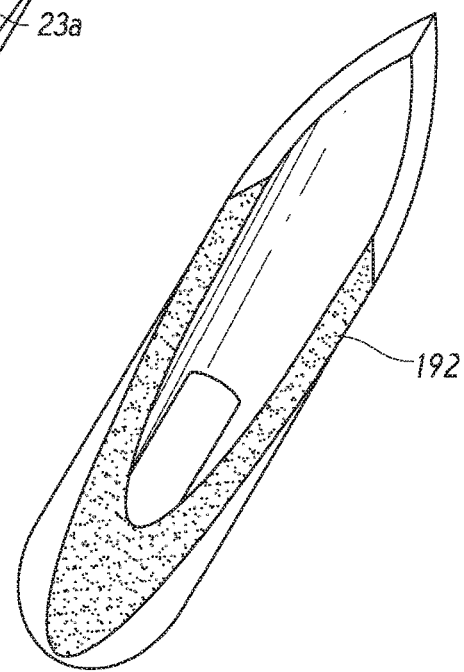
FIG. 5B depicts the flat bevel portion of a triple-ground needle tip.
Figure 5C:
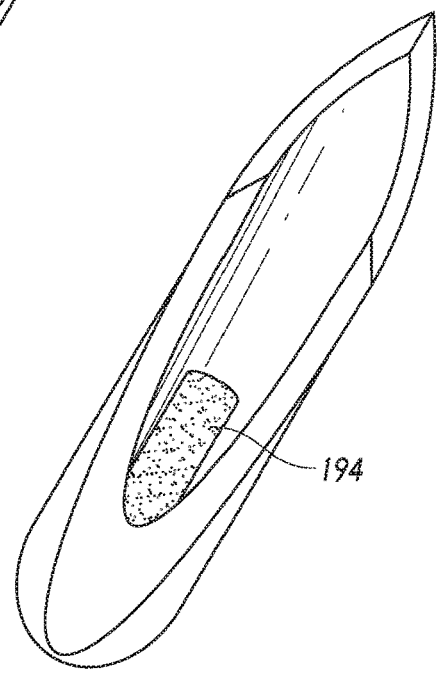
FIG. 5C depicts an intraocular shunt within a triple-ground needle tip.

In certain embodiments, to ensure proper positioning and functioning of the intraocular shunt, the depth of penetration into the sclera is important when conducting the methods of some embodiments. In one embodiment, the distal tip of the hollow shaft pierces the sclera without coring, removing or causing major tissue distortion of the surrounding eye tissue. The shunt is then deployed from the shaft. Preferably, a distal portion of the hollow shaft (as opposed to the distal tip) completely enters the sclera before the shunt is deployed from the hollow shaft. In certain embodiments, the hollow shaft is a flat bevel needle, such as a needle having a triple-ground point. The tip bevel first pierces through the sclera making a horizontal slit. In a preferred embodiment of the methods of some embodiments, the needle is advanced even further such that the entire flat bevel penetrates into the sclera, to spread and open the tissue to a full circular diameter. The tip bevel portion 190 and flat bevel portion 192 of a triple ground needle point, and the configuration of the shunt 194 disposed in the needle point, are exemplified as the gray shaded areas in FIGS. 5A-5C. Without intending to be bound by any theory, if the scleral channel is not completely forced open by the flat bevel portion of the needle, the material around the opening may not be sufficiently stretched and a pinching of the implant in that zone will likely occur, causing the shunt to fail. Full entry of the flat bevel into the sclera causes minor distortion and trauma to the local area. However, this area ultimately surrounds and conforms to the shunt once the shunt is deployed in the eye.

Intraocular Shunts

Some embodiments of the present inventions provide intraocular shunts that are configured to form a drainage pathway from the anterior chamber of the eye to the intrascleral space. In particular, the intraocular shunts of some embodiments have a length that is sufficient to form a drainage pathway from the anterior chamber of the eye to the intrascleral space. The length of the shunt is important for achieving placement specifically in the intrascleral space. A shunt that is too long will extend beyond the intrascleral space and irritate the conjunctiva which can cause the filtration procedure to fail, as previously described. A shunt that is too short will not provide sufficient access to drainage pathways such as the episcleral lymphatic system or the conjunctival lymphatic system.

Shunts of some embodiments may be any length that allows for drainage of aqueous humor from an anterior chamber of an eye to the intrascleral space. Exemplary shunts range in length from approximately 2 mm to approximately 10 mm or between approximately 4 mm to approximately 8 mm, or any specific value within said ranges. In certain embodiments, the length of the shunt is between approximately 6 to 8 mm, or any specific value within said range, e.g., 6.0 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm. 7.9 mm, or 8.0 mm.

The intraocular shunts of some embodiments are particularly suitable for use in an ab interno glaucoma filtration procedure. Commercially available shunts that are currently used in ab interno filtration procedures are typically made of a hard, inflexible material such as gold, polymer, titanium, or stainless steel, and cause substantial irritation of the eye tissue, resulting in ocular inflammation such as subconjunctival blebbing or endophthalmitis. The methods of some embodiments may be conducted using any commercially available shunts, such as the Optonol Ex-PRESS™ mini Glaucoma shunt, and the Solx DeepLight Gold™ Micro-Shunt.

In some embodiments, the intraocular shunts of some embodiments are flexible, and have an elasticity modulus that is substantially identical to the elasticity modulus of the surrounding tissue in the implant site. As such, the intraocular shunts of some embodiments are easily bendable, do not erode or cause a tissue reaction, and do not migrate once implanted. Thus, when implanted in the eye using an ab interno procedure, such as the methods described herein, the intraocular shunts of some embodiments do not induce substantial ocular inflammation such as subconjunctival blebbing or endophthalmitis. Additional exemplary features of the intraocular shunts of some embodiments are discussed in further detail below.

Tissue Compatible Shunts

In certain aspects, some embodiments generally provide shunts composed of a material that has an elasticity modulus that is compatible with an elasticity modulus of tissue surrounding the shunt. In this manner, shunts of some embodiments are flexibility matched with the surrounding tissue, and thus will remain in place after implantation without the need for any type of anchor that interacts with the surrounding tissue. Consequently, shunts of some embodiments will maintain fluid flow away for an anterior chamber of the eye after implantation without causing irritation or inflammation to the tissue surrounding the eye.

Elastic modulus, or modulus of elasticity, is a mathematical description of an object or substance's tendency to be deformed elastically when a force is applied to it. The elastic modulus of an object is defined as the slope of its stress-strain curve in the elastic deformation region:

$$\lambda \stackrel{def}{=} \frac{\text{Stress}}{\text{Strain}}$$

where lambda (λ) is the elastic modulus; stress is the force causing the deformation divided by the area to which the force is applied; and strain is the ratio of the change caused by the stress to the original state of the object. The elasticity modulus may also be known as Young's modulus (E), which describes tensile elasticity, or the tendency of an object to deform along an axis when opposing forces are applied along that axis. Young's modulus is defined as the ratio of tensile stress to tensile strain. For further description regarding elasticity modulus and Young's modulus, see for example Gere (Mechanics of Materials, $6^{th}$ Edition, 2004, Thomson), the content of which is incorporated by reference herein in its entirety.

The elasticity modulus of any tissue can be determined by one of skill in the art. See for example Samani et al. (Phys. Med. Biol. 48:2183, 2003); Erkamp et al. (Measuring The Elastic Modulus Of Small Tissue Samples, Biomedical Engineering Department and Electrical Engineering and Computer Science Department University of Michigan Ann Arbor, Mich. 48109-2125; and Institute of Mathematical Problems in Biology Russian Academy of Sciences, Pushchino, Moscow Region 142292 Russia); Chen et al. (IEEE Trans. Ultrason. Ferroelec. Freq. Control 43:191-194, 1996); Hall, (In 1996 Ultrasonics Symposium Proc., pp. 1193-1196, IEEE Cat. No. 96CH35993, IEEE, New York, 1996); and Parker (Ultrasound Med. Biol. 16:241-246, 1990), each of which provides methods of determining the elasticity modulus of body tissues. The content of each of these is incorporated by reference herein in its entirety.

The elasticity modulus of tissues of different organs is known in the art. For example, Pierscionek et al. (Br J Ophthalmol, 91:801-803, 2007) and Friberg (Experimental Eye Research, 473:429-436, 1988) show the elasticity modulus of the cornea and the sclera of the eye. The content of each of these references is incorporated by reference herein in its entirety. Chen, Hall, and Parker show the elasticity modulus of different muscles and the liver. Erkamp shows the elasticity modulus of the kidney.

Shunts of some embodiments are composed of a material that is compatible with an elasticity modulus of tissue surrounding the shunt. In certain embodiments, the material has an elasticity modulus that is substantially identical to the elasticity modulus of the tissue surrounding the shunt. In other embodiments, the material has an elasticity modulus that is greater than the elasticity modulus of the tissue surrounding the shunt. Exemplary materials includes biocompatible polymers, such as polycarbonate, polyethylene, polyethylene terephthalate, polyimide, polystyrene, polypropylene, poly(styrene-b-isobutylene-b-styrene), or silicone rubber.

In some embodiments, shunts of some embodiments are composed of a material that has an elasticity modulus that is compatible with the elasticity modulus of tissue in the eye, particularly scleral tissue. In certain embodiments, compatible materials are those materials that are softer than scleral tissue or marginally harder than scleral tissue, yet soft enough to prohibit shunt migration. The elasticity modulus for anterior scleral tissue is approximately $2.9 \pm 1.4 \times 10^6$ $N/m^2$, and $1.8 \pm 1.1 \times 10^6$ $N/m^2$ for posterior scleral tissue. See Friberg (Experimental Eye Research, 473:429-436, 1988). An exemplary material is cross linked gelatin derived from Bovine or Porcine Collagen.

Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm.

Shunts Reactive to Pressure

Figure 6:
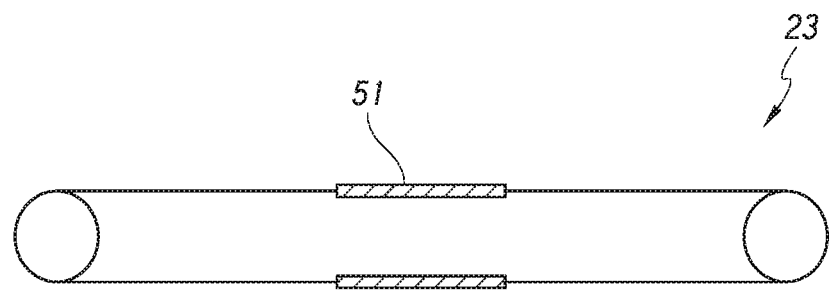
FIG. 6 provides a schematic of a shunt having a flexible portion.

In other aspects, some embodiments generally provide shunts in which a portion of the shunt is composed of a flexible material that is reactive to pressure, i.e., the diameter of the flexible portion of the shunt fluctuates depending upon the pressures exerted on that portion of the shunt. FIG. 6 provides a schematic of a shunt 23 having a flexible portion 51. In this figure, the flexible portion 51 is shown in the middle of the shunt 23. However, the flexible portion 51 may be located in any portion of the shunt, such as the proximal or distal portion of the shunt. In certain embodiments, the entire shunt is composed of the flexible material, and thus the entire shunt is flexible and reactive to pressure.

The flexible portion 51 of the shunt 23 acts as a valve that regulates fluid flow through the shunt. The human eye produces aqueous humor at a rate of about 2 µl/min for approximately 3 ml/day. The entire aqueous volume is about 0.25 ml. When the pressure in the anterior chamber falls after surgery to about 7-8 mmHg, it is assumed the majority of the aqueous humor is exiting the eye through the implant since venous backpressure prevents any significant outflow through normal drainage structures (e.g., the trabecular meshwork).

After implantation, intraocular shunts have pressure exerted upon them by tissues surrounding the shunt (e.g., scleral tissue such as the sclera channel and the sclera exit) and pressure exerted upon them by aqueous humor flowing through the shunt. The flow through the shunt, and thus the pressure exerted by the fluid on the shunt, is calculated by the equation:

$$\Phi = \frac{dV}{dT} = v\pi R^2 = \frac{\pi R^4}{8\eta}\left(\frac{-\Delta P}{\Delta x}\right) = \frac{\pi R^4}{8\eta}\frac{|\Delta P|}{L}$$

where $\Phi$ is the volumetric flow rate; V is a volume of the liquid poured (cubic meters); t is the time (seconds); v is mean fluid velocity along the length of the tube (meters/second); x is a distance in direction of flow (meters); R is the internal radius of the tube (meters); $\Delta P$ is the pressure difference between the two ends (pascals); $\eta$ is the dynamic fluid viscosity (pascal-second (Pa·s)); and L is the total length of the tube in the x direction (meters).

Figure 7A:
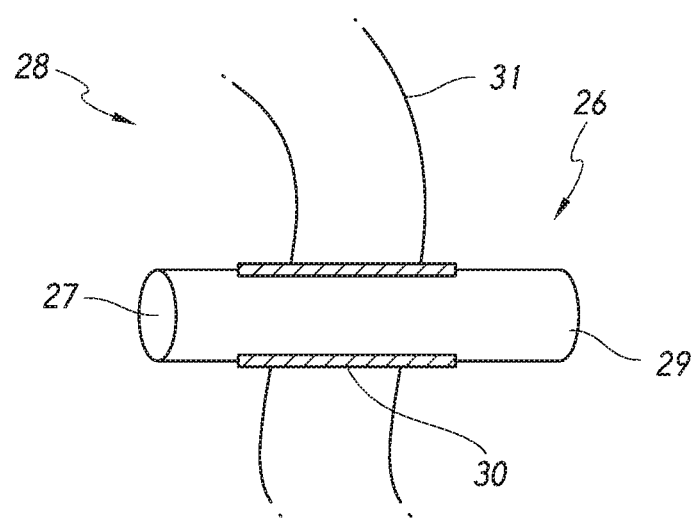
FIGS. 7A, 7B and 7C provide schematics of a shunt implanted into an eye for regulation of fluid flow from the anterior chamber of the eye to a drainage structure of the eye.

FIG. 7A provides a schematic of a shunt 26 implanted into an eye for regulation of fluid flow from the anterior chamber of the eye to an area of lower pressure (e.g., the intrascleral space). The shunt is implanted such that a proximal end 27 of the shunt 26 resides in the anterior chamber 28 of the eye, and a distal end 29 of the shunt 26 resides outside of the anterior chamber to conduct aqueous humor from the anterior chamber to an area of lower pressure. A flexible portion 30 of the shunt 26 spans at least a portion of the sclera of the eye. As shown in FIG. 7A, the flexible portion spans an entire length of the sclera 31.

Figure 7B:
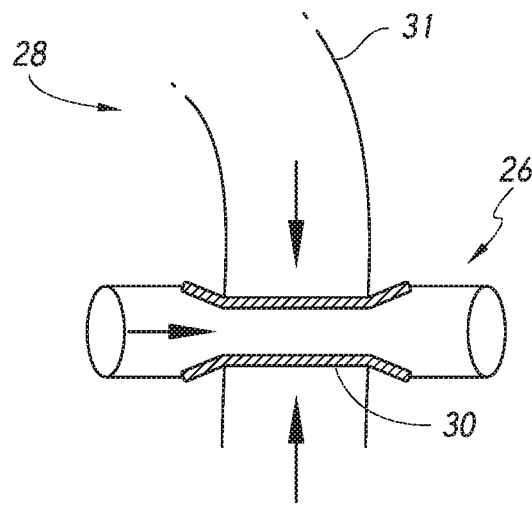

When the pressure exerted on the flexible portion 30 of the shunt 26 by sclera 31 (vertical arrows) is greater than the pressure exerted on the flexible portion 30 of the shunt 26 by the fluid flowing through the shunt (horizontal arrow), the flexible portion 30 decreases in diameter, restricting flow through the shunt 26 (FIG. 7B). The restricted flow results in aqueous humor leaving the anterior chamber 28 at a reduced rate.

Figure 7C:
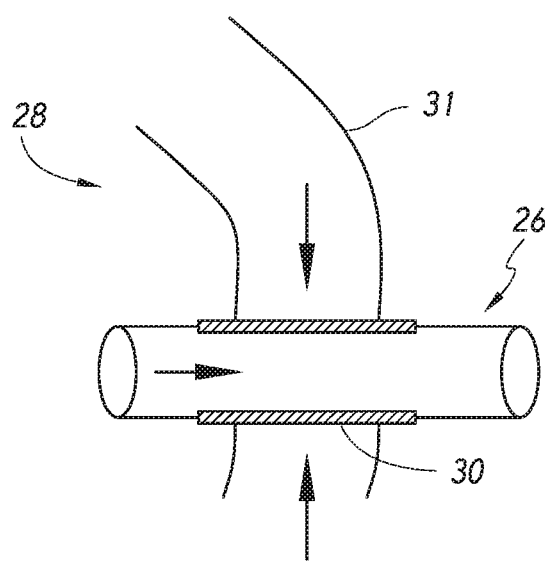

When the pressure exerted on the flexible portion 30 of the shunt 26 by the fluid flowing through the shunt (horizontal arrow) is greater than the pressure exerted on the flexible portion 30 of the shunt 26 by the sclera 31 (vertical arrows), the flexible portion 30 increases in diameter, increasing flow through the shunt 26 (FIG. 7C). The increased flow results in aqueous humor leaving the anterior chamber 28 at an increased rate.

Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm.

In a some embodiments, the shunt has a length of about 6 mm and an inner diameter of about 64 µm. With these dimensions, the pressure difference between the proximal end of the shunt that resides in the anterior chamber and the distal end of the shunt that resides outside the anterior chamber is about 4.3 mmHg. Such dimensions thus allow the implant to act as a controlled valve and protect the integrity of the anterior chamber.

It will be appreciated that different dimensioned implants may be used. For example, shunts that range in length from about 2 mm to about 10 mm and have a range in inner diameter from about 10 µm to about 100 µm allow for pressure control from approximately 0.5 mmHg to approximately 20 mmHg.

The material of the flexible portion and the thickness of the wall of the flexible portion will determine how reactive the flexible portion is to the pressures exerted upon it by the surrounding tissue and the fluid flowing through the shunt. Generally, with a certain material, the thicker the flexible portion, the less responsive the portion will be to pressure. In certain embodiments, the flexible portion is a gelatin or other similar material, and the thickness of the gelatin material forming the wall of the flexible portion ranges from about 10 µm thick to about 100 µm thick.

In a certain embodiment, the gelatin used for making the flexible portion is known as gelatin Type B from bovine skin. An exemplary gelatin is PB Leiner gelatin from bovine skin, Type B, 225 Bloom, USP. Another material that may be used in the making of the flexible portion is a gelatin Type A from porcine skin, also available from Sigma Chemical. Such gelatin is available from Sigma Chemical Company of St. Louis, Mo. under Code G-9382. Still other suitable gelatins include bovine bone gelatin, porcine bone gelatin and human-derived gelatins. In addition to gelatins, the flexible portion may be made of hydroxypropyl methylcellulose (HPMC), collagen, polylactic acid, polylglycolic acid, hyaluronic acid and glycosaminoglycans.

In certain embodiments, the gelatin is cross-linked. Cross-linking increases the inter- and intramolecular binding of the gelatin substrate. Any method for cross-linking the gelatin may be used. In some embodiments, the formed gelatin is treated with a solution of a cross-linking agent such as, but not limited to, glutaraldehyde. Other suitable compounds for cross-linking include 1-ethyl-3-(3-dimethylaminopropyl) carbodiimide (EDC). Cross-linking by radiation, such as gamma or electron beam (e-beam) may be alternatively employed.

In one embodiment, the gelatin is contacted with a solution of approximately 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should be in the range of 7 to 7.8 and, more particularly, 7.35-7.44 and typically approximately 7.4+/−0.01. If necessary, the pH may be adjusted by adding a suitable amount of a base such as sodium hydroxide as needed.

Methods for forming the flexible portion of the shunt are shown for example in Yu et al. (U.S. patent application number 2008/0108933), the content of which is incorporated by reference herein in its entirety. In an exemplary protocol, the flexible portion may be made by dipping a core or substrate such as a wire of a suitable diameter in a solution of gelatin. The gelatin solution is typically prepared by dissolving a gelatin powder in de-ionized water or sterile water for injection and placing the dissolved gelatin in a water bath at a temperature of approximately 55° C. with thorough mixing to ensure complete dissolution of the gelatin. In one embodiment, the ratio of solid gelatin to water is approximately 10% to 50% gelatin by weight to 50% to 90% by weight of water. In an embodiment, the gelatin solution includes approximately 40% by weight, gelatin dissolved in water. The resulting gelatin solution should be devoid of air bubbles and has a viscosity that is between approximately 200-500 cp and more particularly between approximately 260 and 410 cp (centipoise).

Once the gelatin solution has been prepared, in accordance with the method described above, supporting structures such as wires having a selected diameter are dipped into the solution to form the flexible portion. Stainless steel wires coated with a biocompatible, lubricious material such as polytetrafluoroethylene (Teflon) are preferred.

Typically, the wires are gently lowered into a container of the gelatin solution and then slowly withdrawn. The rate of movement is selected to control the thickness of the coat. In addition, it is preferred that a the tube be removed at a constant rate in order to provide the desired coating. To ensure that the gelatin is spread evenly over the surface of the wire, in one embodiment, the wires may be rotated in a stream of cool air which helps to set the gelatin solution and affix film onto the wire. Dipping and withdrawing the wire supports may be repeated several times to further ensure even coating of the gelatin. Once the wires have been sufficiently coated with gelatin, the resulting gelatin films on the wire may be dried at room temperature for at least 1 hour, and more preferably, approximately 10 to 24 hours. Apparatus for forming gelatin tubes are described in Yu et al. (U.S. patent application number 2008/0108933).

Once dried, the formed flexible portions may be treated with a cross-linking agent. In one embodiment, the formed flexible portion may be cross-linked by dipping the wire (with film thereon) into the 25% glutaraldehyde solution, at pH of approximately 7.0-7.8 and more preferably approximately 7.35-7.44 at room temperature for at least 4 hours and preferably between approximately 10 to 36 hours, depending on the degree of cross-linking desired. In one embodiment, the formed flexible portion is contacted with a cross-linking agent such as gluteraldehyde for at least approximately 16 hours. Cross-linking can also be accelerated when it is performed a high temperatures. It is believed that the degree of cross-linking is proportional to the bio-absorption time of the shunt once implanted. In general, the more cross-linking, the longer the survival of the shunt in the body.

The residual glutaraldehyde or other cross-linking agent is removed from the formed flexible portion by soaking the tubes in a volume of sterile water for injection. The water may optionally be replaced at regular intervals, circulated or re-circulated to accelerate diffusion of the unbound glutaraldehyde from the tube. The tubes are washed for a period of a few hours to a period of a few months with the ideal time being 3-14 days. The now cross-linked gelatin tubes may then be dried (cured) at ambient temperature for a selected period of time. It has been observed that a drying period of approximately 48-96 hours and more typically 3 days (i.e., 72 hours) may be preferred for the formation of the cross-linked gelatin tubes.

Where a cross-linking agent is used, it may be desirable to include a quenching agent in the method of making the flexible portion. Quenching agents remove unbound molecules of the cross-linking agent from the formed flexible portion. In certain cases, removing the cross-linking agent may reduce the potential toxicity to a patient if too much of the cross-linking agent is released from the flexible portion. In certain embodiments, the formed flexible portion is contacted with the quenching agent after the cross-linking treatment and, may be included with the washing/rinsing solution. Examples of quenching agents include glycine or sodium borohydride.

After the requisite drying period, the formed and cross-linked flexible portion is removed from the underlying supports or wires. In one embodiment, wire tubes may be cut at two ends and the formed gelatin flexible portion slowly removed from the wire support. In another embodiment, wires with gelatin film thereon, may be pushed off using a plunger or tube to remove the formed gelatin flexible portion.

Multi-port Shunts

Other aspects of some embodiments generally provide multi-port shunts. Such shunts reduce probability of the shunt clogging after implantation because fluid can enter or exit the shunt even if one or more ports of the shunt become clogged with particulate. In certain embodiments, the shunt includes a hollow body defining a flow path and more than two ports, in which the body is configured such that a proximal portion receives fluid from the anterior chamber of an eye and a distal portion directs the fluid to drainage structures associated with the intrascleral space.

Figure 8A:
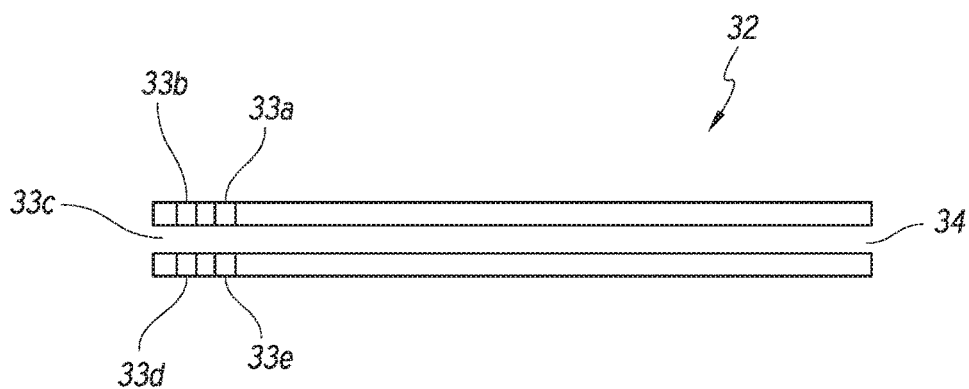
FIGS. 8A-8C show different embodiments of multi-port shunts.
Figure 8B:
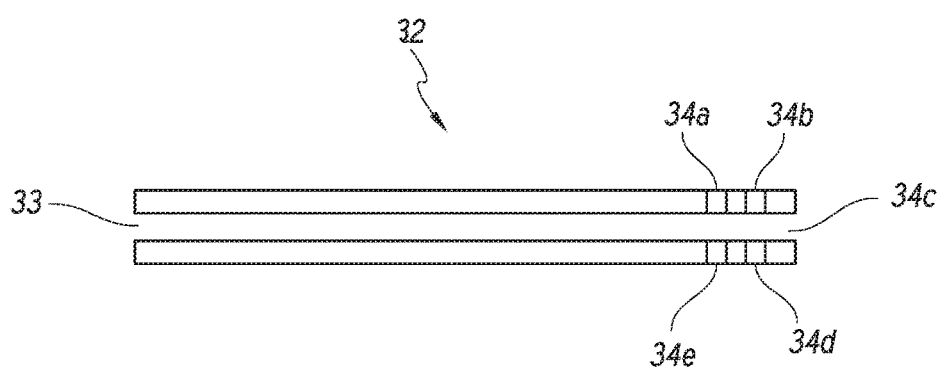
Figure 8C:
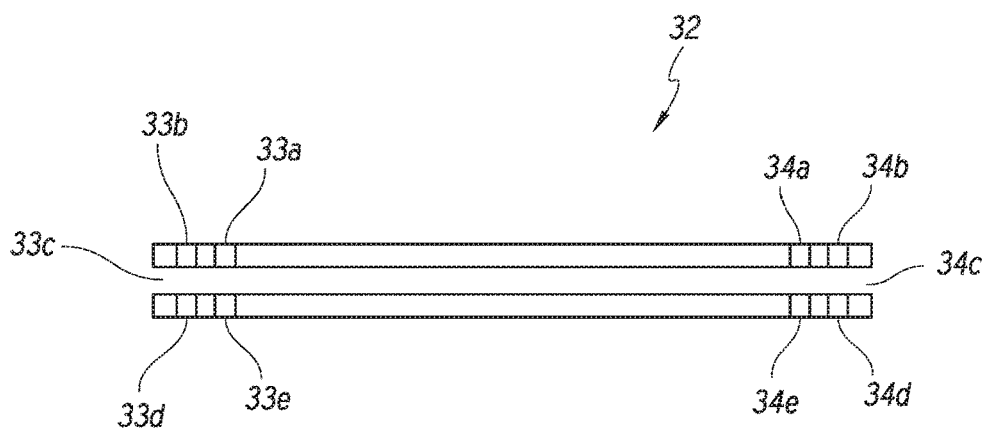

The shunt may have many different configurations. FIGS. 8A-8C shows an embodiment of a shunt 32 in which the proximal portion of the shunt (i.e., the portion disposed within the anterior chamber of the eye) includes more than one port (designated as numbers 33a-33e) and the distal portion of the shunt (i.e., the portion that is located in the intrascleral space) includes a single port 34. FIG. 8B shows another embodiment of a shunt 32 in which the proximal portion includes a single port 33 and the distal portion includes more than one port (designated as numbers 34a-34e). FIG. 8C shows another embodiment of a shunt 32 in which the proximal portions include more than one port (designated as numbers 33a-33e) and the distal portions include more than one port (designated as numbers 34a-34e). While FIGS. 8A-8C show shunts have five ports at the proximal portion, distal portion, or both, those shunts are only exemplary embodiments. The ports may be located along any portion of the shunt, and shunts of some embodiments include all shunts having more than two ports. For example, shunts of some embodiments may include at least three ports, at least four ports, at least five ports, at least 10 ports, at least 15 ports, or at least 20 ports.

The ports may be positioned in various different orientations and along various different portions of the shunt. In certain embodiments, at least one of the ports is oriented at an angle to the length of the body. In certain embodiments, at least one of the ports is oriented 90° to the length of the body. See for example FIG. 8A, which depicts ports 33a, 33b, 33d, and 33e as being oriented at a 90° angle to port 33c.

Figure 9A:
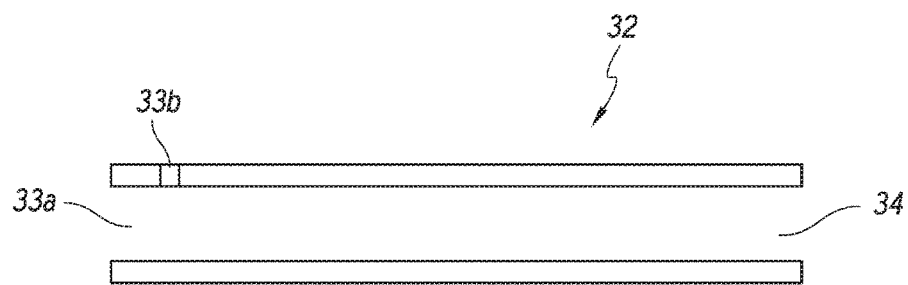
FIGS. 9A and 9B show different embodiments of multi-port shunts having different diameter ports.
Figure 9B:
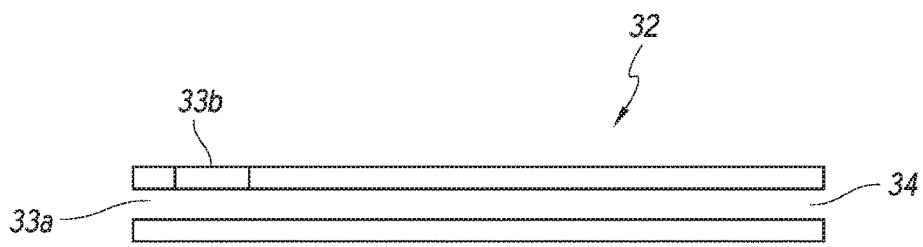

The ports may have the same or different inner diameters. In certain embodiments, at least one of the ports has an inner diameter that is different from the inner diameters of the other ports. FIGS. 9A and 9B show an embodiment of a shunt 32 having multiple ports (33a and 33b) at a proximal end and a single port 34 at a distal end. FIG. 9A shows that port 33b has an inner diameter that is different from the inner diameters of ports 33a and 34. In this figure, the inner diameter of port 33b is less than the inner diameter of ports 33a and 34. An exemplary inner diameter of port 33b is from about 20 µm to about 40 µm, particularly about 30 µm. In other embodiments, the inner diameter of port 33b is greater than the inner diameter of ports 33a and 34. See for example FIG. 9B.

Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of some embodiments may be made from any biocompatible material. An exemplary material is gelatin. Methods of making shunts composed of gelatin are described above.

Shunts with Overflow Ports

Other aspects of some embodiments generally provide shunts with overflow ports. Those shunts are configured such that the overflow port remains partially or completely closed until there is a pressure build-up within the shunt sufficient to force open the overflow port. Such pressure build-up typically results from particulate partially or fully clogging an entry or an exit port of the shunt. Such shunts reduce probability of the shunt clogging after implantation because fluid can enter or exit the shunt by the overflow port even if one port of the shunt becomes clogged with particulate.

Figure 10A:
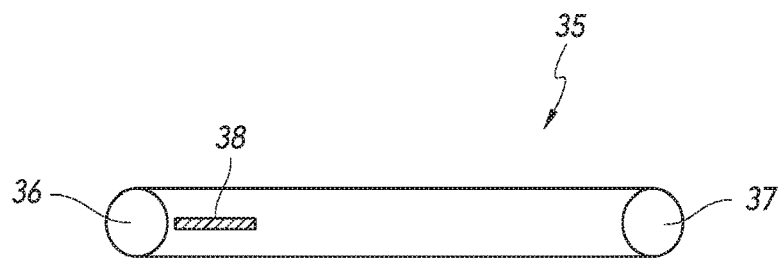
FIGS. 10A-10C provide schematics of shunts having a slit located along a portion of the length of the shunt.
Figure 10B:
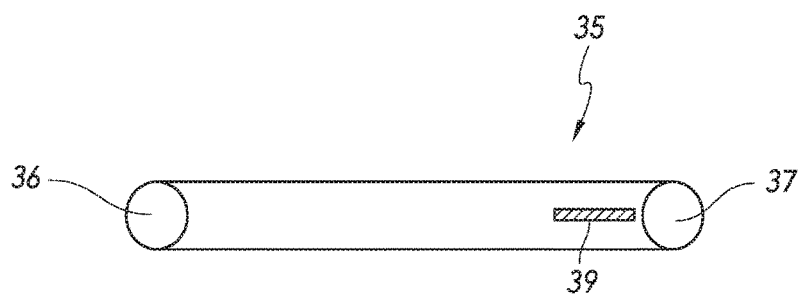
Figure 10C:
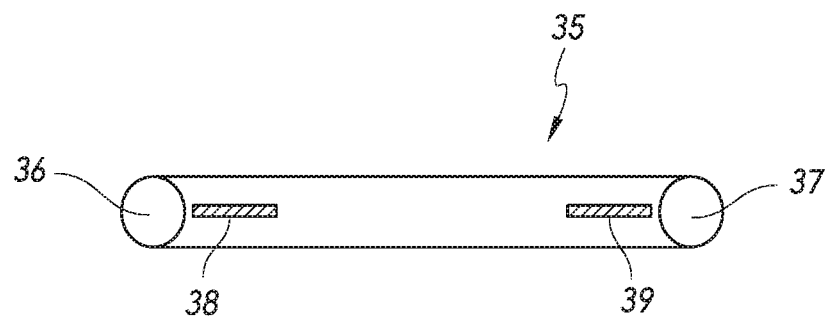

In certain embodiments, the shunt includes a hollow body defining an inlet configured to receive fluid from an anterior chamber of an eye and an outlet configured to direct the fluid to the intrascleral space, the body further including at least one slit. The slit may be located at any place along the body of the shunt. FIG. 10A shows a shunt 35 having an inlet 36, an outlet 37, and a slit 38 located in proximity to the inlet 36. FIG. 10B shows a shunt 35 having an inlet 36, an outlet 37, and a slit 39 located in proximity to the outlet 37. FIG. 10C shows a shunt 35 having an inlet 36, an outlet 37, a slit 38 located in proximity to the inlet 36, and a slit 39 located in proximity to the outlet 37.

Figure 11:
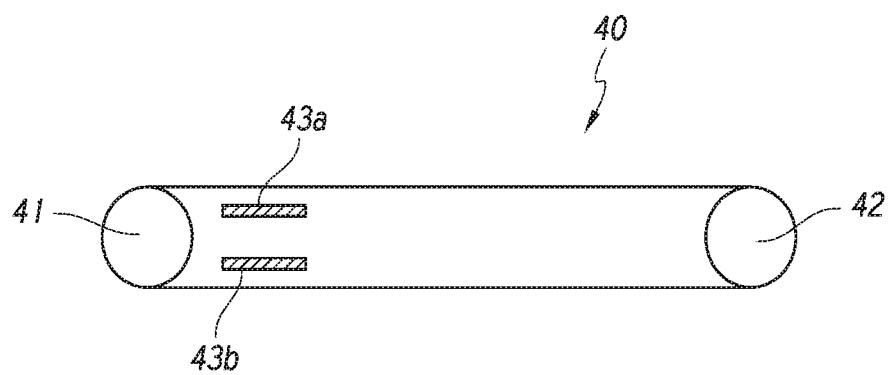
FIG. 11 depicts a shunt having multiple slits along a length of the shunt.

While FIGS. 10A-10C show shunts have only a single overflow port at the proximal portion, the distal portion, or both the proximal and distal portions, those shunts are only exemplary embodiments. The overflow port(s) may be located along any portion of the shunt, and shunts of some embodiments include shunts having more than one overflow port. In certain embodiments, shunts of some embodiments include more than one overflow port at the proximal portion, the distal portion, or both. For example, FIG. 11 shows a shunt 40 having an inlet 41, an outlet 42, and slits 43a and 43b located in proximity to the inlet 41. Shunts of some embodiments may include at least two overflow ports, at least three overflow ports, at least four overflow ports, at least five overflow ports, at least 10 overflow ports, at least 15 overflow ports, or at least 20 overflow ports. In certain embodiments, shunts of some embodiments include two slits that overlap and are oriented at 90° to each other, thereby forming a cross.

Figure 12:
FIG. 12 depicts a shunt having a slit at a proximal end of the shunt.

In certain embodiments, the slit may be at the proximal or the distal end of the shunt, producing a split in the proximal or the distal end of the implant. FIG. 12 shows an embodiment of a shunt 44 having an inlet 45, outlet 46, and a slit 47 that is located at the proximal end of the shunt, producing a split in the inlet 45 of the shunt.

In certain embodiments, the slit has a width that is substantially the same or less than an inner diameter of the inlet. In other embodiments, the slit has a width that is substantially the same or less than an inner diameter of the outlet. In certain embodiments, the slit has a length that ranges from about 0.05 mm to about 2 mm, and a width that ranges from about 10 µm to about 200 µm. Generally, the slit does not direct the fluid unless the outlet is obstructed. However, the shunt may be configured such that the slit does direct at least some of the fluid even if the inlet or outlet is not obstructed.

Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Shunts of some embodiments may be made from any biocompatible material. An exemplary material is gelatin. Methods of making shunts composed of gelatin are described above.

Shunts Having a Variable Inner Diameter

In other aspects, some embodiments generally provide a shunt having a variable inner diameter. In some embodiments, the diameter increases from inlet to outlet of the shunt. By having a variable inner diameter that increases from inlet to outlet, a pressure gradient is produced and particulate that may otherwise clog the inlet of the shunt is forced through the inlet due to the pressure gradient. Further, the particulate will flow out of the shunt because the diameter only increases after the inlet.

Figure 13:
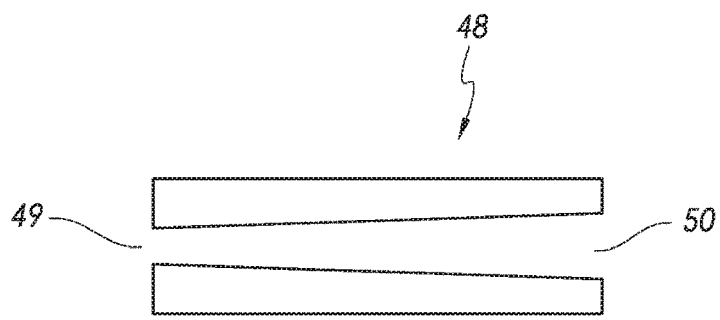
FIG. 13 provides a schematic of a shunt that has a variable inner diameter.

FIG. 13 shows an embodiment of a shunt 48 having an inlet 49 configured to receive fluid from an anterior chamber of an eye and an outlet 50 configured to direct the fluid to a location of lower pressure with respect to the anterior chamber, in which the body further includes a variable inner diameter that increases along the length of the body from the inlet 49 to the outlet 50. In certain embodiments, the inner diameter continuously increases along the length of the body, for example as shown in FIG. 13. In other embodiments, the inner diameter remains constant along portions of the length of the body.

In exemplary embodiments, the inner diameter may range in size from about 10 µm to about 200 µm, and the inner diameter at the outlet may range in size from about 15 μm to about 300 μm. Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 μm to approximately 250 μm, an outside diameter from approximately 100 μm to approximately 450 μm, and a length from approximately 2 mm to approximately 10 mm. Shunts of some embodiments may be made from any biocompatible material. An exemplary material is gelatin. Methods of making shunts composed of gelatin are described above.

Shunts Having Pronged Ends

In other aspects, some embodiments generally provide shunts for facilitating conduction of fluid flow away from an organ, the shunt including a body, in which at least one end of the shunt is shaped to have a plurality of prongs. Such shunts reduce probability of the shunt clogging after implantation because fluid can enter or exit the shunt by any space between the prongs even if one portion of the shunt becomes clogged with particulate.

FIGS. 14A-14D show embodiments of a shunt 52 in which at least one end of the shunt 52 includes a plurality of prongs 53a-d. FIGS. 14A-14D show embodiments in which both a proximal end and a distal end of the shunt are shaped to have the plurality of prongs. However, numerous different configurations are envisioned. For example, in certain embodiments, only the proximal end of the shunt is shaped to have the plurality of prongs. In other embodiments, only the distal end of the shunt is shaped to have the plurality of prongs.

Figure 14A:
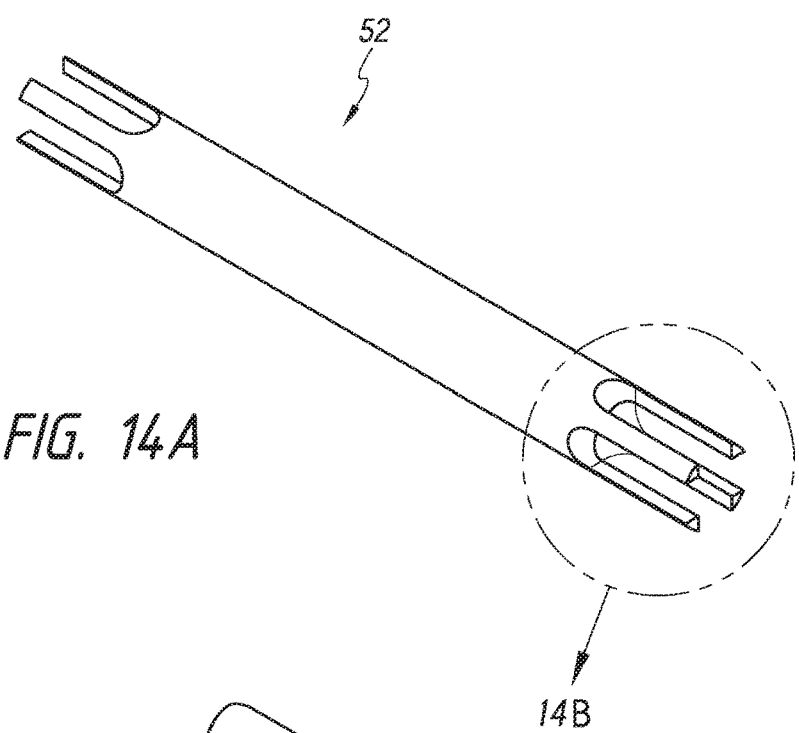
FIGS. 14A-14D depict a shunt having multiple prongs at a distal and/or proximal end.
Figure 14B:
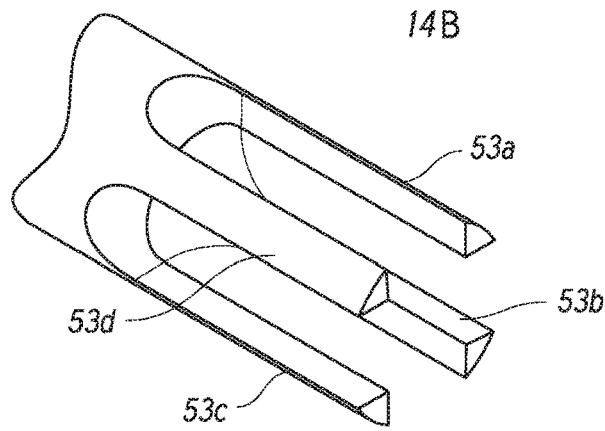
Figure 14C:
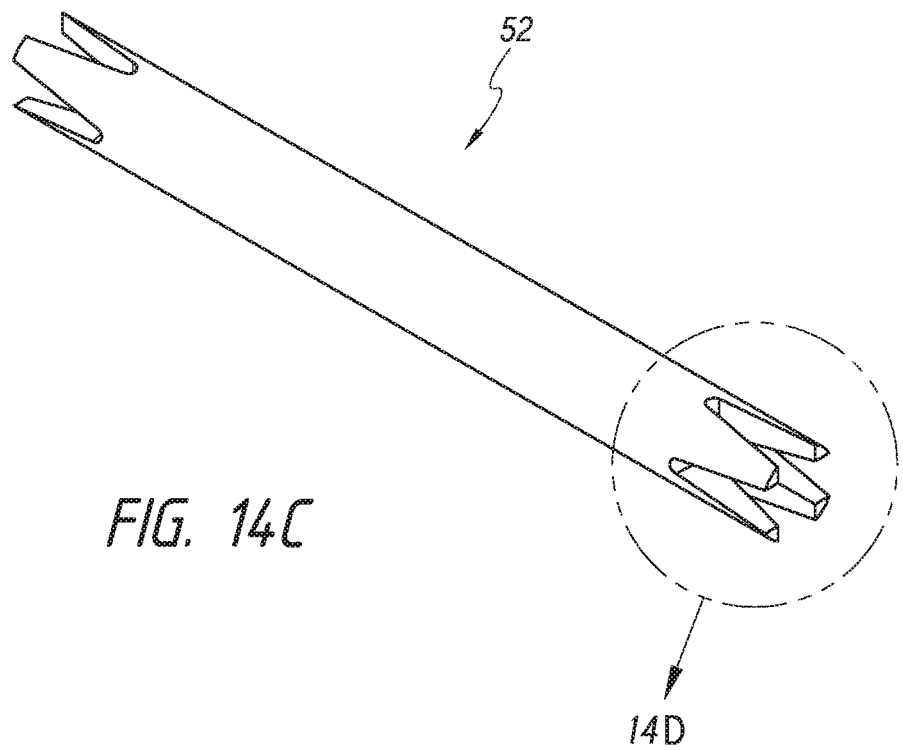
Figure 14D:
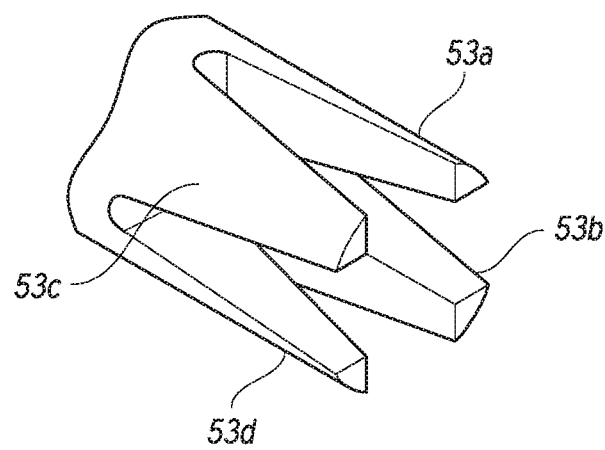

Prongs 53a-d can have any shape (i.e., width, length, height). FIGS. 14A and 14B show prongs 53a-d as straight prongs. In this embodiment, the spacing between the prongs 53a-d is the same. In another embodiment shown in FIGS. 14C and 14D, prongs 53a-d are tapered. In this embodiment, the spacing between the prongs increases toward a proximal and/or distal end of the shunt 52.

FIGS. 14A-14D show embodiments that include four prongs. However, shunts of some embodiments may accommodate any number of prongs, such as two prongs, three prongs, four prongs, five prongs, six prongs, seven prongs, eight prongs, nine prongs, ten prongs, etc. The number of prongs chosen will depend on the desired flow characteristics of the shunt.

Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 μm to approximately 250 an outside diameter from approximately 100 μm to approximately 450 μm, and a length from approximately 2 mm to approximately 10 mm. Shunts of some embodiments may be made from any biocompatible material. An exemplary material is gelatin. Methods of making shunts composed of gelatin are described above.

Shunts Having a Longitudinal Slit

In other aspects, some embodiments generally provide a shunt for draining fluid from an anterior chamber of an eye that includes a hollow body defining an inlet configured to receive fluid from an anterior chamber of the eye and an outlet configured to direct the fluid to a location of lower pressure with respect to the anterior chamber; the shunt being configured such that at least one end of the shunt includes a longitudinal slit. Such shunts reduce probability of the shunt clogging after implantation because the end(s) of the shunt can more easily pass particulate which would generally clog a shunt lacking the slits.

FIGS. 15A-15D show embodiments of a shunt 54 in which at least one end of the shunt 54 includes a longitudinal slit 55 that produces a top portion 56a and a bottom portion 56b in a proximal and/or distal end of the shunt 54. FIGS. 15A-15D show an embodiment in which both a proximal end and a distal end include a longitudinal slit 55 that produces a top portion 56a and a bottom portion 56b in both ends of the shunt 54. However, numerous different configurations are envisioned. For example, in certain embodiments, only the proximal end of the shunt includes longitudinal slit 55. In other embodiments, only the distal end of the shunt includes longitudinal slit 55.

Figure 15A:
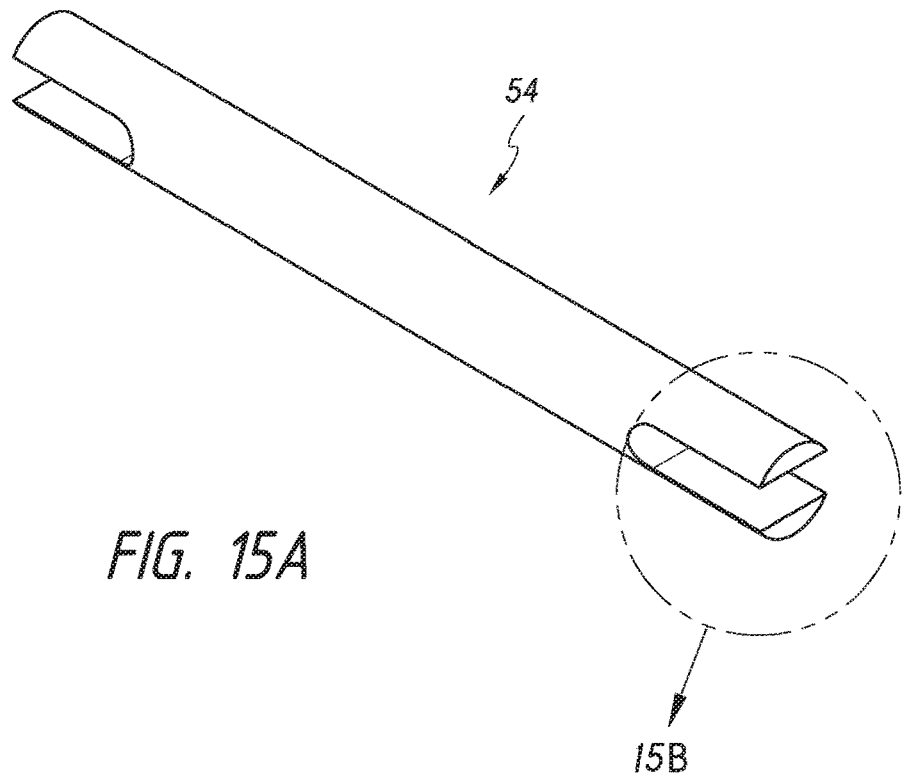
FIGS. 15A-15D depict a shunt having a longitudinal slit at a distal and/or proximal end.
Figure 15B:
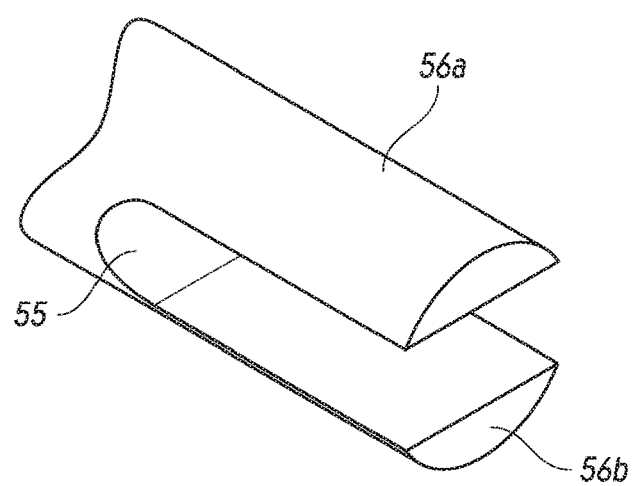
Figure 15C:
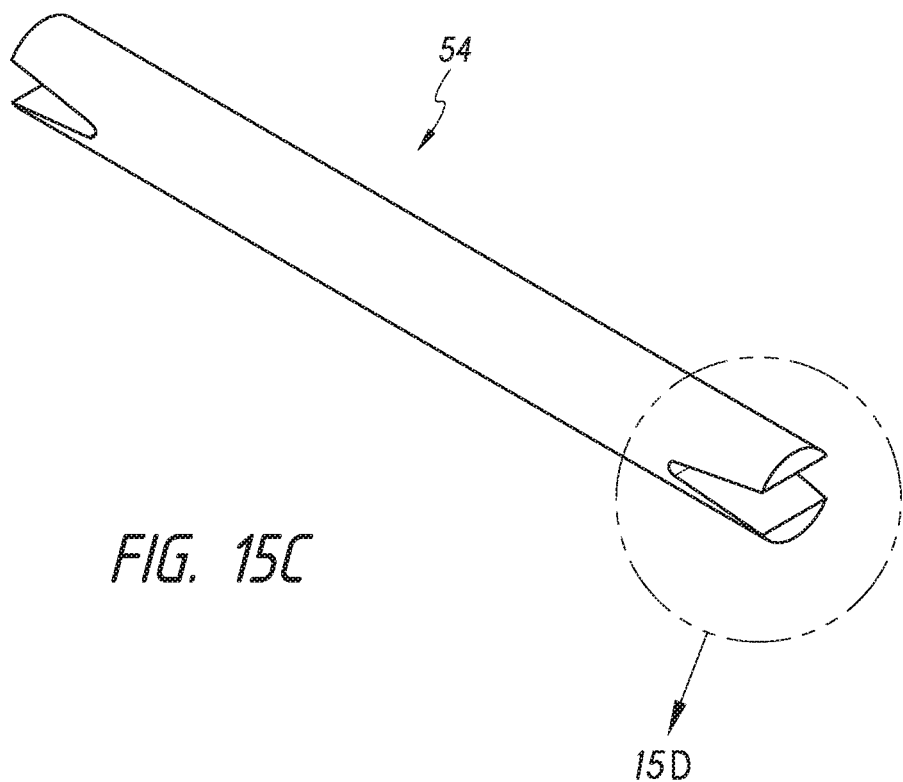
Figure 15D:
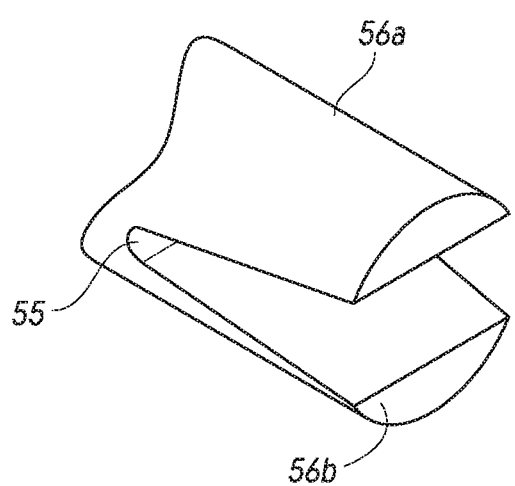
Figure 18C:
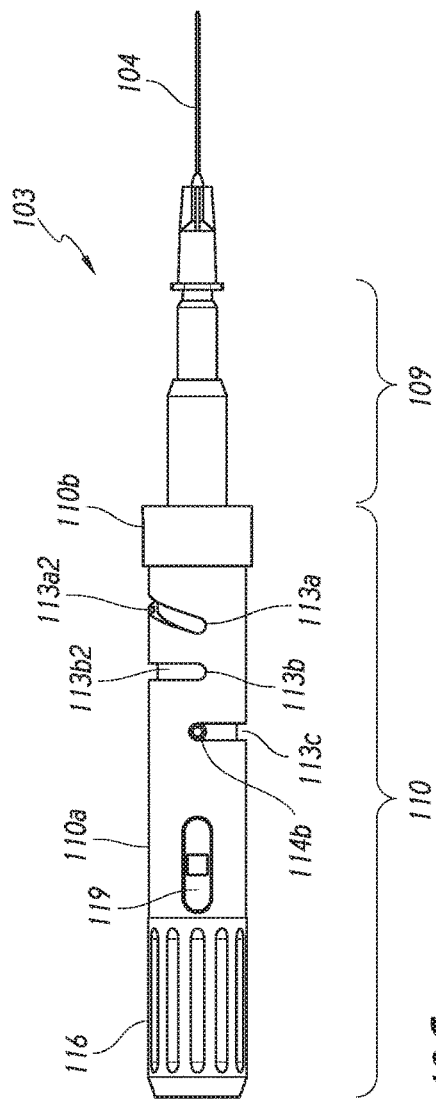
Figure 18D:
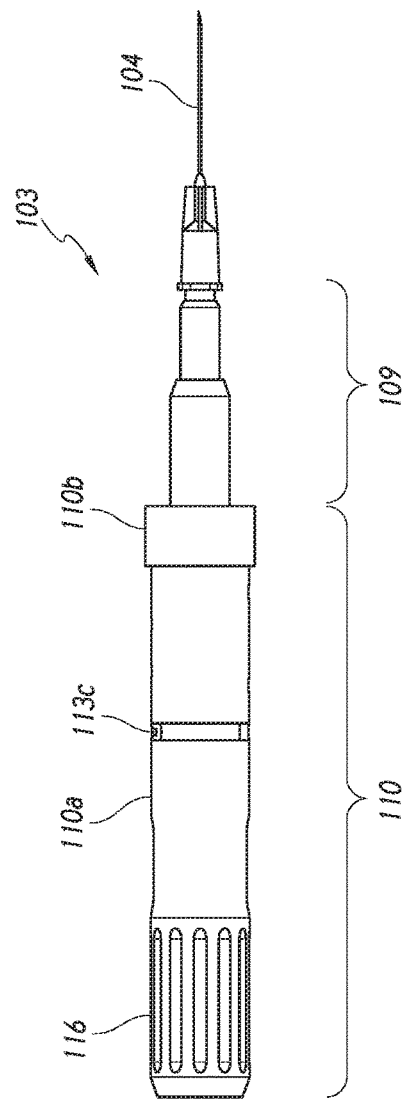

Longitudinal slit 55 can have any shape (i.e., width, length, height). FIGS. 15A and 15B show a longitudinal slit 55 that is straight such that the space between the top portion 56a and the bottom portion 56b remains the same along the length of the slit 55. In another embodiment shown in FIGS. 15C-15D, longitudinal slit 55 is tapered. In this embodiment, the space between the top portion 45a and the bottom portion 56b increases toward a proximal and/or distal end of the shunt 54.

Some embodiments encompass shunts of different shapes and different dimensions, and the shunts of some embodiments may be any shape or any dimension that may be accommodated by the eye. In certain embodiments, the intraocular shunt is of a cylindrical shape and has an outside cylindrical wall and a hollow interior. The shunt may have an inside diameter from approximately 10 μm to approximately 250 μm, an outside diameter from approximately 100 μm to approximately 450 μm, and a length from approximately 2 mm to approximately 10 mm. Shunts of some embodiments may be made from any biocompatible material. An exemplary material is gelatin. Methods of making shunts composed of gelatin are described above.

Pharmaceutical Agents

In certain embodiments, shunts of some embodiments may be coated or impregnated with at least one pharmaceutical and/or biological agent or a combination thereof. The pharmaceutical and/or biological agent may coat or impregnate an entire exterior of the shunt, an entire interior of the shunt, or both. Alternatively, the pharmaceutical or biological agent may coat and/or impregnate a portion of an exterior of the shunt, a portion of an interior of the shunt, or both. Methods of coating and/or impregnating an intraocular shunt with a pharmaceutical and/or biological agent are known in the art. See for example, Darouiche (U.S. Pat. Nos. 7,790, 183; 6,719,991; 6,558,686; 6,162,487; 5,902,283; 5,853, 745; and 5,624,704) and Yu et al. (U.S. patent application serial number 2008/0108933). The content of each of these references is incorporated by reference herein its entirety.

In certain embodiments, the exterior portion of the shunt that resides in the anterior chamber after implantation (e.g., about 1 mm of the proximal end of the shunt) is coated and/or impregnated with the pharmaceutical or biological agent. In other embodiments, the exterior of the shunt that resides in the scleral tissue after implantation of the shunt is coated and/or impregnated with the pharmaceutical or biological agent. In other embodiments, the exterior portion of the shunt that resides in the intrascleral space after implantation is coated and/or impregnated with the pharmaceutical or biological agent. In embodiments in which the pharmaceutical or biological agent coats and/or impregnates the interior of the shunt, the agent may be flushed through the shunt and into the area of lower pressure (e.g., the intrascleral space).

Any pharmaceutical and/or biological agent or combination thereof may be used with shunts of some embodiments. The pharmaceutical and/or biological agent may be released over a short period of time (e.g., seconds) or may be released over longer periods of time (e.g., days, weeks, months, or even years). Exemplary agents include anti-mitotic pharmaceuticals such as Mitomycin-C or 5-Fluorouracil, anti-VEGF (such as Lucintes, Macugen, Avastin, VEGF or steroids).

Deployment Devices

Deployment into the eye of an intraocular shunt according to some embodiments can be achieved using a hollow shaft configured to hold the shunt, as described herein. The hollow shaft can be coupled to a deployment device or part of the deployment device itself. Deployment devices that are suitable for deploying shunts according to some embodiments include but are not limited to the deployment devices described in U.S. Pat. No. 6,007,511, U.S. Pat. No. 6,544,249, and U.S. Publication No. US2008/0108933, the contents of which are each incorporated herein by reference in their entireties. In other embodiments, the deployment devices are devices as described in co-pending and co-owned U.S. nonprovisional patent application Ser. No. 12/946,222 filed on Nov. 15, 2010, or deployment devices described in co-pending and co-owned U.S. nonprovisional patent application Ser. No. 12/946,645 filed on Nov. 15, 2010, the entire content of each of which is incorporated by reference herein.

A shunt deployment device, such as those disclosed herein, can be used to implant the shunt in accordance with a variety of potential procedures, which can be modified or updated, according to aspects of the disclosure herein, as well as future methodologies and device features. For example, as discussed and shown below with regard to FIGS. 52A-54E of copending U.S. patent application Ser. No. 14/317,676, filed on Jun. 27, 2014, the entirety of which is incorporated herein by reference, a shunt deployment device can be used to implant a shunt using a variety of different procedures. The deployment device can be manual or automatic and can include features of one or more of the devices discussed or mentioned herein.

In still other embodiments, the shunts according to some embodiments are deployed into the eye using the deployment device 100 depicted in FIG. 16. While FIG. 16 shows a handheld manually operated shunt deployment device, it will be appreciated that devices of some embodiments may be coupled with robotic systems and may be completely or partially automated. As shown in FIG. 16, deployment device 100 includes a generally cylindrical body or housing 101, however, the body shape of housing 101 could be other than cylindrical. Housing 101 may have an ergonomical shape, allowing for comfortable grasping by an operator. Housing 101 is shown with optional grooves 102 to allow for easier gripping by a surgeon.

According to some embodiments, the shunt can be advanced into the eye tissue at a rate of between about 0.15 mm/sec to about 0.85 mm/sec. Further, in some embodiments, the shunt can be advanced into the eye tissue at a rate of between about 0.25 mm/sec to about 0.65 mm/sec.

Housing 101 is shown having a larger proximal portion that tapers to a distal portion. The distal portion includes a hollow sleeve 105. The hollow sleeve 105 is configured for insertion into an eye and to extend into an anterior chamber of an eye. The hollow sleeve is visible within an anterior chamber of an eye. According to some embodiment, the sleeve 105 can provide a visual preview or guide for an operator as to placement of the proximal portion of the shunt within the anterior chamber of an eye, as discussed below with regard to FIGS. 52A-52E of copending U.S. patent application Ser. No. 14/317,676, filed on Jun. 27, 2014. The sleeve 105 can provide a visual reference point that may be used by an operator to hold device 100 steady during the shunt deployment process, thereby assuring optimal longitudinal placement of the shunt within the eye. The sleeve 105 may include an edge at a distal end that provides resistance feedback to an operator upon insertion of the deployment device 100 within an eye of a person. Upon advancement of the device 100 across an anterior chamber of the eye, the hollow sleeve 105 will eventually contact the sclera, providing resistance feedback to an operator that no further advancement of the device 100 is necessary. The edge of the sleeve 105, prevents the shaft 104 from accidentally being pushed too far through the sclera. A temporary guard 108 is configured to fit around sleeve 105 and extend beyond an end of sleeve 105. The guard is used during shipping of the device and protects an operator from a distal end of a hollow shaft 104 that extends beyond the end of the sleeve 105. The guard is removed prior to use of the device.

Housing 101 is open at its proximal end, such that a portion of a deployment mechanism 103 may extend from the proximal end of the housing 101. A distal end of housing 101 is also open such that at least a portion of a hollow shaft 104 may extend through and beyond the distal end of the housing 101. Housing 101 further includes a slot 106 through which an operator, such as a surgeon, using the device 100 may view an indicator 107 on the deployment mechanism 103.

Housing 101 may be made of any material that is suitable for use in medical devices. For example, housing 101 may be made of a lightweight aluminum or a biocompatible plastic material. Examples of such suitable plastic materials include polycarbonate and other polymeric resins such as DELRIN and ULTEM. In certain embodiments, housing 101 is made of a material that may be autoclaved, and thus allow for housing 101 to be re-usable. Alternatively, device 100, may be sold as a one-time-use device, and thus the material of the housing does not need to be a material that is autoclavable.

Housing 101 may be made of multiple components that connect together to form the housing. FIG. 17 shows an exploded view of deployment device 100. In this figure, housing 101, is shown having three components 101a, 101b, and 101c. The components are designed to screw together to form housing 101. FIGS. 18A-18D also show deployment mechanism 103. The housing 101 is designed such that deployment mechanism 103 fits within assembled housing 101. Housing 101 is designed such that components of deployment mechanism 103 are movable within housing 101.

FIGS. 18A-18D show different enlarged views of the deployment mechanism 103. Deployment mechanism 103 may be made of any material that is suitable for use in medical devices. For example, deployment mechanism 103 may be made of a lightweight aluminum or a biocompatible plastic material. Examples of such suitable plastic materials include polycarbonate and other polymeric resins such as DELRIN and ULTEM. In certain embodiments, deployment mechanism 103 is made of a material that may be autoclaved, and thus allow for deployment mechanism 103 to be re-usable. Alternatively, device 100 may be sold as a onetime-use device, and thus the material of the deployment mechanism does not need to be a material that is autoclavable.

Deployment mechanism 103 includes a distal portion 109 and a proximal portion 110. The deployment mechanism 103 is configured such that distal portion 109 is movable within proximal portion 110. More particularly, distal portion 109 is capable of partially retracting to within proximal portion 110.

In this embodiment, the distal portion 109 is shown to taper to a connection with a hollow shaft 104. This embodiment is illustrated such that the connection between the hollow shaft 104 and the distal portion 109 of the deployment mechanism 103 occurs inside the housing 101. In other embodiments, the connection between hollow shaft 104 and the proximal portion 109 of the deployment mechanism 103 may occur outside of the housing 101. Hollow shaft 104 may be removable from the distal portion 109 of the deployment mechanism 103. Alternatively, the hollow shaft 104 may be permanently coupled to the distal portion 109 of the deployment mechanism 103.

Generally, hollow shaft 104 is configured to hold an intraocular shunt, such as the intraocular shunts according to some embodiments. The shaft 104 may be any length. A usable length of the shaft may be anywhere from about 5 mm to about 40 mm, and is 15 mm in certain embodiments. In certain embodiments, the shaft is straight. In other embodiments, shaft is of a shape other than straight, for example a shaft having a bend along its length.

A proximal portion of the deployment mechanism includes optional grooves 116 to allow for easier gripping by an operator for easier rotation of the deployment mechanism, which will be discussed in more detail below. The proximal portion 110 of the deployment mechanism also includes at least one indicator that provides feedback to an operator as to the state of the deployment mechanism. The indicator may be any type of indicator known in the art, for example a visual indicator, an audio indicator, or a tactile indicator. FIGS. 18A-18D shows a deployment mechanism having two indicators, a ready indicator 111 and a deployed indicator 119. Ready indicator 111 provides feedback to an operator that the deployment mechanism is in a configuration for deployment of an intraocular shunt from the deployment device 100. The ready indicator 111 is shown in this embodiment as a green oval having a triangle within the oval. Deployed indicator 119 provides feedback to the operator that the deployment mechanism has been fully engaged and has deployed the shunt from the deployment device 100. The deployed indicator 119 is shown in this embodiment as a yellow oval having a black square within the oval. The indicators are located on the deployment mechanism such that when assembled, the indicators 111 and 119 may be seen through slot 106 in housing 101.

Figure 19A:
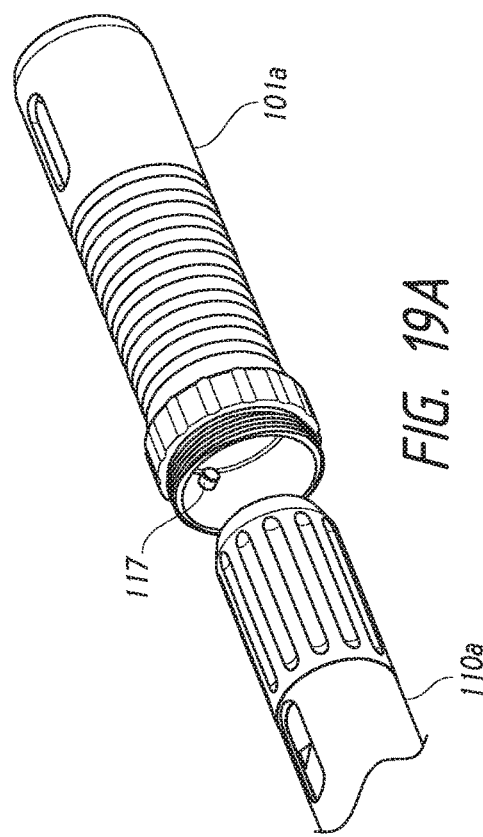
FIGS. 19A-19C are schematics showing interaction of the deployment mechanism with a portion of the housing of the deployment device.
Figure 19B:
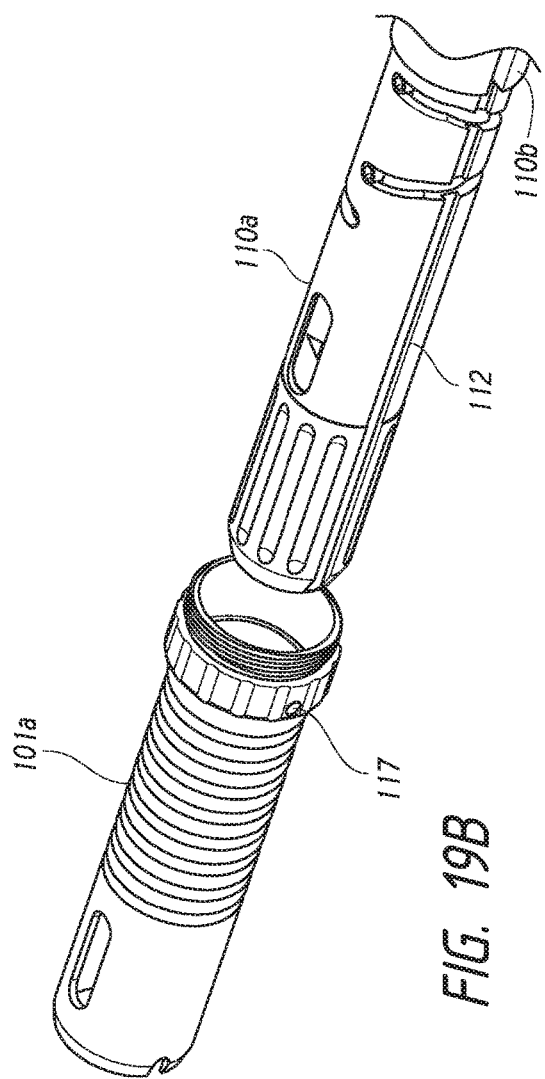
Figure 19C:
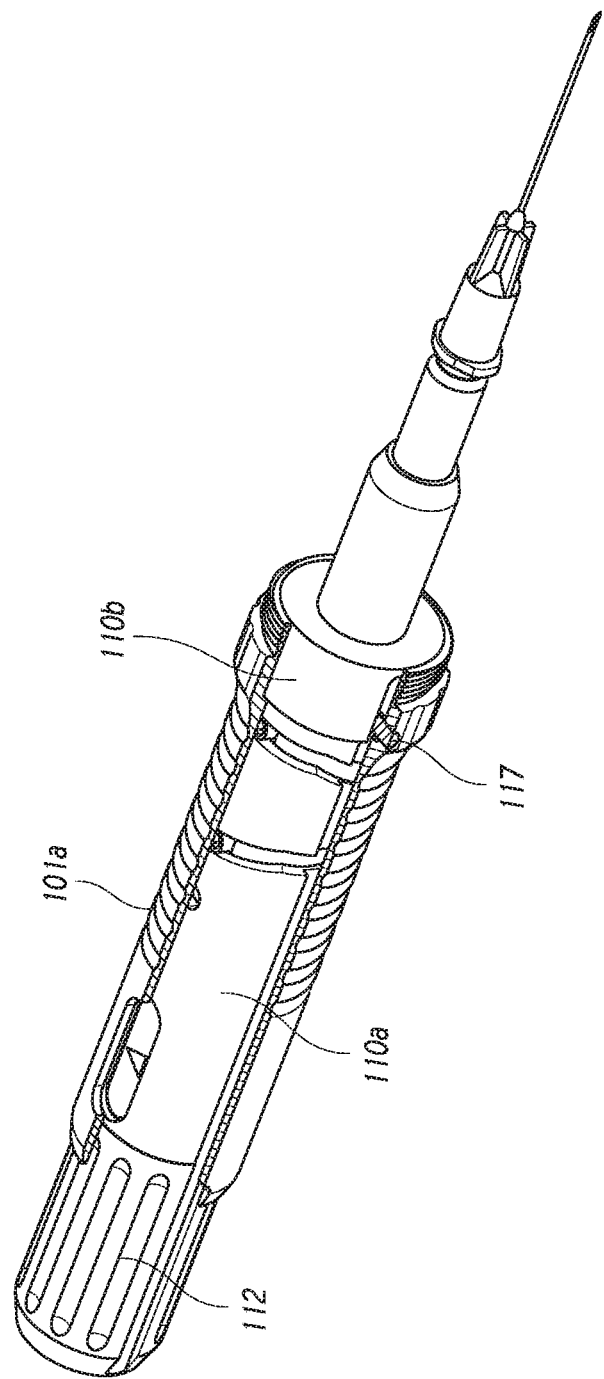

The proximal portion 110 includes a stationary portion 110b and a rotating portion 110a. The proximal portion 110 includes a channel 112 that runs part of the length of stationary portion 110b and the entire length of rotating portion 110a. The channel 112 is configured to interact with a protrusion 117 on an interior portion of housing component 101a (FIGS. 19A and 19B). During assembly, the protrusion 117 on housing component 101a is aligned with channel 112 on the stationary portion 110b and rotating portion 110a of the deployment mechanism 103. The proximal portion 110 of deployment mechanism 103 is slid within housing component 101a until the protrusion 117 sits within stationary portion 110b (FIG. 19C). Assembled, the protrusion 117 interacts with the stationary portion 110b of the deployment mechanism 103 and prevents rotation of stationary portion 110b. In this configuration, rotating portion 110a is free to rotate within housing component 101a.

Referring back to FIGS. 18A-18D, the rotating portion 110a of proximal portion 110 of deployment mechanism 103 also includes channels 113a, 113b, and 113c. Channel 113a includes a first portion 113a1 that is straight and runs perpendicular to the length of the rotating portion 110a, and a second portion 113a2 that runs diagonally along the length of rotating portion 110a, downwardly toward a proximal end of the deployment mechanism 103. Channel 113b includes a first portion 113b1 that runs diagonally along the length of the rotating portion 110a, downwardly toward a distal end of the deployment mechanism 103, and a second portion that is straight and runs perpendicular to the length of the rotating portion 110a. The point at which first portion 113a1 transitions to second portion 113a2 along channel 113a, is the same as the point at which first portion 113b1 transitions to second portion 113b2 along channel 113b. Channel 113c is straight and runs perpendicular to the length of the rotating portion 110a. Within each of channels 113a, 113b, and 113c, sit members 114a, 114b, and 114c respectively. Members 114a, 114b, and 114c are movable within channels 113a, 113b, and 113c. Members 114a, 114b, and 114c also act as stoppers that limit movement of rotating portion 110a, which thereby limits axial movement of the shaft 104.

Figure 20:
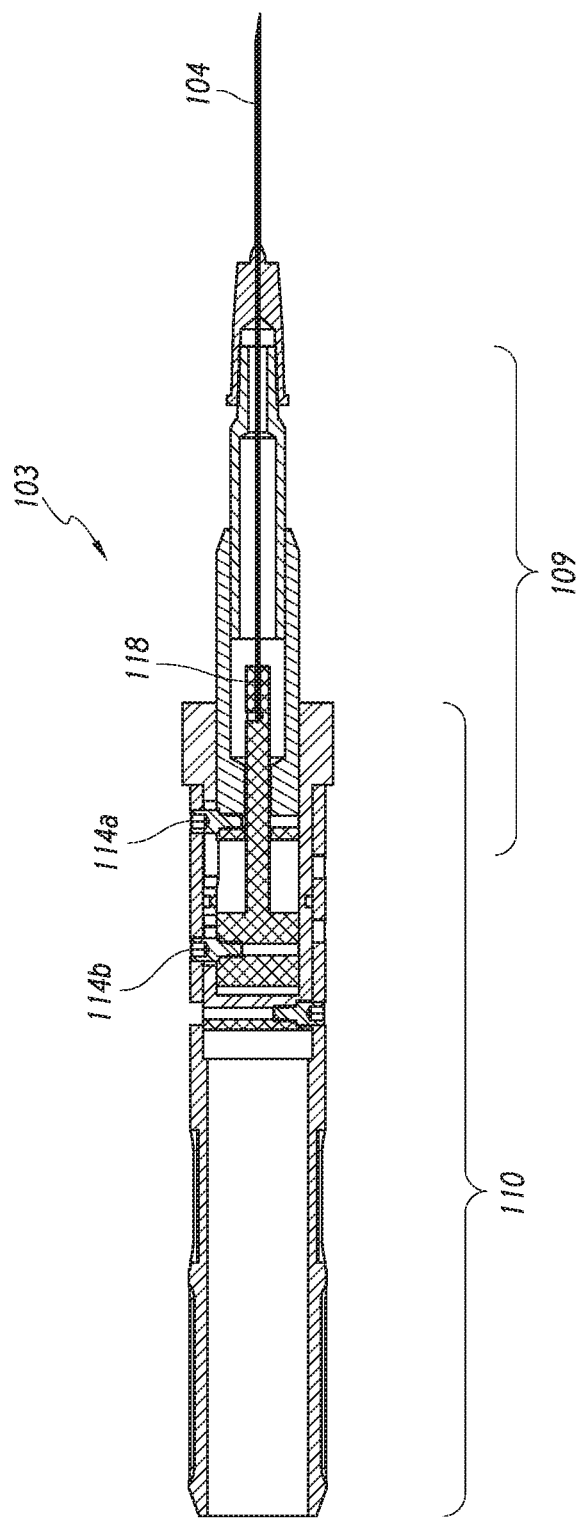
FIG. 20 shows a cross sectional view of the deployment mechanism of the deployment device.
Figure 24:
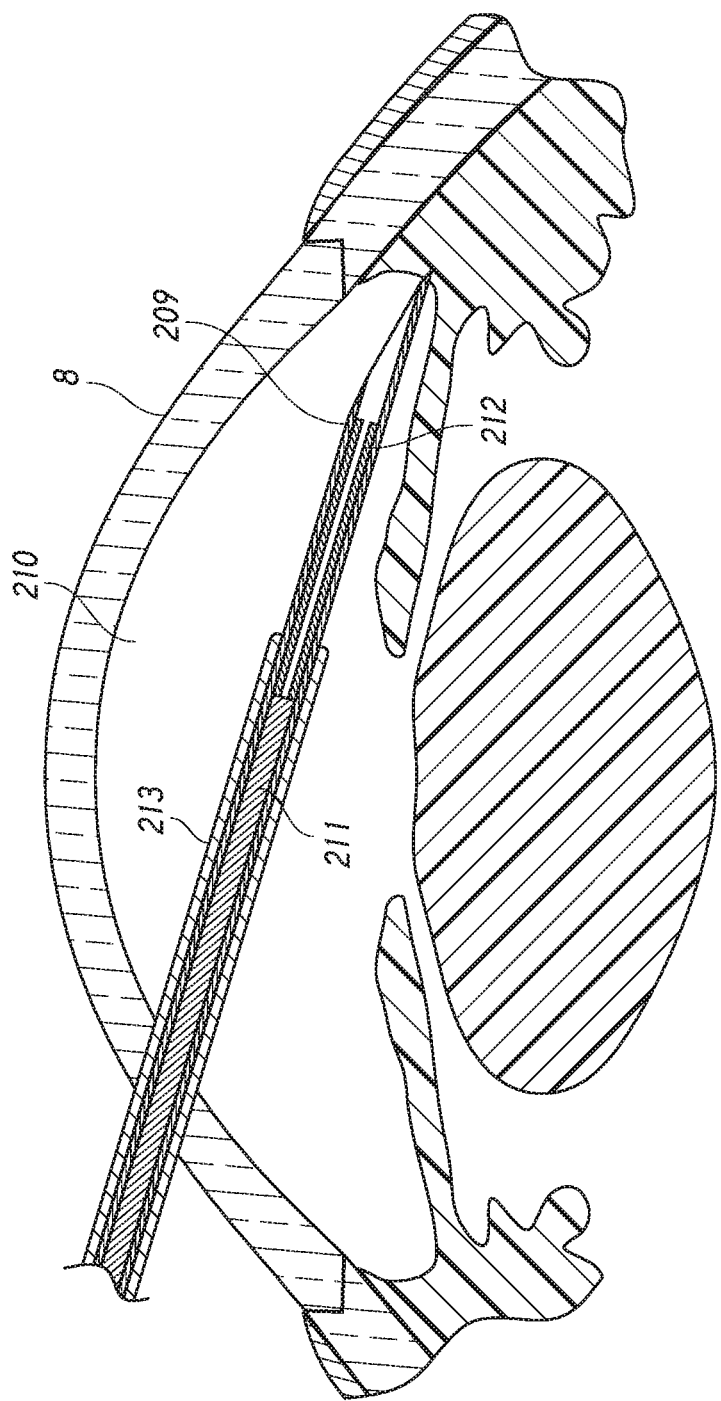
FIGS. 24-31 depict a sequence for ab interno shunt placement, according to some embodiments.

FIG. 20 shows a cross-sectional view of deployment mechanism 103. Member 114a is connected to the distal portion 109 of the deployment mechanism 103. Movement of member 114a results in retraction of the distal portion 109 of the deployment mechanism 103 to within the proximal portion 110 of the deployment mechanism 103. Member 114b is connected to a pusher component 118. The pusher component 118 extends through the distal portion 109 of the deployment mechanism 103 and extends into a portion of hollow shaft 104. The pusher component is involved in deployment of a shunt from the hollow shaft 104. An exemplary pusher component is a plunger. Movement of member 114b engages pusher 118 and results in pusher 118 advancing within hollow shaft 104.

Reference is now made to FIGS. 21A-23D, which accompany the following discussion regarding deployment of a shunt 115 from deployment device 100. FIG. 21A shows deployment device 100 in a pre-deployment configuration. In this configuration, shunt 115 is loaded within hollow shaft 104 (FIG. 21C). As shown in FIG. 21C, shunt 115 is only partially within shaft 104, such that a portion of the shunt is exposed. However, the shunt 115 does not extend beyond the end of the shaft 104. In other embodiments, the shunt 115 is completely disposed within hollow shaft 104. The shunt 115 is loaded into hollow shaft 104 such that the shunt abuts pusher component 118 within hollow shaft 104. A distal end of shaft 104 is beveled to assist in piercing tissue of the eye.

Additionally, in the pre-deployment configuration, a portion of the shaft 104 extends beyond the sleeve 105 (FIG. 21C). The deployment mechanism is configured such that member 114a abuts a distal end of the first portion 113a1 of channel 113a, and member 114b abut a proximal end of the first portion 113b1 of channel 113b (FIG. 21B). In this configuration, the ready indicator 111 is visible through slot 106 of the housing 101, providing feedback to an operator that the deployment mechanism is in a configuration for deployment of an intraocular shunt from the deployment device 100 (FIG. 21A). In this configuration, the device 100 is ready for insertion into an eye (insertion configuration or pre-deployment configuration). Methods for inserting and implanting shunts are discussed in further detail below.

Once the device has been inserted into the eye and advanced to a location to where the shunt will be deployed, the shunt 115 may be deployed from the device 100. The deployment mechanism 103 is a two-stage system. The first stage is engagement of the pusher component 118 and the second stage is retraction of the distal portion 109 to within the proximal portion 110 of the deployment mechanism 103. Rotation of the rotating portion 110a of the proximal portion 110 of the deployment mechanism 103 sequentially engages the pusher component and then the retraction component.

In the first stage of shunt deployment, the pusher component is engaged and the pusher partially deploys the shunt from the deployment device. During the first stage, rotating portion 110a of the proximal portion 110 of the deployment mechanism 103 is rotated, resulting in movement of members 114a and 114b along first portions 113a1 and 113b1 in channels 113a and 113b. Since the first portion 113a1 of channel 113a is straight and runs perpendicular to the length of the rotating portion 110a, rotation of rotating portion 110a does not cause axial movement of member 114a. Without axial movement of member 114a, there is no retraction of the distal portion 109 to within the proximal portion 110 of the deployment mechanism 103. Since the first portion 113b1 of channel 113b runs diagonally along the length of the rotating portion 110a, upwardly toward a distal end of the deployment mechanism 103, rotation of rotating portion 110a causes axial movement of member 114b toward a distal end of the device. Axial movement of member 114b toward a distal end of the device results in forward advancement of the pusher component 118 within the hollow shaft 104. Such movement of pusher component 118 results in partially deployment of the shunt 115 from the shaft 104.

FIGS. 22A-22C show schematics of the deployment mechanism at the end of the first stage of deployment of the shunt from the deployment device. As is shown FIG. 22A, members 114a and 114b have finished traversing along first portions 113a1 and 113b1 of channels 113a and 113b. Additionally, pusher component 118 has advanced within hollow shaft 104 (FIG. 22B), and shunt 115 has been partially deployed from the hollow shaft 104 (FIG. 22C). As is shown in these figures, a portion of the shunt 115 extends beyond an end of the shaft 104.

In the second stage of shunt deployment, the retraction component is engaged and the distal portion of the deployment mechanism is retracted to within the proximal portion of the deployment mechanism, thereby completing deployment of the shunt from the deployment device. During the second stage, rotating portion 110a of the proximal portion 110 of the deployment mechanism 103 is further rotated, resulting in movement of members 114a and 114b along second portions 113a2 and 113b2 in channels 113a and 113b. Since the second portion 113b2 of channel 113b is straight and runs perpendicular to the length of the rotating portion 110a, rotation of rotating portion 110a does not cause axial movement of member 114b. Without axial movement of member 114b, there is no further advancement of pusher 118. Since the second portion 113a2 of channel 113a runs diagonally along the length of the rotating portion 110a, downwardly toward a proximal end of the deployment mechanism 103, rotation of rotating portion 110a causes axial movement of member 114a toward a proximal end of the device. Axial movement of member 114a toward a proximal end of the device results in retraction of the distal portion 109 to within the proximal portion 110 of the deployment mechanism 103. Retraction of the distal portion 109, results in retraction of the hollow shaft 104. Since the shunt 115 abuts the pusher component 118, the shunt remains stationary as the hollow shaft 104 retracts from around the shunt 115 (FIG. 22C). The shaft 104 retracts almost completely to within the sleeve 105. During both stages of the deployment process, the sleeve 105 remains stationary and in a fixed position.

FIGS. 23A-23D show schematics of the device 100 after deployment of the shunt 115 from the device 100. FIG. 23B shows a schematic of the deployment mechanism at the end of the second stage of deployment of the shunt from the deployment device. As is shown in FIG. 23B, members 114a and 114b have finished traversing along second portions 113a2 and 113b2 of channels 113a and 113b. Additionally, distal portion 109 has retracted to within proximal portion 110, thus resulting in retraction of the hollow shaft 104 to within the sleeve 105. FIG. 23D shows an enlarged view of the distal portion of the deployment device after deployment of the shunt. This figure shows that the hollow shaft 104 is not fully retracted to within the sleeve 105 of the deployment device 100. However, in certain embodiments, the shaft 104 may completely retract to within the sleeve 105.

Additional Methods for Intrascleral Shunt Placement

Some embodiments of the methods disclosed herein can involve creating an opening in the sclera (e.g., by piercing the sclera with a delivery device), and positioning a shunt in the anterior chamber of the eye such that the shunt terminates adjacent an opening formed in the sclera. In some embodiments, such placement can permit flow through the shunt to reach the intrascleral space, thereby facilitating fluid flow through both the opening and the intrascleral space. The outlet of the shunt may be positioned in different places within the intrascleral space. For example, the outlet of the shunt may be positioned within the sclera (e.g., within deep and superficial layers or tissue of the sclera). Alternatively, the outlet of the shunt may be positioned such that the outlet is even with or superficial to the opening through the sclera.

Methods of implanting intraocular shunts are known in the art. Shunts may be implanted using an ab externo approach (entering through the conjunctiva and inwards through the sclera) or an ab interno approach (entering through the cornea, across the anterior chamber, through the trabecular meshwork and sclera). The deployment device may be any device that is suitable for implanting an intraocular shunt into an eye. Such devices generally include a shaft connected to a deployment mechanism. In some devices, a shunt is positioned over an exterior of the shaft and the deployment mechanism works to deploy the shunt from an exterior of the shaft. In other devices, the shaft is hollow and the shunt is at least partially disposed in the shaft. In those devices, the deployment mechanism works to deploy the shunt from within the shaft. Depending on the device, a distal portion of the shaft may be sharpened or blunt, or straight or curved.

Ab-Interno Approach

Ab interno approaches for implanting an intraocular shunt in the subconjunctival space are shown for example in Yu et al. (U.S. Pat. No. 6,544,249 and U.S. Patent Publication No. 2008/0108933) and Prywes (U.S. Pat. No. 6,007,511), the contents of each of which are incorporated by reference herein in its entirety. An exemplary ab-interno method employs a transpupil approach and involves creating a first opening in the sclera of an eye, advancing a shaft configured to hold an intraocular shunt across an anterior chamber of an eye and through the sclera to create a second opening in the sclera, retracting the shaft through the second opening to within the sclera (i.e., the intrascleral space), deploying the shunt from the shaft such that the shunt forms a passage from the anterior chamber of the eye to the intrascleral space of the eye, such that an outlet of the shunt is positioned so that at least some of the fluid that exits the shunt flows through the second opening in the sclera, and withdrawing the shaft from the eye. The first opening in the sclera may be made in any manner. In certain embodiments, the shaft creates the first opening in the sclera. In other embodiments, a tool other than the shaft creates the first opening in the sclera.

In certain embodiments, some embodiments of the methods disclosed herein can generally involve inserting into the eye a hollow shaft configured to hold an intraocular shunt. In certain embodiments, the hollow shaft is a component of a deployment device that may deploy the intraocular shunt. The shunt is then deployed from the shaft into the eye such that the shunt forms a passage from the anterior chamber into the sclera (i.e., the intrascleral space). The hollow shaft is then withdrawn from the eye.

Figure 25:
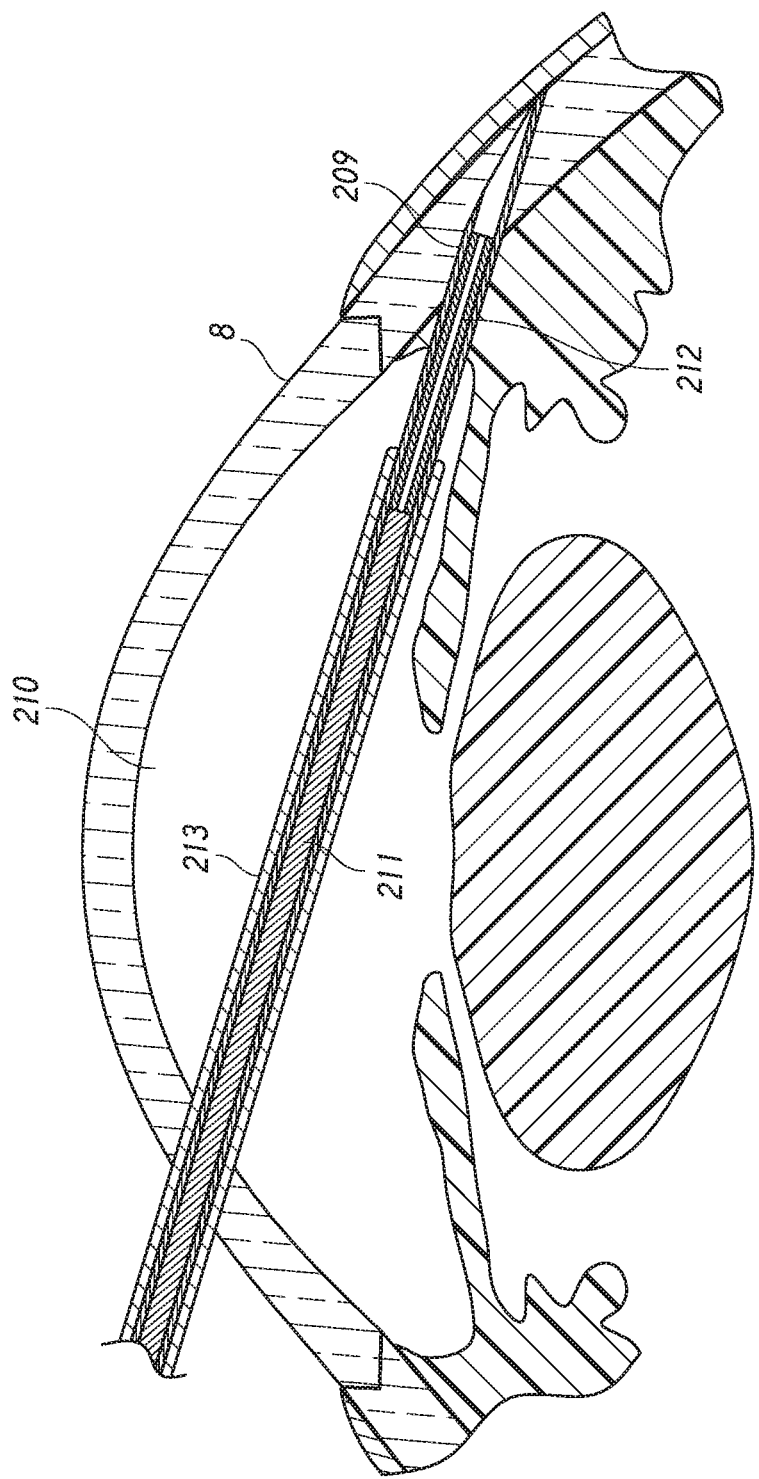
Figure 26:
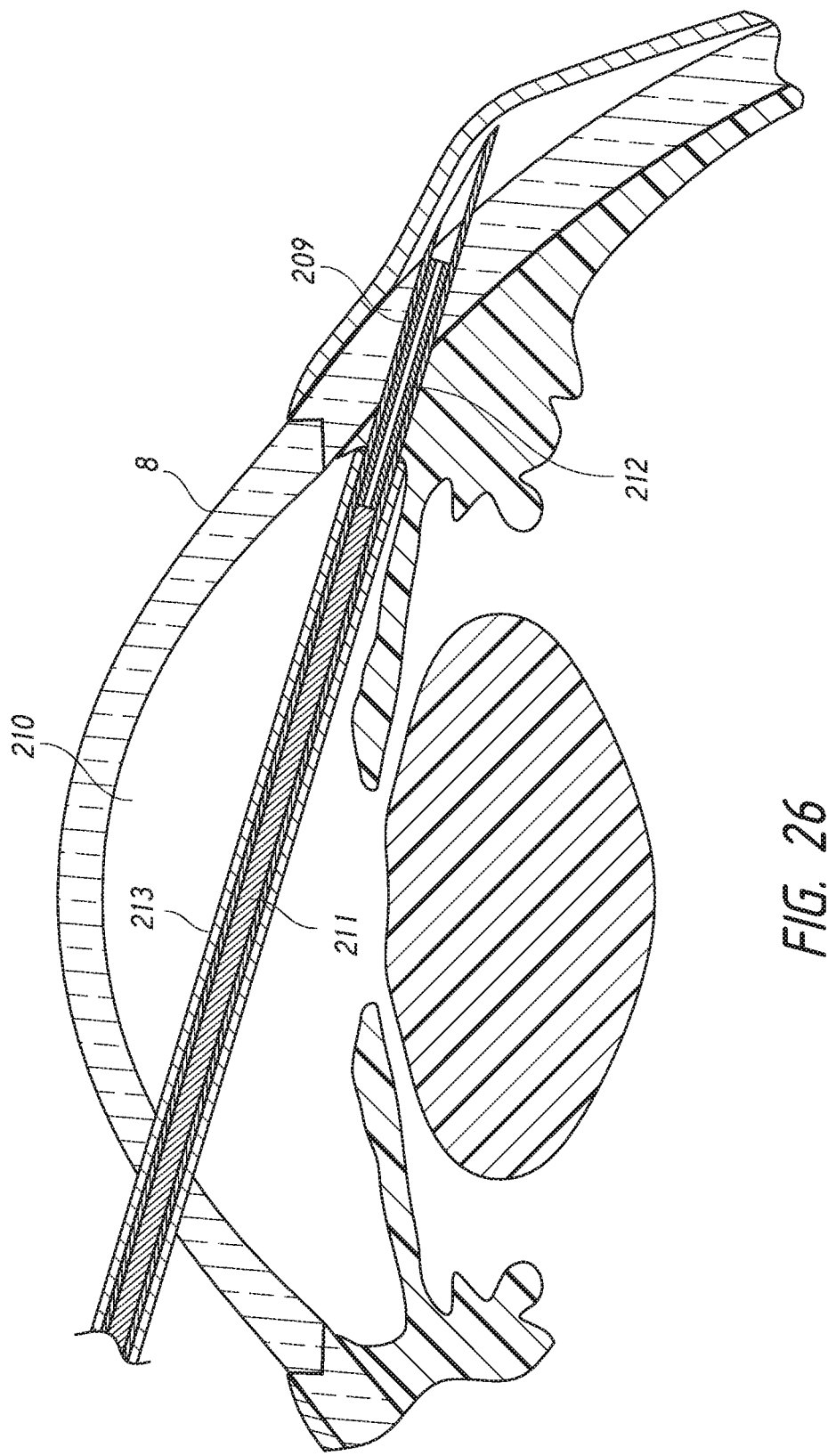
Figure 27:
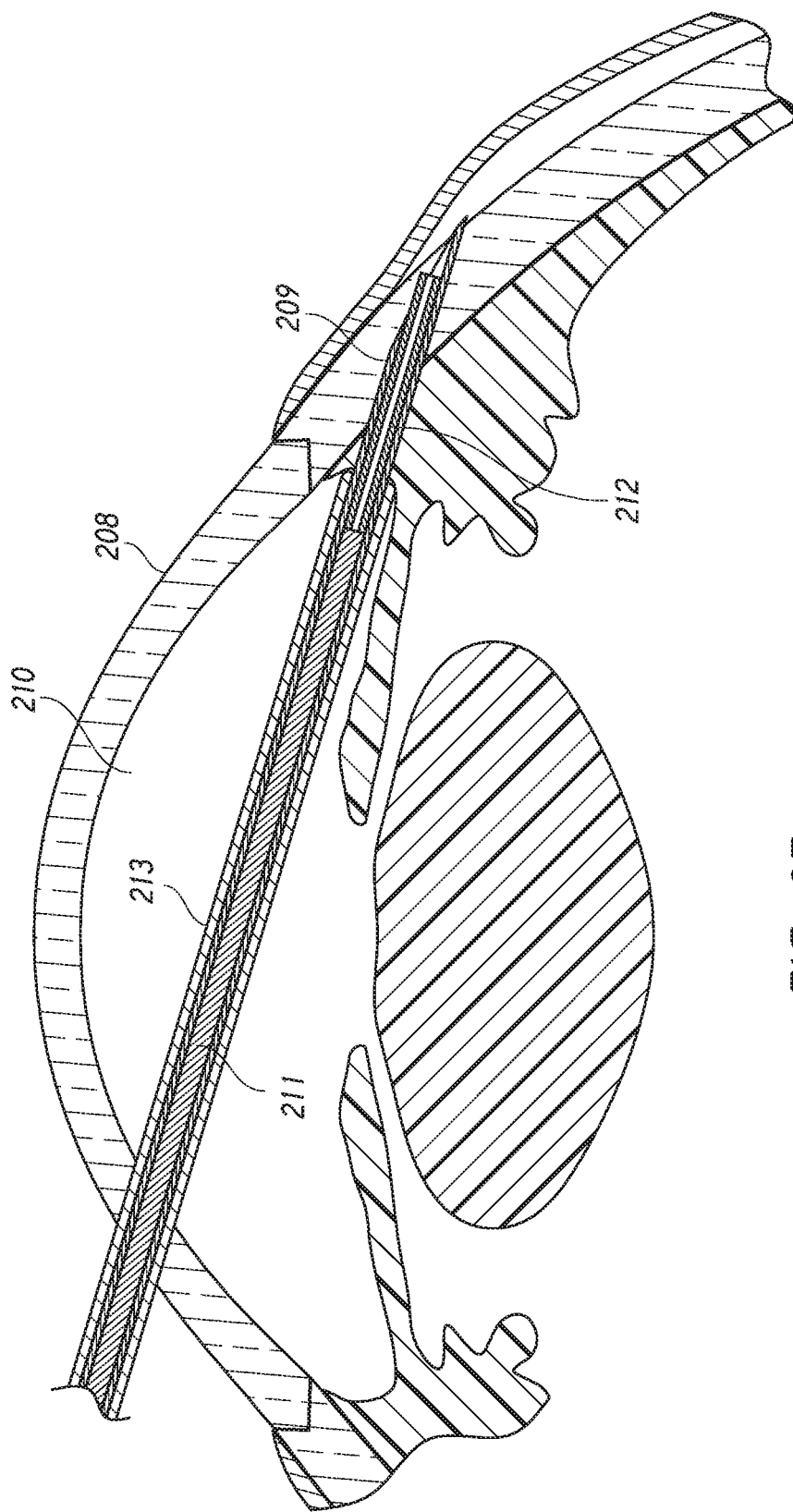
Figure 28:
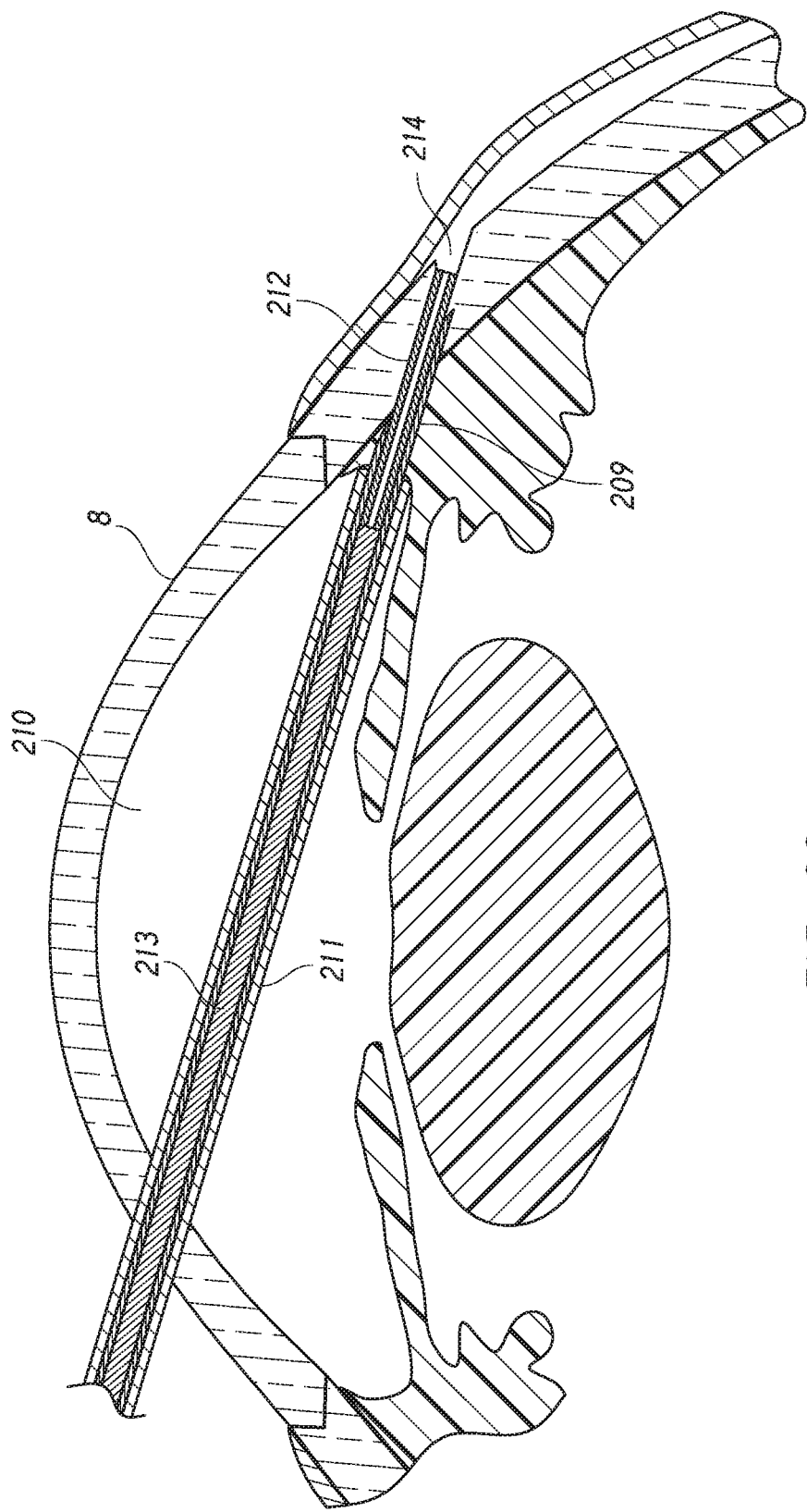
Figure 29:
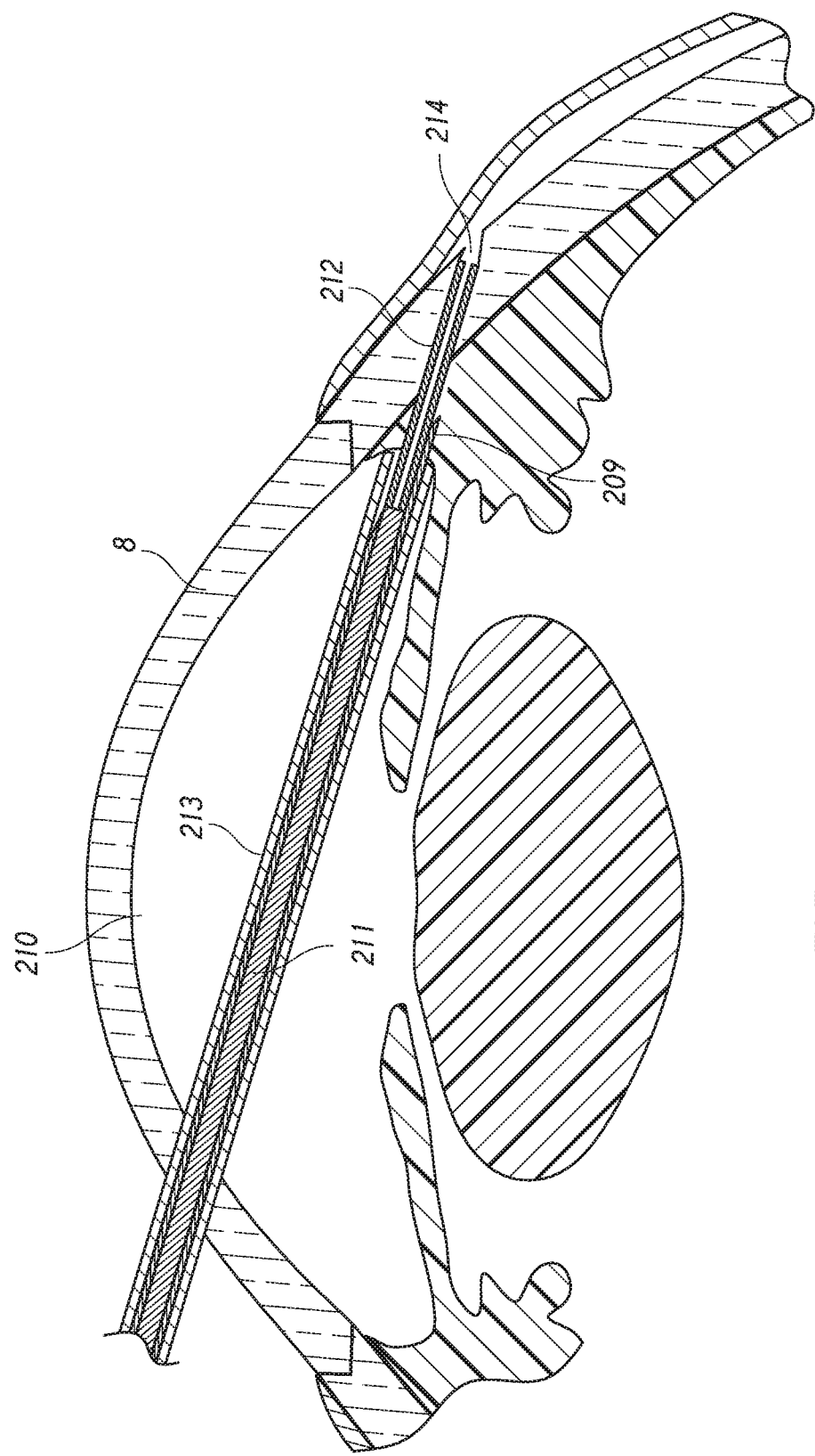
Figure 30:
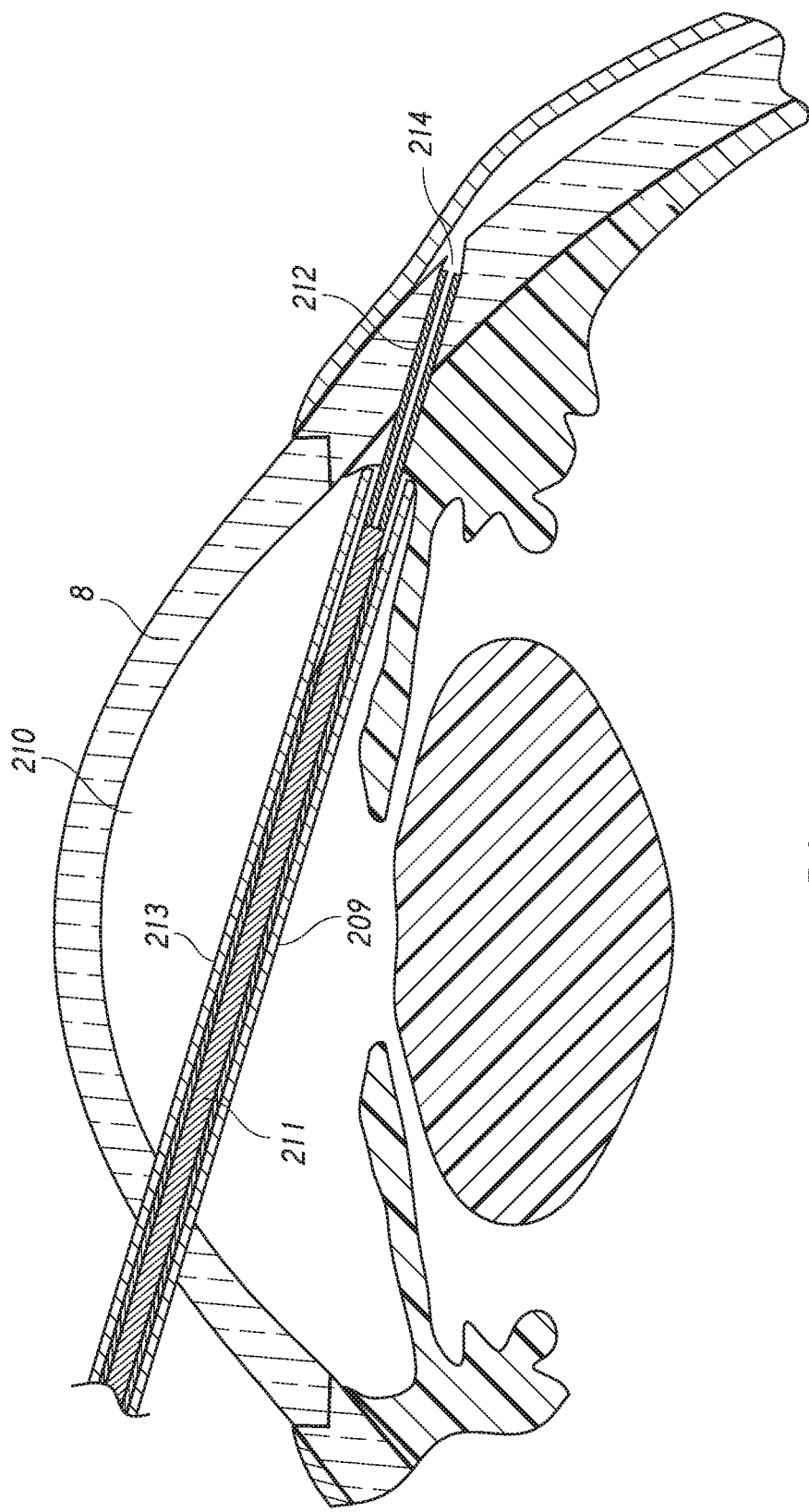
Figure 31:
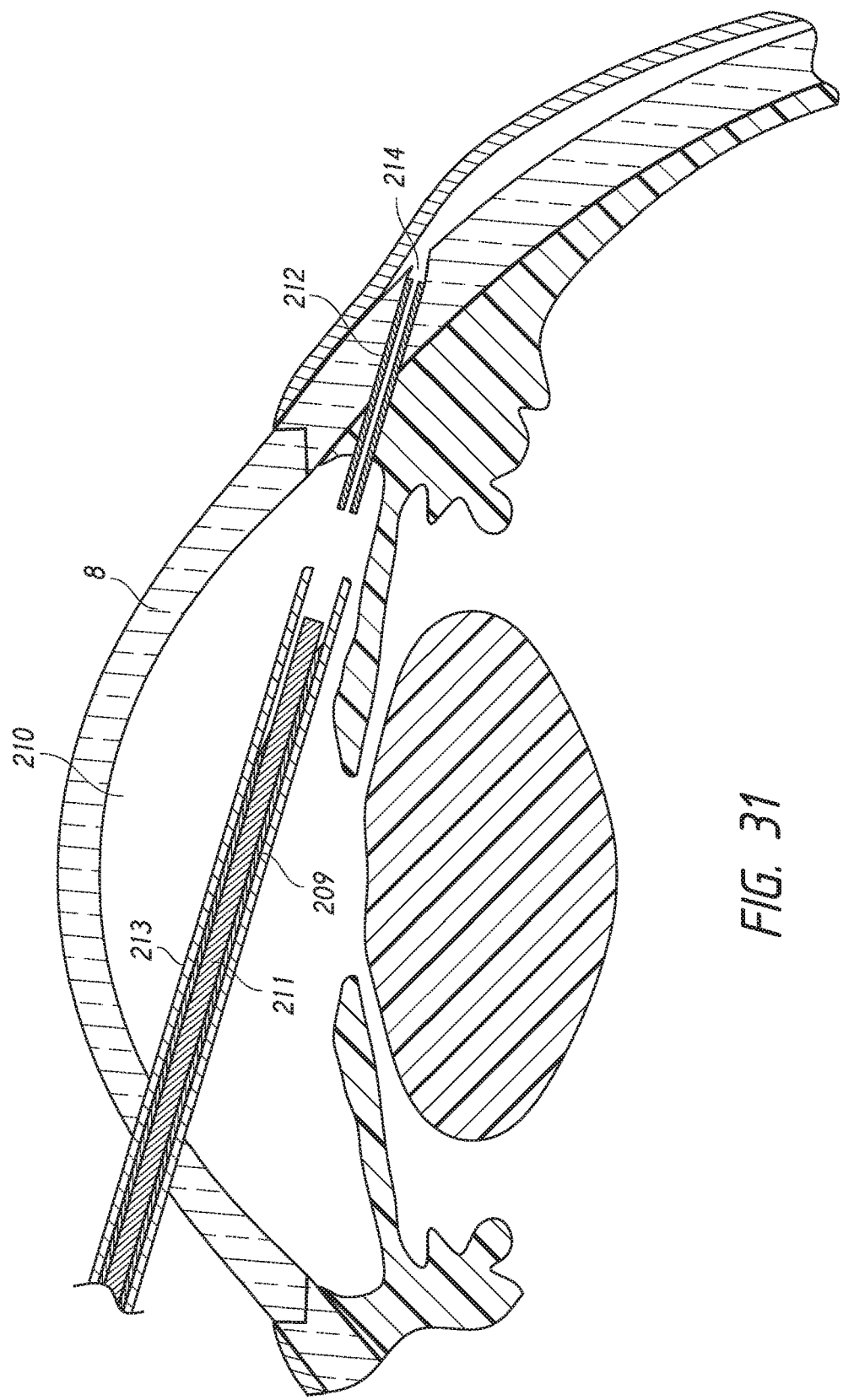

To place the shunt within the eye, a surgical intervention to implant the shunt is performed that involves inserting into the eye a deployment device that holds an intraocular shunt, and deploying at least a portion of the shunt within intrascleral space. FIGS. 24-31 provide an exemplary sequence for ab interno shunt placement. In certain embodiments, a hollow shaft 209 of a deployment device holding the shunt 212 enters the eye through the cornea (ab interno approach, FIG. 24). The shaft 209 is advanced across the anterior chamber 210 in what is referred to as a transpupil implant insertion. The shaft 209 is advanced through the anterior angle tissues of the eye and into the sclera 8 and further advanced until it passes through the sclera 8, thereby forming a second opening in the sclera 8 (FIGS. 25-26). Once the second opening in the sclera 8 is achieved, the shaft 209 is retracted all the way back through the sclera 8 and into the anterior chamber 210 of the eye (FIGS. 27-30). During this shaft retraction, the shunt 212 is held in place by a plunger rod 211 that is positioned behind the proximal end of the shunt 212. After the shaft 209 has been completely withdrawn from the sclera 8, the plunger rod 211 is withdrawn as well and the shunt implantation sequence is complete (FIG. 31). This process results in an implanted shunt 212 in which a distal end of the shunt 212 is proximate a passageway 214 through the sclera 8. Once fully deployed, a proximal end of shunt 212 resides in the anterior chamber 210 and a distal end of shunt 212 resides in the intrascleral space. Preferably a sleeve 213 is used around the shaft 212 and designed in length such that the sleeve 213 acts as a stopper for the scleral penetration of the shaft and also determines the longitudinal placement of the proximal end of the shunt.

Insertion of the shaft of the deployment device into the sclera 8 produces a long scleral channel of about 2 mm to about 5 mm in length. Withdrawal of the shaft of the deployment device prior to deployment of the shunt 212 from the device produces a space in which the shunt 212 may be deployed. Deployment of the shunt 212 allows for aqueous humor 3 to drain into traditional fluid drainage channels of the eye (e.g., the intrascleral vein, the collector channel, Schlemm's canal, the trabecular outflow, and the uveoscleral outflow to the ciliary muscle. The deployment is performed such that an outlet of the shunt is positioned proximate the opening in the sclera so that at least some of the fluid that exits the shunt flows through the opening in the sclera, thereby ensuring that the intrascleral space does not become overwhelmed with fluid output from the shunt.

Preferably, some embodiments of the methods disclosed herein are conducted by making an incision in the eye prior to insertion of the deployment device. In some embodiments of the methods disclosed herein may be conducted without making an incision in the eye prior to insertion of the deployment device. In certain embodiments, the shaft that is connected to the deployment device has a sharpened point or tip. In certain embodiments, the hollow shaft is a needle. Exemplary needles that may be used are commercially available from Terumo Medical Corp. (Elkington Md.). In some embodiments, the needle has a hollow interior and a beveled tip, and the intraocular shunt is held within the hollow interior of the needle. In another embodiment, the needle has a hollow interior and a triple ground point or tip.

Some embodiments of the methods disclosed herein are preferably conducted without needing to remove an anatomical portion or feature of the eye, including but not limited to the trabecular meshwork, the iris, the cornea, or aqueous humor. Some embodiments of the methods disclosed herein are also preferably conducted without inducing substantial ocular inflammation, such as subconjunctival blebbing or endophthalmitis. Such methods can be achieved using an ab interno approach by inserting the hollow shaft configured to hold the intraocular shunt through the cornea, across the anterior chamber, through the trabecular meshwork and into the sclera. However, some embodiments of the methods disclosed herein may be conducted using an ab externo approach.

When some embodiments of the methods disclosed herein are conducted using an ab interno approach, the angle of entry through the cornea as well as the up and downward forces applied to the shaft during the scleral penetration affect optimal placement of the shunt in the intrascleral space. Preferably, the hollow shaft is inserted into the eye at an angle superficial to the corneal limbus, in contrast with entering through or deep to the corneal limbus. For example, the hollow shaft is inserted about 0.25 mm to about 3.0 mm, preferably about 0.5 mm to about 2.5 mm, more preferably about 1.0 mm to about 2.0 mm superficial to the corneal limbus, or any specific value within said ranges, e.g., about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm superficial to the corneal limbus.

Figure 32:
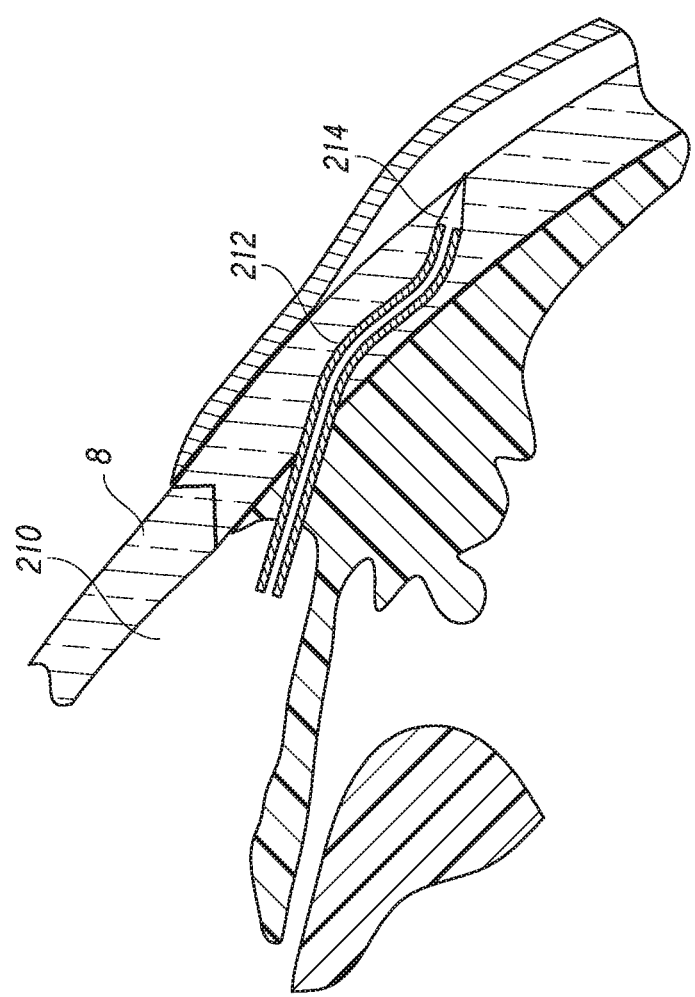
FIG. 32 depicts an implanted shunt in an S-shaped scleral passageway, according to some embodiments.

Without intending to be bound by any theory, placement of the shunt farther from the limbus at the exit site, as provided by an angle of entry superficial to the limbus, as well as an S-shaped scleral tunnel (FIG. 32) due to applied up or downward pressure during the scleral penetration of the shaft is believed to provide access to more lymphatic channels for drainage of aqueous humor, such as the episcleral lymphatic network, in addition to the conjunctival lymphatic system.

Ab Externo Approach

In other embodiments, an ab externo approach is employed. Ab externo implantation approaches are shown for example in Nissan et al. (U.S. Pat. No. 8,109,896), Tu et al. (U.S. Pat. No. 8,075,511), and Haffner et al. (U.S. Pat. No. 7,879,001), the content of each of which is incorporated by reference herein in its entirety. An exemplary ab externo approach avoids having to make a scleral flap. In this preferred embodiment, a distal end of the deployment device is used to make an opening into the eye and into the sclera. For example, a needle is inserted from ab externo through the sclera and exits the anterior angle of the eye. The needle is then withdrawn, leaving a scleral slit behind. A silicone tube with sufficient stiffness is then manually pushed through the scleral slit from the outside so that the distal tube ends distal to the Trabecular Meshwork in the anterior chamber of the eye. Towards the proximal end, the tube exits the sclera, lays on top of it, and connects on its proximal end to a plate that is fixated by sutures to the outside scleral surface far away (>10 mm) from the limbus.

Figure 33:
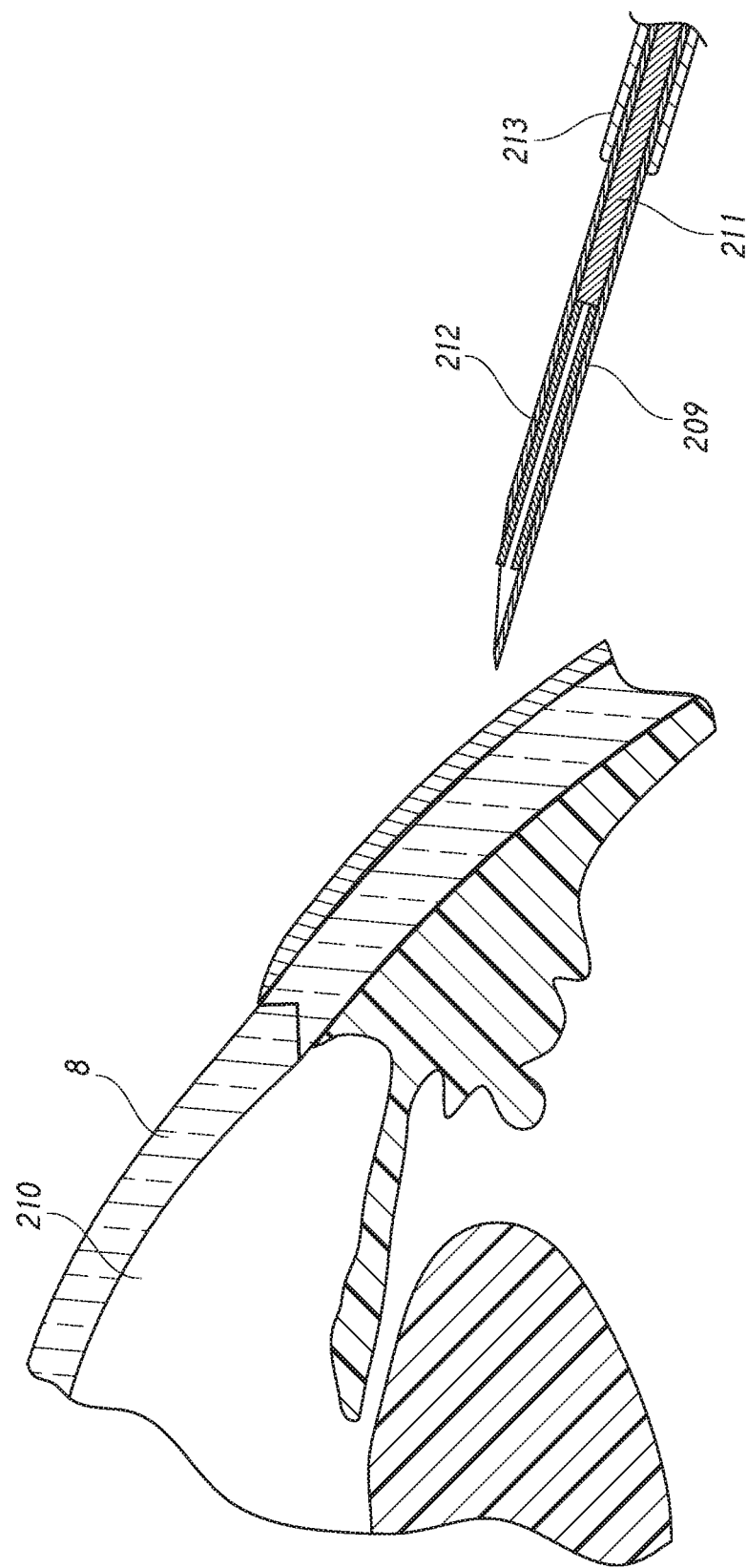
FIGS. 33-39 depict a sequence for ab externo shunt placement, according to some embodiments.
Figure 34:
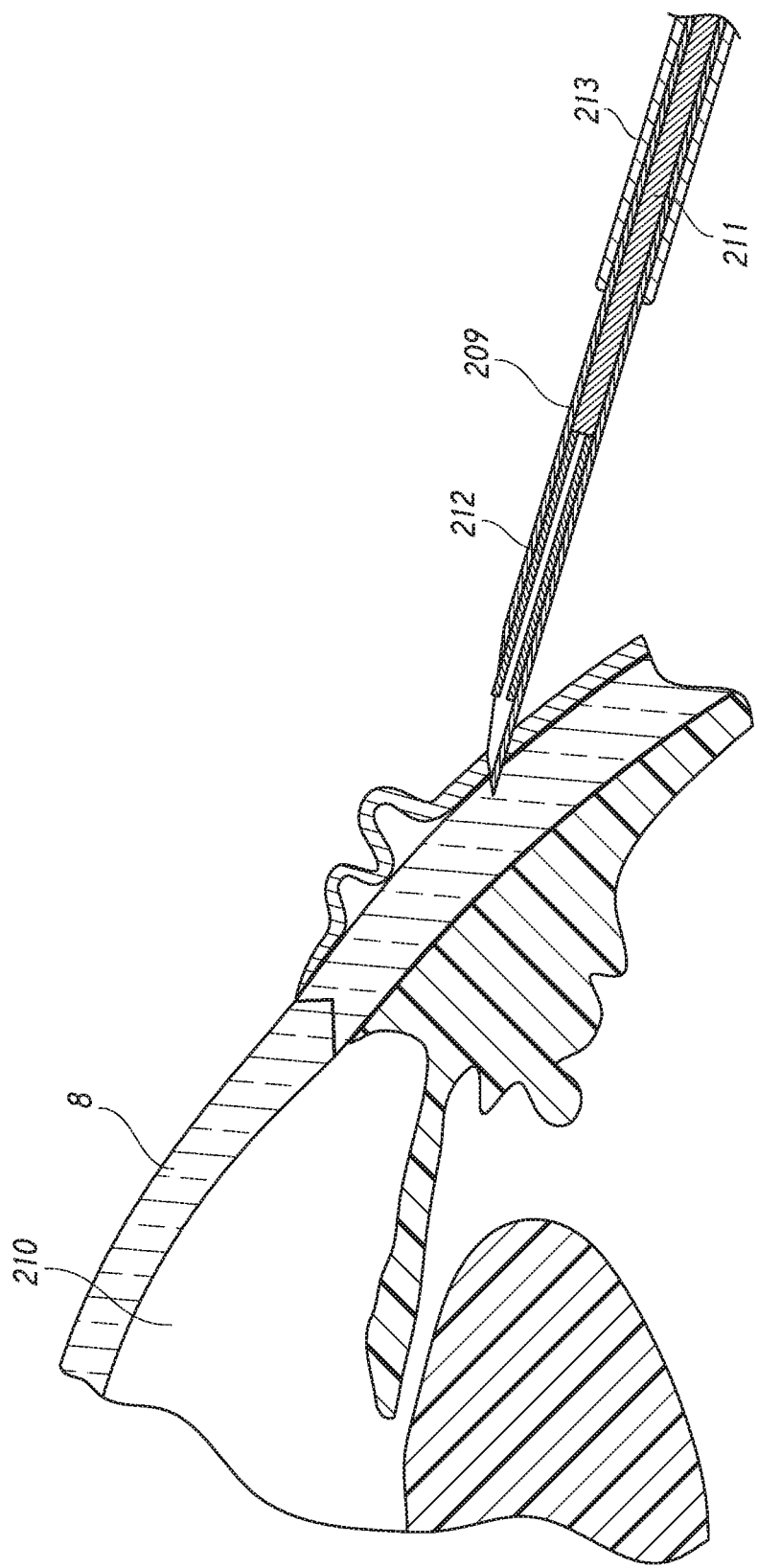
Figure 35:
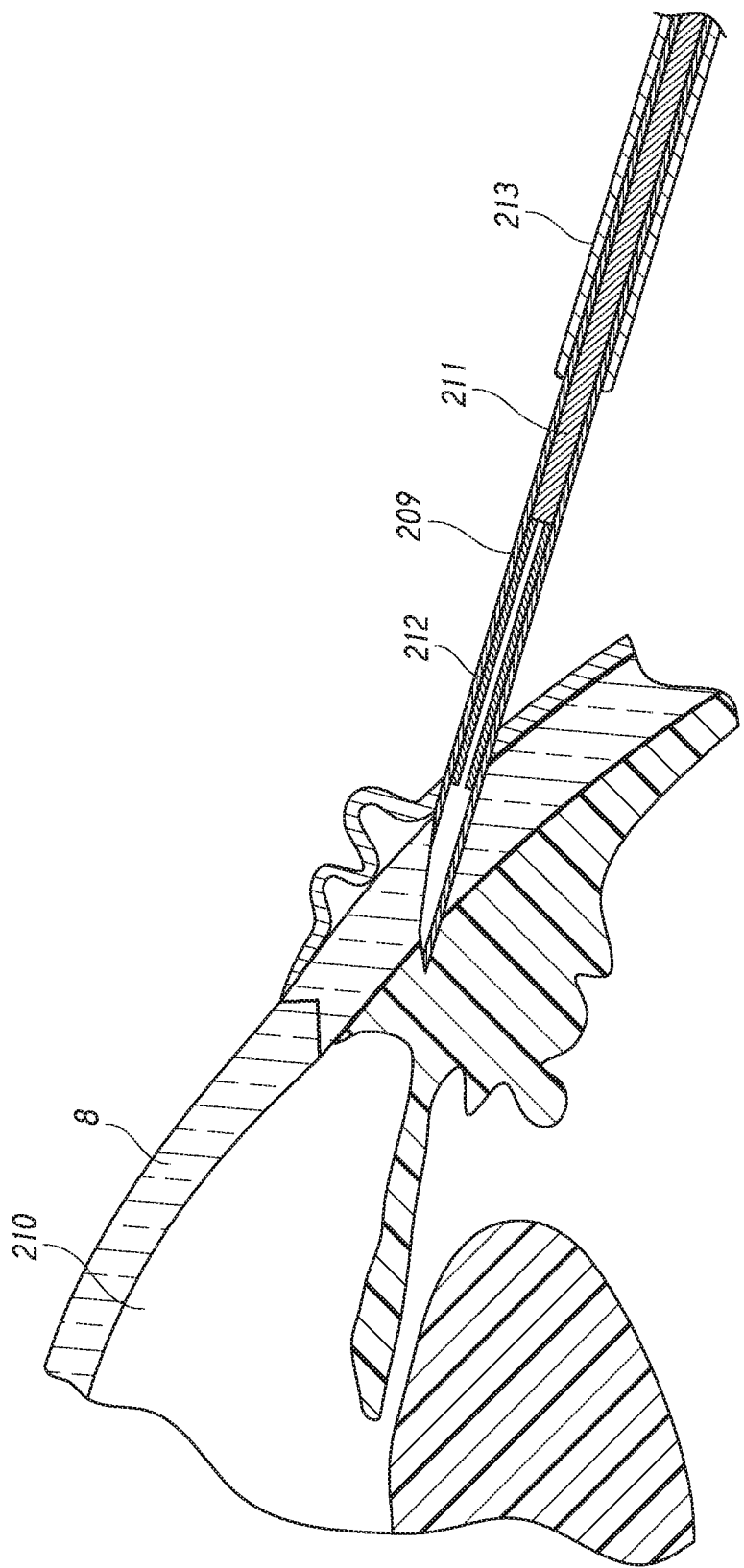
Figure 36:
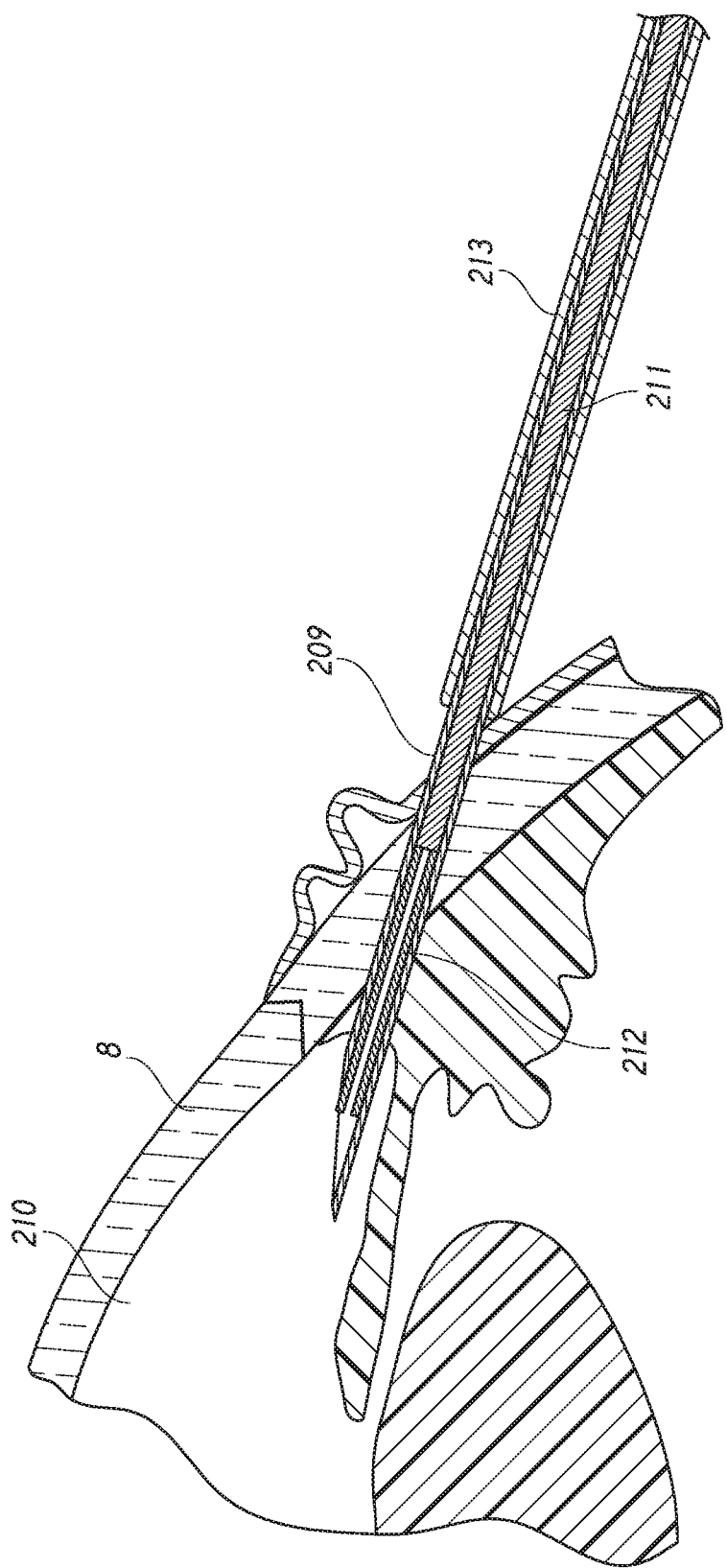
Figure 37:
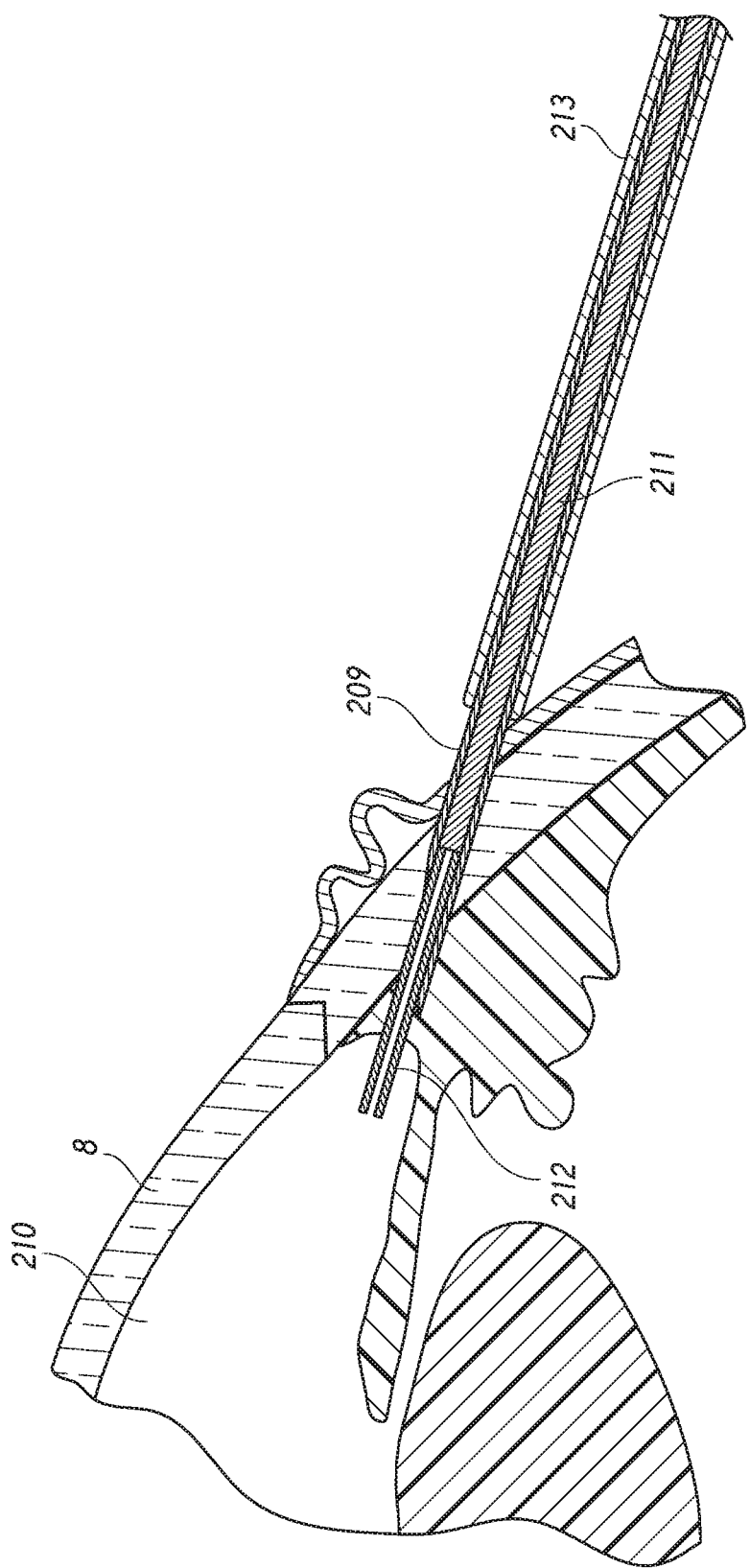
Figure 38:
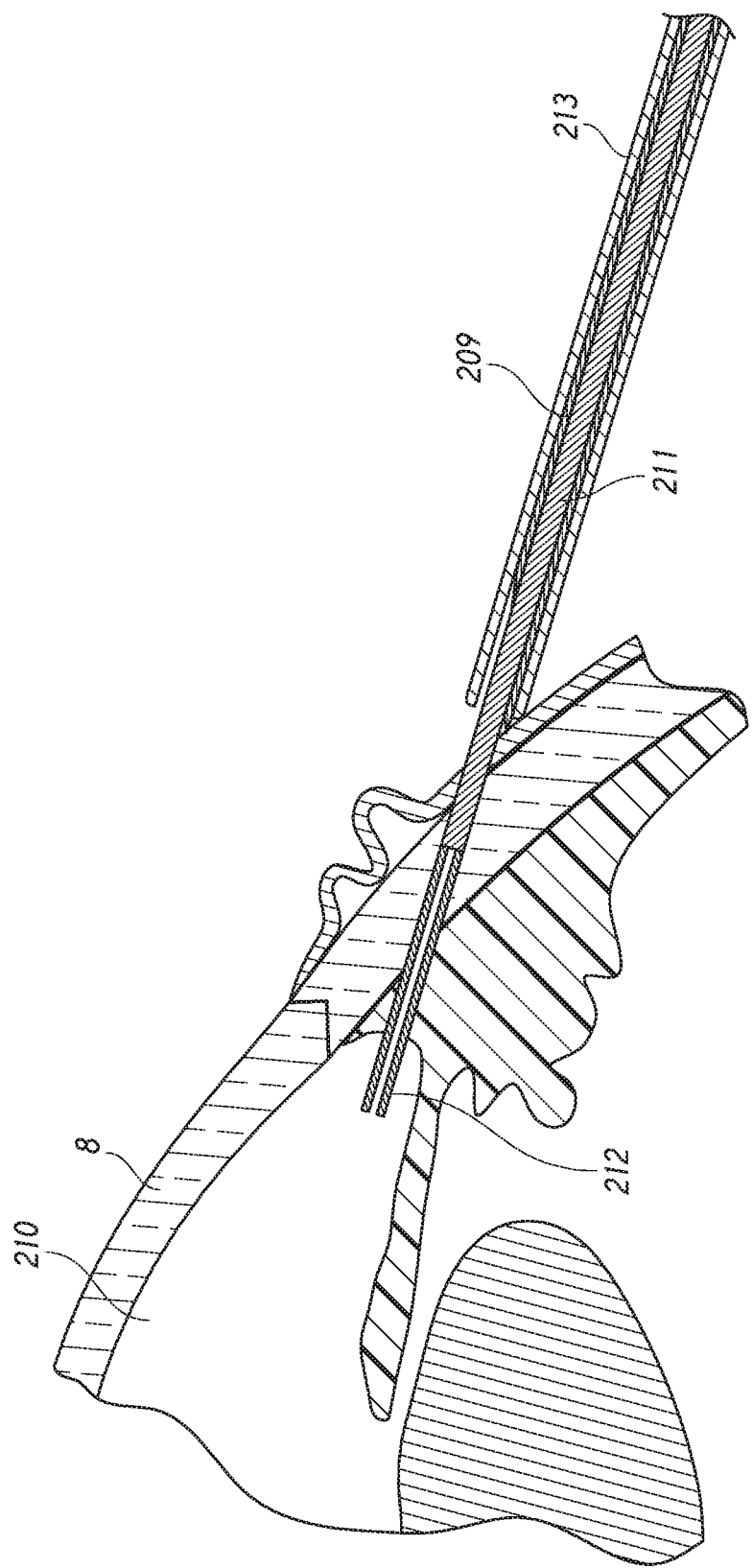
Figure 39:
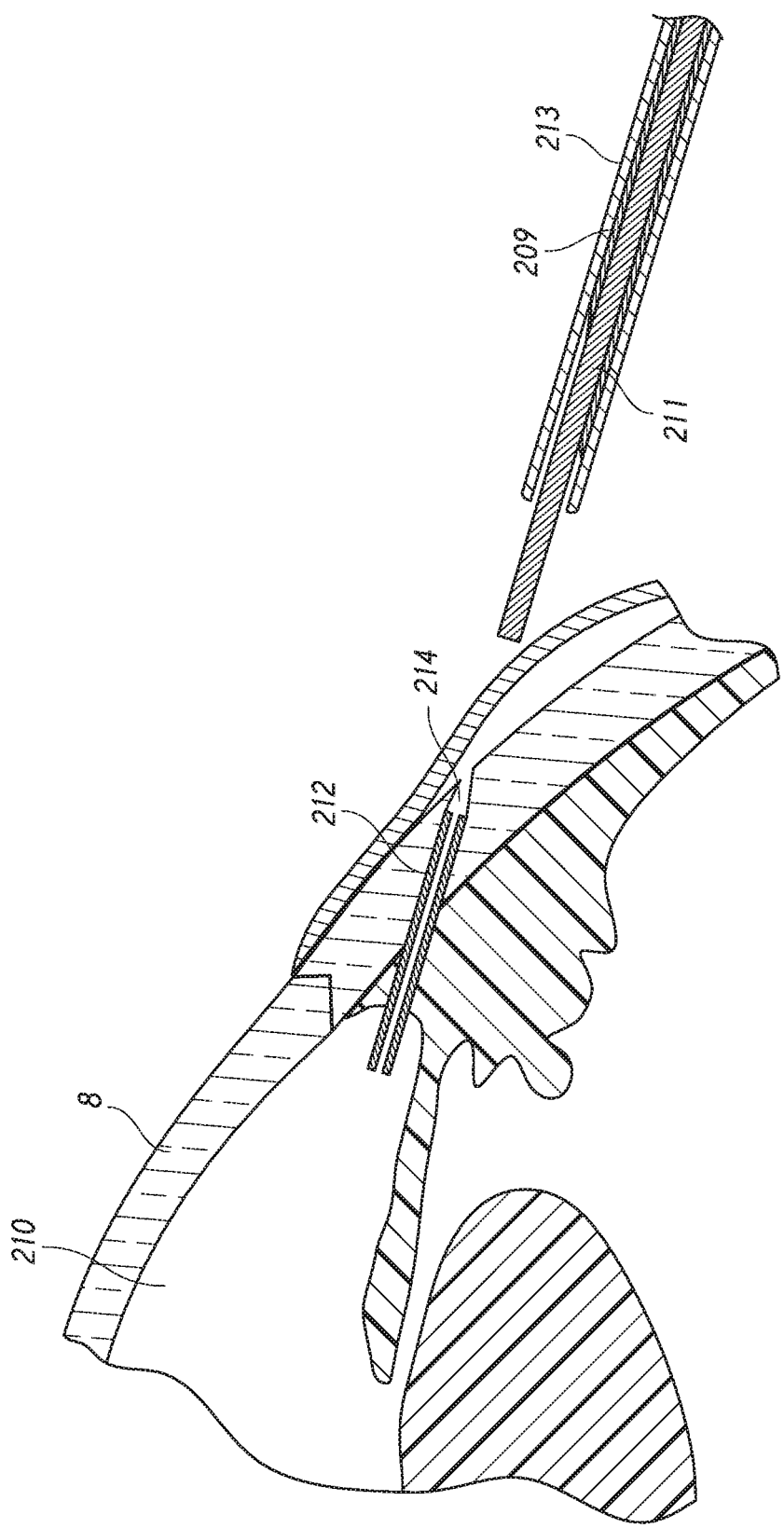

FIGS. 33-39 describes another ab externo method that uses a deployment device. In this method, a distal portion of the deployment device includes a hollow shaft 209 that has a sharpened tip (FIG. 33). A shunt 212 resides within the shaft 209. The distal shaft 209 is advanced into the eye and into the sclera 8 until a proximal portion of the shaft resides in the anterior chamber 210 and a distal portion of the shaft 209 is inside the scleral 8 (FIGS. 34-36). Deployment of the shunt 212 that is located inside the shaft 209 is then accomplished by a mechanism that withdraws the shaft 209 while the shunt 212 is held in place by a plunger 211 behind the proximal end of the shunt 212 (FIGS. 37-39). As the implantation sequence progresses, the shaft 209 is completely withdrawn from the sclera 8. After that, the plunger 211 is withdrawn from the sclera 8, leaving the shunt 212 behind with its distal end inside the sclera 8, its proximal end inside the anterior chamber 210, and a passageway 214 through the sclera 8. In a preferred embodiment the shaft 209 is placed inside a sleeve 213 that is dimensioned in length relative to the shaft 209 such that it will act as stopper during the penetration of the shaft 209 into the eye and at the same time assures controlled longitudinal placement of the shunt 212 relative to the outer surface of the eye. The sleeve 213 may be beveled to match the anatomical angle of the entry site surface.

The shaft penetrates the conjunctival layer before it enters and penetrates the sclera. This causes a conjunctival hole that could create a fluid leakage after the shunt placement has been completed. To minimize the chance for any leakage, a small diameter shaft is used that results in a self-sealing conjunctival wound. To further reduce the chance for a conjunctival leak, a suture can be placed in the conjunctiva around the penetration area after the shunt placement.

Figure 40:
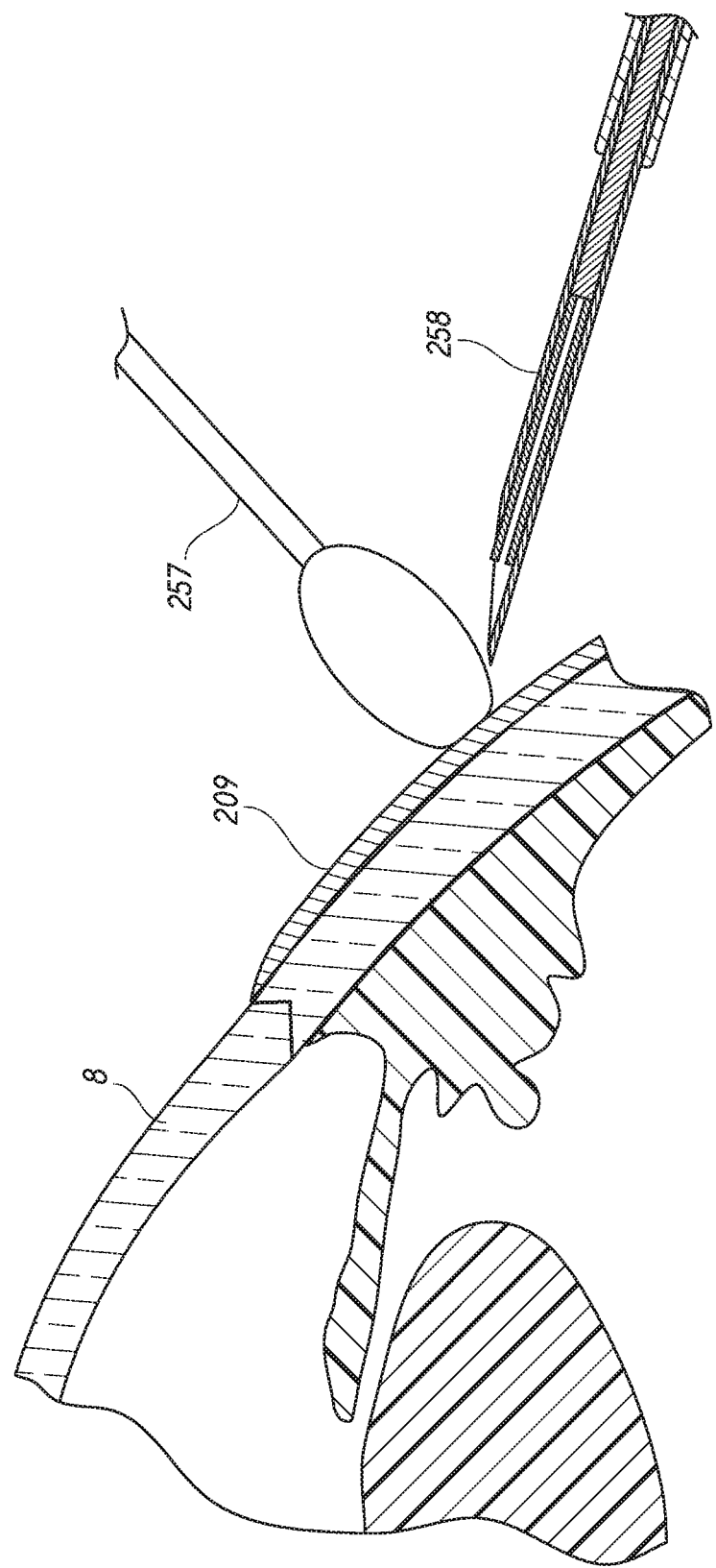
FIGS. 40-41 depict a sequence for ab externo insertion of a shaft of a deployment device using an applicator, according to some embodiments.
Figure 41:
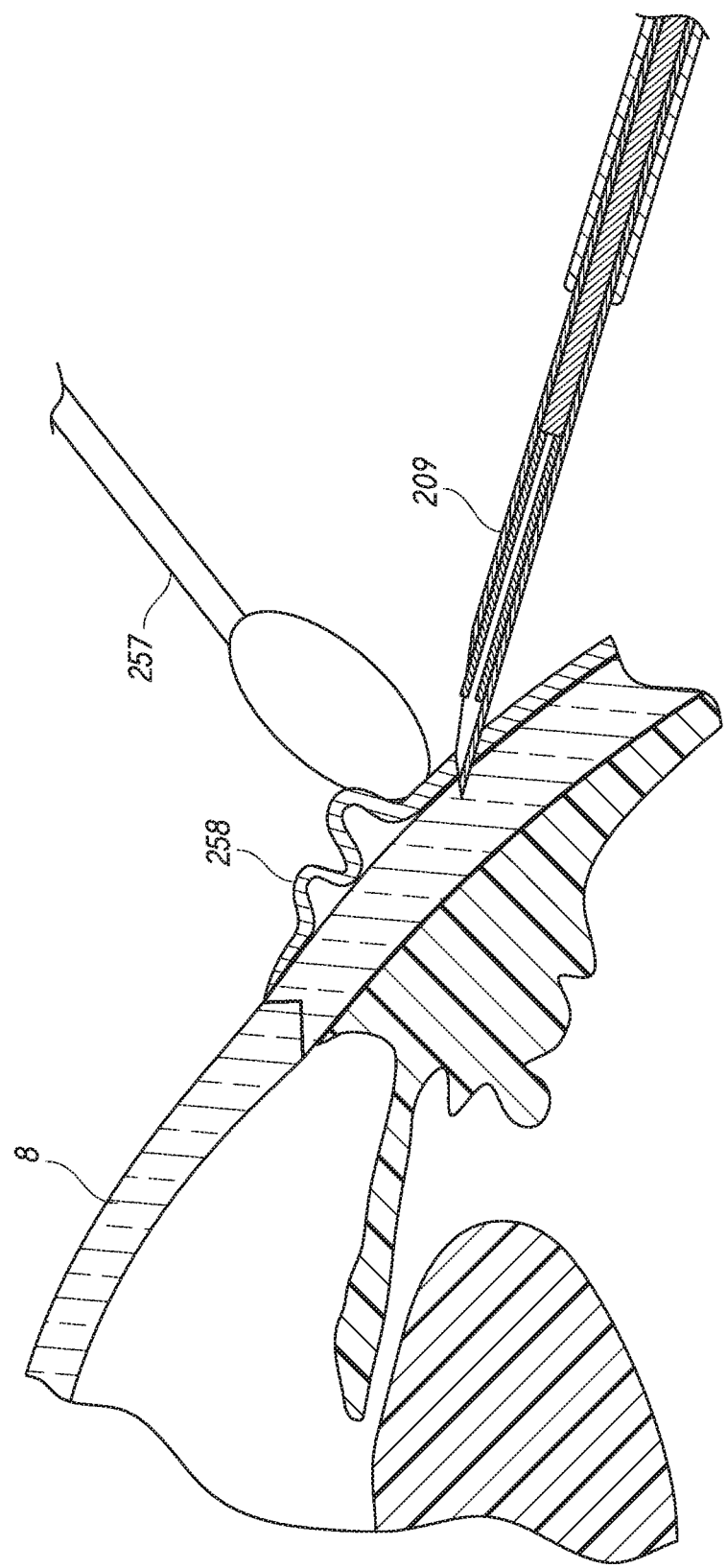

Furthermore the preferred method of penetrating the conjunctiva is performed by shifting the conjunctival layers from posterior to the limbus towards the limbus, using e.g. an applicator such as a Q-tip, before the shaft penetration is started. This is illustrated in FIGS. 40-41. That figure shows that an applicator 257 is put onto the conjunctiva 258, about 6 mm away from the limbus. The loose conjunctiva layer is then pushed towards the limbus to create folding tissue layers that are about 2 mm away from the limbus. The device shaft 209 is now inserted through the conjunctiva and sclera 8 starting about 4 mm away from the limbus. After the shunt placement has been completed, the Q-tip is released and the conjunctival perforation relaxes back from about 4 mm to about 8 mm limb at distance. This can cause the conjunctival perforation to be 4 mm away from the now slowly starting drainage exit. This distance will reduce any potential for leakage and allows for a faster conjunctival healing response. Alternative to this described upward shift, a sideway shift of the conjunctiva or anything in between is feasible as well. In another embodiment of the ab externo method, a conjunctival slit is cut and the conjunctiva is pulled away from the shaft entry point into the sclera. After the shunt placement is completed, the conjunctival slit is closed again through sutures.

In certain embodiments, since the tissue surrounding the trabecular meshwork is optically opaque, an imaging technique, such as ultrasound biomicroscopy (UBM), optical coherence tomography (OCT) or a laser imaging technique, can be utilized. The imaging can provide guidance for the insertion of the deployment device and the deployment of the shunt. This technique can be used with a large variety of shunt embodiments with slight modifications since the trabecular meshwork is punctured from the scleral side, rather than the anterior chamber side, in the ab externo insertion.

In another ab externo approach, a superficial flap may be made in the sclera and then a second deep scleral flap may be created and excised leaving a scleral reservoir under the first flap. Alternatively, a single scleral flap may be made with or without excising any portion of the sclera.

A shaft of a deployment device is inserted under the flap and advanced through the sclera and into an anterior chamber. The shaft is advanced into the sclera until a proximal portion of the shaft resides in the anterior chamber and a distal portion of the shaft is in proximity to the trabecular outflow. The deployment is then performed such that an outlet of the shunt is positioned proximate the second opening in the sclera so that at least some of the fluid that exits the shunt flows through the first opening in the sclera, thereby ensuring that the intrascleral space does not become overwhelmed with fluid output from the shunt. At the conclusion of the ab externo implantation procedure, the scleral flap may be sutured closed. The procedure also may be performed without suturing.

Figure 42:
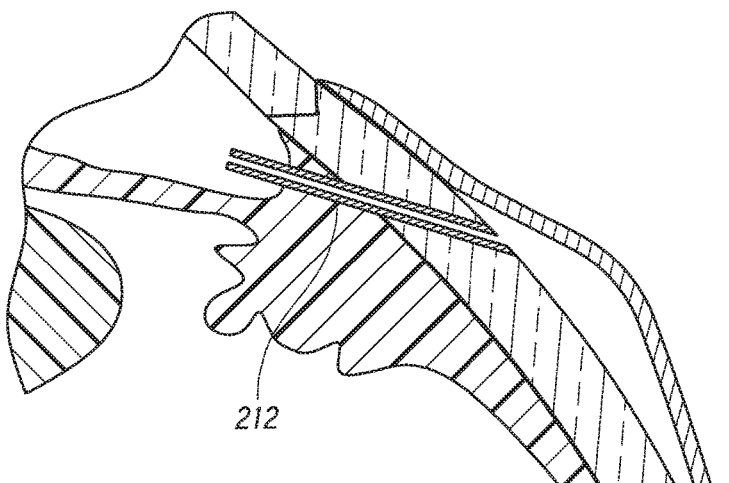
FIG. 42 depicts deployment of the shunt in the intra scleral space where a distal end of the shunt is flush with the sclera surface, according to some embodiments.
Figure 43:
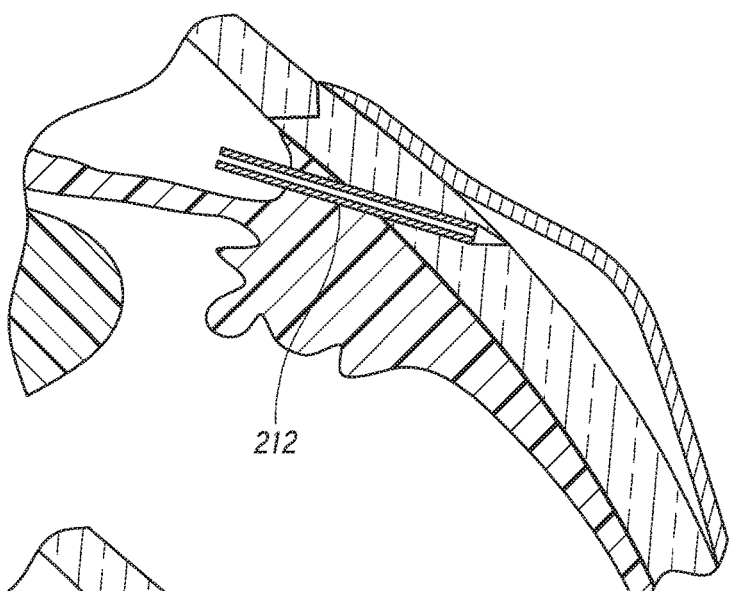
FIG. 43 depicts deployment of the shunt in the intra scleral space where a distal end of the shunt is about 200-500 micron behind the scleral exit, according to some embodiments.
Figure 44:
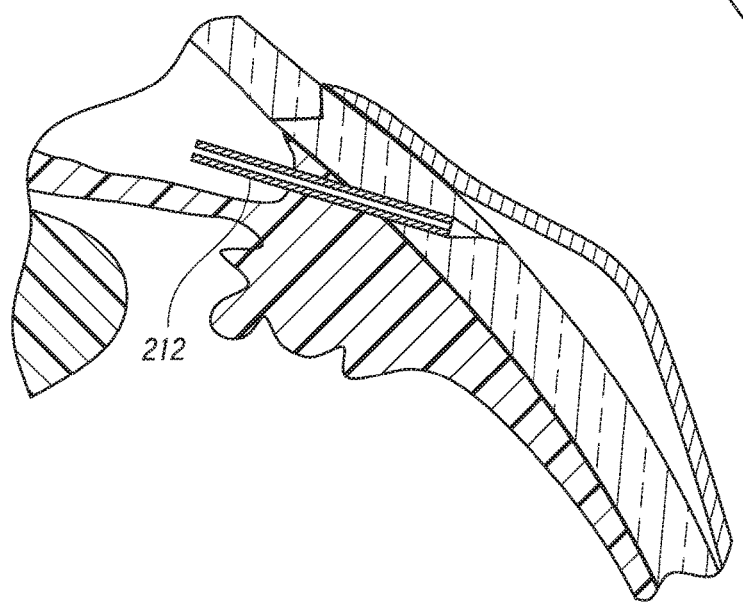
FIG. 44 depicts deployment of the shunt in the intra scleral space where a distal end of the shunt is more than about 500 micron behind the scleral exit, according to some embodiments.

Regardless of the implantation method employed, some embodiments of the methods disclosed herein recognize that the proximity of the distal end of the shunt to the scleral exit slit affects the flow resistance through the shunt, and therefore affects the intraocular pressure in the eye. For example, if the distal end of the shunt 212 is flush with the sclera surface then there is no scleral channel resistance (FIG. 42). In this embodiment, total resistance comes from the shunt 212 alone. In another embodiment, if the distal end of the shunt 212 is about 200 µm to about 500 µm behind the scleral exit, then the scleral slit closes partially around the exit location, adding some resistance to the outflow of aqueous humor (FIG. 43). In another embodiments, if the distal end of the shunt 212 is more than about 500 micron behind the scleral exit, than the scleral slit closes completely around the exit location with no backpressure and opens gradually to allow aqueous humor to seep out when the intraocular pressure raises e.g. above 10 mmHg (FIG. 44). The constant seepage of aqueous humor keeps the scleral slit from scaring closed over time.

Effectively, shunt placement according to some embodiments of the methods disclosed herein achieve a valve like performance where the scleral slit in front of the distal shunt end acts like a valve. The opening (cracking) pressure of this valve can be adjusted by the outer shunt diameter and its exact distal end location relative to the scleral exit site. Typical ranges of adjustment are 1 mmHg to 20 mmHg. This passageway distance can be controlled and adjusted through the design of the inserting device as well as the shunt length and the deployment method. Therefore a specific design can be chosen to reduce or prevent hypotony (<6 mmHg) as a post-operative complication.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. A method comprising inserting an implant through a cornea, in an eye having (i) an anterior chamber and (ii) a sclera, to form a channel through the sclera and thereby establish fluid communication between the anterior chamber and the channel, and administering a pharmaceutical or biological agent to the eye.

2. The method of claim 1, wherein the implant comprises the pharmaceutical or biological agent, and the administering comprises permitting the agent to diffuse into the eye.

3. The method of claim 2, wherein the pharmaceutical or biological agent comprises a coating on a surface of the implant.

4. The method according to claim 3, wherein the pharmaceutical or biological agent comprises a coating on an exterior surface of the implant.

5. The method according to claim 3, wherein the pharmaceutical or biological agent comprises a coating on an interior surface of the implant.

6. The method of claim 2, wherein a portion of the implant is impregnated with the pharmaceutical or biological agent.

7. The method according to claim 1, wherein the administering comprises injecting the pharmaceutical or biological agent into the eye.

8. The method according to claim 1, wherein the pharmaceutical or biological agent comprises a time-release pharmaceutical or biological agent.

9. The method of claim 1, wherein the pharmaceutical or biological agent comprises an anti-mitotic pharmaceutical.

10. The method of claim 1, wherein the pharmaceutical or biological agent comprises Mitomycin-C, 5-Fluorouracil, an anti-VEGF, a VEGF, or a steroid.

11. The method of claim 1, wherein the implant comprises an intraocular shunt and the eye comprises a cornea, and wherein the inserting comprises inserting the intraocular shunt through the cornea and into the anterior chamber.

12. The method of claim 1, further comprising, from within the anterior chamber, piercing the sclera with a hollow shaft such that a distal tip of the shaft enters the sclera to form the channel.

13. The method of claim 1, wherein the inserting comprises positioning an outlet end of the implant between layers of sclera for providing fluid communication from the anterior chamber to a space between the layers.

14. The method of claim 1, wherein the channel comprises a scleral exit, and the inserting comprises positioning an outlet end of the implant approximately more than 500 μm behind the scleral exit to permit the channel to close completely around the scleral exit with no backpressure and open to allow aqueous humor to seep out when intraocular pressure of fluid in the anterior chamber rises.

15. The method of claim 1, wherein the channel terminates in the sclera.

16. A method comprising inserting an intraocular shunt through a cornea of an eye, positioning an outlet end of the shunt in a channel formed within sclera and an inlet end of the shunt in an anterior chamber of the eye, and administering a pharmaceutical or biological agent to the eye.

17. The method of claim 16, further comprising forming the channel in the sclera using a hollow shaft of a deployment mechanism.

18. The method of claim 16, further comprising, from within the anterior chamber, forming a slit in sclera.

19. The method of claim 18, wherein the positioning comprises positioning the outlet end in the slit.

20. The method of claim 16, wherein the positioning comprises positioning the shunt outlet end in the sclera between deep and superficial layers of sclera.

21. The method of claim 16, wherein the shunt comprises the pharmaceutical or biological agent, and the administering comprises permitting the agent to diffuse into the eye.

22. The method of claim 21, wherein the pharmaceutical or biological agent comprises a coating on a surface of the shunt.

23. The method according to claim 22, wherein the pharmaceutical or biological agent comprises a coating on an exterior surface of the shunt.

24. The method according to claim 22, wherein the pharmaceutical or biological agent comprises a coating on an interior surface of the shunt.

25. The method of claim 21, wherein a portion of the shunt is impregnated with the pharmaceutical or biological agent.

26. The method according to claim 16, wherein the administering comprises injecting the pharmaceutical or biological agent into the eye.

27. The method according to claim 16, wherein the pharmaceutical or biological agent comprises a time-release pharmaceutical or biological agent.

28. The method of claim 16, wherein the pharmaceutical or biological agent comprises an anti-mitotic pharmaceutical.

29. The method of claim 16, wherein the pharmaceutical or biological agent comprises Mitomycin-C, 5-Fluorouracil, an anti-VEGF, a VEGF, or a steroid.

30. The method of claim 16, wherein the channel comprises a scleral exit, and the positioning comprises positioning the outlet end of the shunt approximately more than 500 μm behind the scleral exit to permit the channel to close completely around the scleral exit with no backpressure and open to allow aqueous humor to seep out when intraocular pressure of fluid in the anterior chamber rises.

31. The method of claim 16, wherein the channel terminates in the sclera.

* * * * *